US007161010B2

(12) United States Patent
Kobayashi et al.

(10) Patent No.: US 7,161,010 B2
(45) Date of Patent: Jan. 9, 2007

(54) METHINE COMPOUND AND SILVER HALIDE PHOTOGRAPHIC MATERIAL CONTAINING THE SAME

(75) Inventors: Katsumi Kobayashi, Kanagawa (JP); Takashi Katoh, Kanagawa (JP); Junji Nishigaki, Kanagawa (JP)

(73) Assignee: Fuji Photo Film Co., Ltd., Tokyo (JP)

( * ) Notice: Subject to any disclaimer, the term of this patent is extended or adjusted under 35 U.S.C. 154(b) by 0 days.

(21) Appl. No.: 10/631,810

(22) Filed: Aug. 1, 2003

(65) Prior Publication Data

US 2004/0063962 A1 Apr. 1, 2004

Related U.S. Application Data

(62) Division of application No. 09/985,060, filed on Nov. 1, 2001, now Pat. No. 6,667,405, which is a division of application No. 09/522,852, filed on Mar. 10, 2000, now Pat. No. 6,333,146.

(30) Foreign Application Priority Data

Mar. 10, 1999 (JP) ............................... P. 11-63588
Mar. 24, 1999 (JP) ............................... P. 11-80141

(51) Int. Cl.
*C07D 513/04* (2006.01)
*C07D 498/04* (2006.01)
*C07D 487/04* (2006.01)
*C07D 487/14* (2006.01)

(52) U.S. Cl. ...................... 548/149; 548/207; 548/218; 548/151; 548/301.7; 548/302.1

(58) Field of Classification Search ................. 548/149
See application file for complete search history.

(56) References Cited

U.S. PATENT DOCUMENTS 2,202,991 A 6/1940 Middleton
3,623,882 A 11/1971 Gotze et al.
6,180,332 B1 1/2001 Yamashita et al.

OTHER PUBLICATIONS

Avdeeva et al., "J-Aggregation of Thiamonomethinecyanines: 4. Aggregation in Solutions", Sci. Appl. Photo., 1998 39(6), pp. 543-554.

Kanazawa et al., "A New Ring Transforming of Thiazolo [4,5-g] Quinazoline 3-Oxides Into [1,4] Thiazino [3,2-g] Quinazolines By The 1,3-Dipolar Cycloaddition Reaction", Chem. Pharm. Bull., 1986, 34 (3), 1384-1386.

Merchant et al., "Synthesis of Pyranobenzoxazines and 2-Chloromethylpyranobenzoxazoles", Curr. Sci., 1984, 53 (8), 424-425.

*Primary Examiner*—Kahsay Habte
(74) *Attorney, Agent, or Firm*—Sughrue Mion, PLLC

(57) ABSTRACT

Disclosed is a compound represented by the following formula (I):

(I)

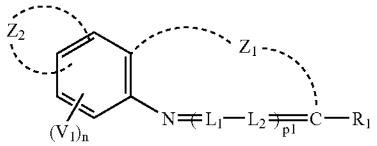

wherein $Z_1$ represents an atomic group necessary to form a 5- or 6-membered nitrogen-containing heterocyclic ring; $Z_2$ represents an atomic group necessary to form a 5- or 6-membered heterocyclic ring, $Z_2$ may further be substituted, or may be condensed with a hetero ring of a benzene ring; $R_1$ represents a hydrogen atom, a halogen atom, a mercapto group, an alkyl group, an alkenyl group, an aryl group, an alkylthio group, an alkenylthio group, or an arylthio group; $L_1$ and $L_2$ each represents a methine group; $p_i$ represents 0 or 1; $V_1$ represents a substituent; and n represents 0, 1 or 2, and when n represents 2, a plurality of $V_1$ may be the same or different.

8 Claims, No Drawings

METHINE COMPOUND AND SILVER HALIDE PHOTOGRAPHIC MATERIAL CONTAINING THE SAME

RELATED APPLICATIONS

This is a divisional of application Ser. No. 09/985,060 filed Nov. 1, 2001, now U.S. Pat. No. 6,667,405 which is a divisional of application Ser. No. 09/522,852 filed Mar. 10, 2000 now U.S. Pat. No. 6,333,146; the disclosures of which are incorporated herein by reference.

FIELD OF THE INVENTION

The present invention relates to a methine dye which is useful as a coloring agent, a light absorber, a dye for an optical disc, spectral sensitizing dyes for a silver halide photograph, an electrophotograph and a photoelectric conversion device, or a marker for diagnosis, and also relates to a nitrogen-containing heterocyclic compound and a quaternary salt compound which are raw materials of the methine dye. The present invention further relates to a silver halide photographic material using the methine dye.

BACKGROUND OF THE INVENTION

Compounds which absorb lights in a visible region develop various colors corresponding to the wavelength of the light absorbed. Such compounds are called dyes or dye stuffs and are used for coloring various materials, and as more higher usages, they are used as dyes for optical discs which are high density data-recording media, as spectral sensitizing dyes for silver halide photographic materials or electrophotographic materials which are image data-recording materials, or as filter dyes.

Dyes for use in these uses are in many cases dissolved in a solution in the first place and then processed to a desired state but as they are actually used in the state of amorphous, a solid state such as a solid dispersion, or an adsorption state, their property as molecular aggregate takes part in the performance of a product in which the are used. A minute molecular structural difference sometimes extremely affects the formation of molecular aggregate.

On the other hand, a spectral sensitizing technique is a very important and essential technique for producing a silver halide photographic material of high speed. With the development of a variety of spectral sensitizing dyes, the technical development in use of these sensitizing dyes such as supersensitizing techniques and addition methods has been done.

As spectral sensitizing dyes for use in spectral sensitization, it is known to use spectral sensitizing dyes, e.g., a cyanine dye, a merocyanine dye, a rhodacyaninedye, alone or in combination (e.g., in the case of supersensitization).

Sensitizing dyes for use for photographic materials should satisfy various conditions That is, sensitizing dyes should be not only capable of achieving high spectral sensitivity but also should be less in fog, excellent in characteristics at exposure (e.g., latent image stability, reciprocity law characteristics, retention of temperature and humidity at exposure, etc.), less in the fluctuations of sensitivity, gradation and fog during storage of samples before exposure, and sensitizing dyes should not remain in a photographic material after development processing Of these conditions, high sensitivity is an essential condition and a great deal of effort has been expended, as disclosed, for example, in JP-A-60-202436 (the term "JP-A" as used herein means an "unexamined published Japanese patent application"), JP-A-60-220339, JP-A-60-25147, JP-A-61-123834, JP-A-62-87953, JP-A-63-264743, JP-A-1-15534, JP-A-1-177533, JP-A-1-198743, JP-A-1-216342, JP-A-2-42, JP-B-60-57583 (the term "JP-B" as used herein means an "examined Japanese patent publication"), and U.S. Pat. No. 6,418,570.

However, some conventional compounds are insufficient in spectral sensitivity in a specific emulsion or in a specific wavelength region and have not reached satisfactory levels yet.

Further, with the realization of rapid development processing of a silver halide photographic material and the large addition amount of sensitizing dyes in recent years, a serious problem that sensitizing dyes contained in a silver halide photographic material do not thoroughly dissolve out during processing to color the photographic material (so-called residual color) has arisen.

Dyes having hydrophilic substituents, e g., a sulfamoyl group and a carbamoyl group, at the nucleus have been investigated as sensitizing dyes which cause less residual color (e.g., JP-A-1-147451, JP-A-61-294429, JP-B-45-3249 and JP-A-61-77843) but these dyes have not reached sufficiently satisfactory level yet The sensitizing dyes disclosed in U.S. Pat. No. 3,282,933 and EP-A-451816 have been certainly improved in residual colors but these dyes are also still not sufficient in the point of a compatibility of residual color with sensitivity.

The sensitivity of a silver halide photographic material is determined by the light absorption factor of a grain, the latent image-forming efficiency including the spectral sensitization efficiency and the minimum size of a latent image.

Of these factors, some well-known techniques with respect to the improvement of the light absorption factor of a grain will be described below. The techniques of high aspect ratio tabular grain emulsions disclosed in U.S. Pat. No. 5,494,789 etc. are techniques capable of increasing the adsorption amount of a dye per a grain as the surface area of a grain is increased, as a result capable of improving the light absorption factor. However, there is a limit in the method of increasing the surface area of a grain by making the aspect ratio of a grain higher, hence it becomes necessary to make the size of a grain larger for improving the light absorption factor of a grain.

In addition to the above, as methods of increasing the grain surface area of one grain, JP-A-58-106532 and JP-A-60-221320 disclose methods of making a pore at one part of a grain, and U.S. Pat. No. 4,643,966 discloses a ruffled grain. However, the forms of these grains are unstable and can be put to practical use with extreme difficulty.

Further, U.S. Pat. No. 5,302,499 discloses that a light absorption factor of a grain can be improved by the layer constitution having spectral sensitization characteristics and an optimal grain thickness. However, the increase of a light absorption factor by the optimization of a grain thickness is at most 10% or so.

Accordingly, it is necessary to increase the light absorption factor of the unit surface area of a grain for remarkably increasing the light absorption factor per one grain while maintaining the grain size small in a stable state. It becomes necessary to heighten the adsorption density of a sensitizing dye for that purpose, but generally used spectral sensitizing dyes are adsorbed onto the monomolecular layer at almost the closest packing density and cannot be adsorbed beyond that.

Some techniques have been suggested for solving this problem. For example, P. B. Gilman, Jr., et al. made a cationic dye adsorb onto the first layer and further an anionic dye onto the second layer as described in *Photographic Science and Engineering*, Vol. 20, No. 3, p. 97 (1976).

G. B. Bird, et al. made a plurality of dyes adsorb onto silver halide by multilayer adsorption and effected sensitization due to Forster type excitation energy transfer as disclosed in U.S. Pat. No. 3,622,316.

Sugimoto et al. performed spectral sensitization due to energy transfer from a luminescent dye in JP-A-63-138341 and JP-A-64-84244.

R. Steiger et al. tried spectral sensitization due to energy transfer from a gelatin-substituted cyanine dye in *Photographic Science and Engineering*, Vol. 27, No. 2, p. 59 (1983).

Ikekawa et al. conducted spectral sensitization due to energy transfer from a cyclodextrin-substituted dye in JP-A-61-251842

These are all trials to intend to make a dye of the amount more than a saturation adsorption amount adsorb onto a silver halide grain, but any of these is not so effective to improve sensitivity. On the contrary, there are problems of the increase of intrinsic desensitization and development inhibition in these patents.

On the other hand, two-component connected dyes comprising two or more non-conjugated chromophores of dyes connected by covalent bonding are disclosed in U.S. Pat. Nos. 2,393,351, 2,425,772, 2,518,732, 2,521,944, 2,592,196 and European Patent 565083. However, the objects of these patents were not to intend to increase a light absorption factor. As techniques which positively aimed at improving a light absorption factor, G. B. Bird and A. L. Borror contrived sensitization by the contribution of energy transfer by the adsorption of connection type sensitizing dye molecules having a plurality of cyanine chromophores to thereby increase a light absorption factor, as disclosed in U.S. Pat. Nos. 3,622,317 and 3,976,493. Borror describes with respect to sensitizing dye compounds having two chromophores connected by an alkylene-amide moiety. These compounds are produced by condensing, a first dye with the quaternary salt of a second dye, then reacting a new quaternary salt with ICI intermediate by an ordinary dye-forming reaction. According to this procedure, two-component connected dyes can be obtained in high yield but sometimes impurities are generated, and these impurities cause desensitization even with an extremely low concentration. In conclusion, the present situation is that sufficient sensitivity improvement cannot be obtained from these techniques.

Ukai, Okazaki and Sugimoto suggest in JP-A-64-91134 to bond at least one substantially non-adsorptive dye containing at least two sulfo group and/or carboxyl group to a spectral sensitizing dye which is adsorbable onto silver halide.

Ral Chand Bishwakalma and Thomas Robert Dobles performed spectral sensitization by using two-component connected dyes comprising connecting cyanine adsorptive onto silver halide and non-adsorptive oxonol as disclosed in JP-A-6-27578, but it cannot be said that sufficient improvement of sensitization by the contribution of energy transfer has been attained.

Thus any method of the above patents and literature is insufficient with respect to the light absorption factor per a unit area of silver halide grain and further technical development is required.

Not many a methine compound having a heterocyclic condensed ring type and benzene condensed ring type basic nucleus has been known until now. For example, a cyanine dye having indole[2,3-f]benzothiazole as a nucleus and a cyanine dye having benzothieno[2,3-f]benzothiazole as a nucleus described in, *Zu Nauchn Prikl Fotogr.*, 1997, 42 (6)., 27, a cyanine dye having methylenedioxy-substituted benzothiazole described in JP-A-2-272443, an oxyindole condensed ring type oxazole derivative disclosed in European Patent 334289, a tetrahydrodioxoquinazoline condensed ring type thiazole derivative described in *Chem. Pharm. Bull.*, 1986, 34 (3), 1384, and cyanine dyes having a coumarine condensed ring type thiazole derivative and a dihydrooxobenzo condensed ring type thiazole as a nucleus described in *Curr. Sci.*, 1984, 53 (8), 424 are known. Cyanine dyes derived from benzofuro[2,3-f]benzoxazole are disclosed in British Patent 1,168,495, but indole[3,2-f]benzoxazole, benzothieno[f]benzoxazole, benzofuro[3,2-f]benzoxazole, etc., having different condensed ring forms are not known.

SUMMARY OF THE INVENTION

An object of the present invention is to provide a novel methine compound which is high speed and causes less residual color in a silver halide photographic material, in addition, which is promising in other uses as a coloring agent, a light absorber, a dye for an optical disc, spectral sensitizing dyes for an electrophotograph and a photoelectric conversion device, and to provide a nitrogen-containing heterocyclic compound and a quaternary salt compound which are raw materials of the methine compound. Another object of the present invention is to provide a high speed silver halide photographic material.

As a result of earnest investigations by the present inventors, the above objects of the present invention have been attained by the following items (1) to (14). That is:

(1) A compound represented by the following formula (I):

(I)

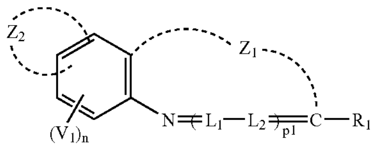

wherein $Z_1$ represents an atomic group necessary to form a 5- or 6-membered nitrogen-containing heterocyclic ring; $Z_2$ represents an atomic group necessary to form a 5- or 6-membered heterocyclic ring, $Z_2$ may further be substituted, or may be condensed with a hetero ring or a benzene ring; $R_1$ represents a hydrogen atom, a halogen atom, a mercapto group, an alkyl group, an alkenyl group, an aryl group, an alkylthio group, an alkenylthio group, or an arylthio group; $L_1$ and $L_2$ each represents a methine group; $p_1$ represents 0 or 1; $V_1$ represents a substituent; and n represents 0, 1 or 2, and when n represents 2, a plurality of $V_1$ may be the same or different.

(2) A compound represented by the following formula (II):

(II)

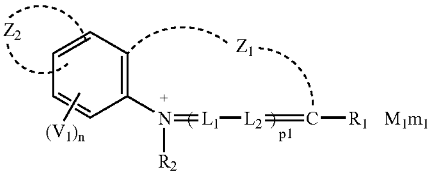

wherein $Z_1$, $Z_2$, $R_1$, $L_1$, $L_2$, $p_1$, $V_1$, and n each has the same meaning as described in formula (I); $R_2$ represents an alkyl group, an aryl group, or a heterocyclic group; $M_1$ represents an electric charge balancing counter ion; and $m_1$ represents a number of from 0 to 10 necessary to neutralize the electric charge of the molecule.

(3) A compound represented by the following formula (III):

(III)

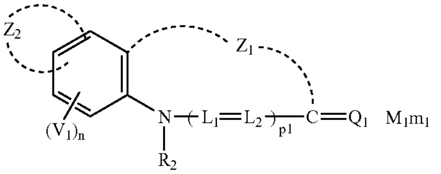

wherein $Z_1$, $Z_2$, $L_1$, $L_2$, $p_1$, $V_1$, n, $R_2$, $M_1$, and $m_1$ each has the same meaning as described in formulae (I) and (II); and $Q_1$ represents a methine group or a polymethine group necessary to form a methine dye.

(4) The compound represented by formula (I), (II) or (III) as described in the above item (1), (2) or (3), wherein $Z_2$ represents a furan ring, a thiophene ring, or a pyrrole ring.

(5) The compound as described in the above item (1) or (4), wherein the compound represented by formula (I) is represented by the following formula (IV) or (V):

(IV)

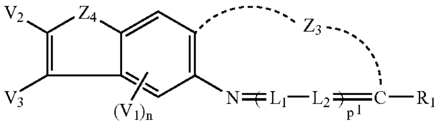

wherein $Z_4$ represents an oxygen atom or a sulfur atom; $Z_3$ represents an atomic group necessary to form a 5- or 6-membered nitrogen-containing heterocyclic ring; $V_2$ and $V_3$ each represents a substituent, or $V_2$ and $V_3$ may form a condensed ring containing $V_2$ and $V_3$ such as a benzene ring or a heterocyclic ring; and $R_1$; $L_1$, $L_2$, $p_1$, $V_1$, and n each has the same meaning as described in formula (I);

(V)

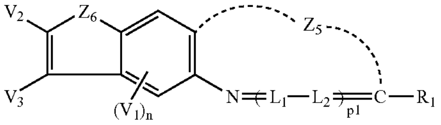

wherein $Z_6$ represents N—$R_3$— $Z_5$ represents an atomic group necessary, to form a 5- or 6-membered nitrogen-containing heterocyclic ring exclusive of a sulfur atom; $R_3$ represents a hydrogen atom or a substituent; $R_1$, $L_1$, $L_2$, $p_1$, $V_1$, and n each has the same meaning as described in formula (I); and $V_2$ and $V_3$ each has the same meaning as described in formula (IV).

(6) The compound as described in the above item (2) or (5), wherein-the compound represented by formula (II) is represented by the following formula (VI) or (VII):

(VI)

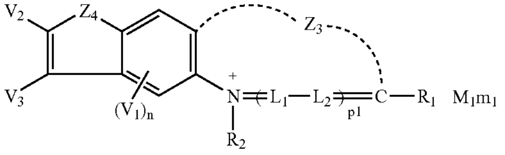

wherein $Z_4$ and $Z_3$ each has the same meaning as described in formula (IV); $R_1$, $L_1$, $L_2$, $p_1$, $V_1$, n, $R_2$, $M_1$, and $m_1$ each has the same meaning as described in formulae (I) and (II); and $V_2$ and $V_3$ each has the same meaning as described in formula (IV);

(VII)

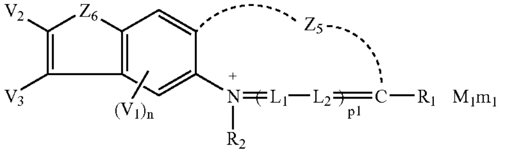

wherein $Z_6$ and $Z_5$ each has the same meaning as described in formula (V); $R_1$, $L_1$, $L_2$, $p_1$, $V_1$, n, $R_2$, $M_1$, and $m_1$ each has the same meaning as described in formulae (I) and (II); and $V_2$ and $V_3$ each has the same meaning as described in formula (IV).

(7). The compound as described in the above item (3) or (6), wherein the compound represented by formula (III) is represented by the following formula (VIII) or (IX):

(VIII)

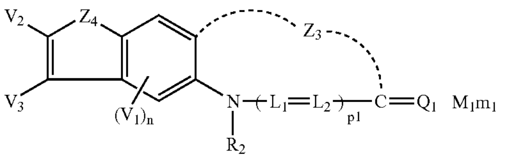

wherein $Z_4$ and $Z_3$ each has the same meaning as described in formula (IV); $L_1$, $L_2$, $p_1$, $V_1$, n, $R_2$, $M_1$, and $m_1$ each has the same meaning as described in formulae (I) and, (II); $V_2$ and $V_3$ each has the same meaning as described in formula (IV); and $Q_1$ has the same meaning as described in formula (III);

(IX)

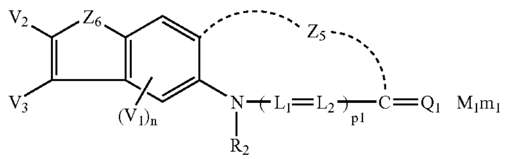

wherein $Z_6$ and $Z_5$ each has the same meaning as described in formula (V); $L_1$, $L_2$, $p_1$, $V_1$, n, $R_2$, $M_1$, and $m_1$ each has the same meaning as described in formulae (I) and (II); $V_2$ and $V_3$ each has the same meaning as described in formula (IV); and $Q_1$ has the same meaning as described in formula (III).

(8) The compound represented by formula (II), (III), (VI), (VII), (VIII) or (IX) as described in the above item (2), (3), (4), (6) or (7), wherein $R_2$ represents an alkyl group having an aryl group or a heterocyclic group as a substituent, an aryl group, or a heterocyclic group. (9) The compound represented by formula (I), (II), (III), (IV), (V), (VI), (VII), (VIII) or (IX), as described in any of the above items (1) to (7), wherein at least one substituent represented by $V_1$ is a group having at least one dissociable group.

(10) The compound represented by formula (I), (II) or (III) as described in the above item (1), (2) or (3), wherein a group having at least one dissociable group is substituted on the heterocyclic group represented by $Z_2$.

(11) The compound represented by formula (IV), (V); (VI), (VII), (VIII) or (IX) as described in the above item (4), (5), (6) or (7), wherein at least one substituent represented by $V_2$ or $V_3$ is a group having at least one dissociable group.

(12) The compound represented by formula (I), (II), (III), (IV), (V), (VI), (VII), (VIII) or (IX) as described in the above item (9), (10) or (11), wherein at least one dissociable group contained in the substituents substituted on the heterocyclic group represented by $V_1$, $V_2$, $V_3$ or $Z_2$ is a sulfo group or a carboxyl group.

(13) A silver halide photographic material which contains at least one compound represented by formula (I), (II), (III), (IV), (V), (VI), (VII), (VIII) or (IX) as described in any one of the above items (1) to (12).

(14) A silver halide photographic material comprising at least one silver halide emulsion layer which contains at least one compound represented by formula (III), (VIII) or (IX) as described in the above item (8) in an amount corresponding to 80% of the saturated adsorption amount of the compound; and contains sensitizing dyes in an amount corresponding to 160% or more of the saturated adsorption amount of the total addition amount of the sensitizing dyes.

Of the compound represented by formula (I), (IV) or (V), the compound represented by formula (IV) or (V) is preferred, and the compound represented by formula (IV) is more preferred. Of the compound represented by formula (II), (VI) or (VII), the compound represented by formula (VI) or (VII) is preferred, and the compound represented by formula (VI) is more preferred Of the compound represented by formula (III), (VIII) or (IX), the compound represented, by formula (VIII) or (IX) is preferred, and the compound represented by formula (VIII) is more preferred. All the compounds represented by formulae (IV) to (IX) are novel compounds. The nitrogen atoms of the heterocyclic compounds represented by formulae (I), (IV) and (V) can easily be quaternized and derived to the quaternary salt compounds represented by formulae (II), (VI) and (VII) according to the method described in F. M. Harmer, *Heterocyclic Compounds—Cyanine Dyes and Related Compounds*, and further can be derived to the methine compounds represented by formulae (III), (VIII) and (IX).

$Z_2$ in formula (I) represents an atomic group necessary to form a 5- or 6-membered heterocyclic ring by the condensation with a benzene ring, and the heterocyclic ring formed by $Z_2$ may be condensed at any position on the benzene ring. Accordingly, formula (I) can be represented by any of the following formulae (X), (XI) and (XII):

(X)

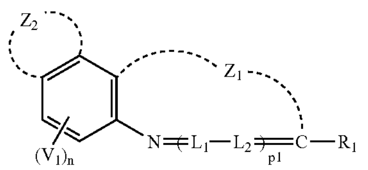

wherein $Z_1$, $Z_2$, $R_1$, $L_1$, $L_2$, $p_1$, $V_1$, and n each has the same meaning as described in formula (I);

(XI)

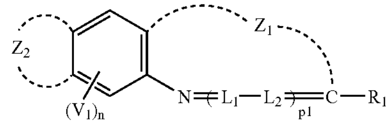

wherein $Z_1$, $Z_2$, $R_1$, $L_1$, $L_2$, $p_1$, $V_1$, and n each has the same meaning as described in formula (I);

(XII)

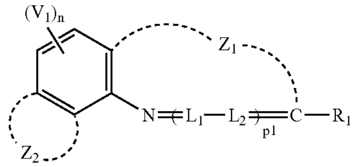

wherein $Z_1$, $Z_2$, $R_1$, $L_1$, $L_2$, $p_1$, $V_1$, and n each has the same meaning as described in formula (I).

Of the compound represented by formula (X), (XI) or (XII), the compound represented by formula (XI) is preferred.

The similar definition can be applied to formula (II) or (III).

DETAILED DESCRIPTION OF THE INVENTION

The compounds according to the present invention will be described in detail below.

$Z_1$ in the compounds represented by formulae (I), (II) and (III) represents an atomic group necessary to form a 5- or 6-membered nitrogen-containing heterocyclic ring. The nitrogen-containing heterocyclic compounds formed by $Z_1$ are not particularly restricted and preferred examples include, e.g., a thiazole nucleus, an oxazoline nucleus, a thiazoline nucleus, an oxazole nucleus, a selenazole nucleus, a tellurazole nucleus, an isooxazole nucleus, an isothiazole nucleus, a pyrazole nucleus, a 3,3-dialkyl-3H-pyrrole nucleus (e.g., 3,3-dimethyl-3H-pyrrole), an imidazole nucleus, an imidazoline nucleus, a 2-pyridine nucleus, a 4-pyridine nucleus, a pyridazine nucleus, a pyrazine nucleus, and a pyrimidine nucleus, more preferred examples include a thiazole nucleus, an oxazole nucleus, a selenazole nucleus, a 3,3-dialkyl-3H-pyrrole nucleus (e.g., 3,3-dimethyl-3H-pyrrole), an imidazole nucleus, a 2-pyridine nucleus, and a 4-pyridine nucleus, and particularly preferred examples include a thiazole nucleus, an oxazole nucleus, an imidazole nucleus, a 2-pyridine nucleus, and a 4-pyridine nucleus.

When the substituent on $Z_1$ is taken as V, the substituent represented by V is not particularly restricted and examples include a halogen atom (e.g., chlorine, bromine, iodine, fluorine), a mercapto group, a cyano group, a carboxyl group, a phosphoric acid group, a sulfo group, a hydroxyl group, a carbamoyl group having from 1 to 10, preferably from 2 to 8, and more preferably from 2 to 5, carbon atoms (e.g., methylcarbamoyl, ethylcarbamoyl, morpholinocarbonyl), a sulfamoyl group having from 0 to 10, preferably from 2 to 8, and more preferably from 2 to 5, carbon atoms (e.g., methylsulfamoyl, ethylsulfamoyl, piperidinosulfonyl), a nitro group, an alkoxyl group having from, 1 to 20, preferably from 1 to 10, and more preferably from 1 to 8, carbon atoms (e.g., methoxy, ethoxy, 2-methoxyethoxy, 2-phenylethoxy), an aryloxy group having from 6 to 20, preferably from 6 to 12, and more preferably from 6 to 10, carbon atoms (e.g., phenoxy, p-methylphenoxy, p-chlorophenoxy, naphthoxy), an acyl group having from 1 to 20, preferably from 2 to 12, and more preferably from 2 to 8, carbon atoms (e.g., acetyl, benzoyl, trichloroacetyl) an acyloxy group having from 1 to 20, preferably from 2 to 12, and more preferably from 2 to 8, carbon atoms (e g., acetyloxy, benzoyloxy), an acylamino group having from 1 to 20, preferably from 2 to 12, and more preferably from 2 to 8, carbon atoms (e.g., acetylamino), a sulfonyl group having from 1 to 20, preferably from 1 to 10, and more preferably from 1 to 8, carbon atoms (e.g., methanesulfonyl., ethanesulfonyl, benzenesulfonyl), a sulfinyl group having from 1 to 20, preferably from 1 to 10, and more preferably from 1 to 8, carbon atoms (e.g., methanesulfinyl, ethanesulfinyl, benzenesulfinyl), a sulfonylamino group having from 1 to 20, preferably from 1 to 10, and more preferably from 1 to 8, carbon atoms (e.g., methanesulfonylamino, ethanesulfonylamino, benzenesulfonylamino), an amino group, a substituted amino group having from 1 to 20, preferably from 1 to 12, and more preferably from 1 to 8, carbon atoms (e.g., methylamino, dimethylamino, benzylamino, anilino, diphenylamino), an ammonium group having from 0 to 15, preferably from 3 to 10, and more preferably from 3 to 6, carbon atoms (e.g., trimethylammonium, triethylammonium), a hydrazino group having from 0 to 15, preferably from 1 to 10, and more preferably from 1 to 6, carbon atoms (e.g., trimethylhydrazino), a ureido group having from 1 to 15, preferably from 1 to 10, and more preferably from 1 to 6, carbon atoms (e.g., ureido, N,N-dimethylureido), an imido group having from 1 to 15, preferably from 1 to 10, and more preferably from 1 to 6, carbon atoms (e.g., succinimido), an alkylthio group having from 1 to 20, preferably from 1 to 12, and more preferably from 1 to 8, carbon atoms (e.g., methylthio, ethylthio, propylthio), anarylthio group having from 6 to 20, preferably from 6 to 12, and more preferably from 6 to 10, carbon atoms (e.g., phenylthio, p-methylphenylthio, p-chlorophenylthio, 2-pyridylthio, naphthylthio), an alkoxycarbonyl group having from 2 to 20, preferably from 2 to 12, and more preferably from 2 to 8, carbon atoms (e.g., methoxycarbonyl, ethoxycarbonyl, 2-benzyloxycarbonyl), an aryloxycarbonyl group having from 6 to 20, preferably from 6 to 12, and more preferably from 6 to 10, carbon atoms (e.g., phenoxycarbonyl), an unsubstituted alkyl group having from 1 to 18, preferably from 1 to 10, and more preferably from 1 to 5, carbon atoms (e.g., methyl, ethyl, propyl, butyl), a substituted-alkyl group having from 1 to 18, preferably from 1 to 10, and more preferably from 1 to 5, carbon atoms (e.g., hydroxymethyl, trifluoromethyl, benzyl, carboxyethyl, ethoxycarbonylmethyl, acetylaminomethyl, in addition, an unsaturated hydrocarbon group having from 2 to 18, preferably from 3 to −10, more preferably from 3 to 5, carbon atoms (e.g., vinyl, ethynyl, 1-cyclohexenyl, benzylidyne, benzylidene) is also to be included in a substituted alkyl group), a substituted or unsubstituted aryl group having from 6 to 20, preferably from 6 to 15, and more preferably from 6 to 10, carbon atoms (e.g., phenyl, naphthyl, p-carboxyphenyl, p-nitrophenyl, 3,5-dichlorophenyl, p-cyanophenyl, m-fluorophenyl, p-tolyl), and a substituted or unsubstituted heterocyclic group having from 1 to 20, preferably from 2 to 10, and more preferably from 4 to 6, carbon atoms (e.g., pyridyl, 5-methylpyridyl, thienyl, furyl, morpholino, tetrahydrofurfuryl). The heterocyclic group may have the condensed structure of a benzene ring and a naphthalene ring.

These substituents may further be substituted with V.

Preferred substituents are an alkyl group, an aryl group, an alkoxyl group, a halogen atom, and a condensed benzene ring, and more preferred substiuents are a methyl group, a phenyl group, a methoxy group, a chlorine atom, a bromine atom, an iodine atom, and a condensed benzene ring.

$Z_2$ represents an atomic group necessary to form a 5- or 6-membered heterocyclic ring by the condensation with a benzene ring, and the heterocyclic ring formed by $Z_2$ may be condensed at any position on the benzene ring.

Examples of the heterocyclic ring formed by $Z_2$ include a furan ring, a thiophene ring, a pyrrole ring, a pyrazole ring, an isooxazole ring, an isothiazole ring, an imidazole ring, a pyridine ring, a pyridazine ring, a pyrimidine ring, and a pyrazine ring. These heterocyclic rings may be a dihydro-body or a tetrahydro-body which is the reductant thereof, or may be oxo-substituted. Further, they may be condensed by substitution or an aromatic ring. Preferred examples of the heterocyclic ring formed by $Z_2$ include a furan ring, a thiophene ring, a pyrrole ring, a benzofuran ring, a benzothiophene ring, and an indole ring, more preferred are a furan ring, a pyrrole ring, a benzofuran ring, and an indole ring, and particularly preferred are a furan ring and a benzofuran ring.

The case in which a group having at least one dissociable group is substituted on the heterocyclic ring represented by $Z_2$ is particularly preferred.

Preferred dissociable groups-are a sulfo group and a carboxyl group.

Examples of the heterocyclic group formed by $Z_3$ include a thiazole ring, an imidazole ring, an oxazole ring and a pyridine ring, and preferred is an oxazole ring.

Examples of the heterocyclic group formed by $Z_5$ include an imidazole ring, an oxazole ring and a pyridine ring, and preferred is an oxazole ring.

$Z_4$ represents an oxygen atom or a sulfur atom, preferably an oxygen atom. $Z_6$ represents N—$R_3$.

$V_1$ represents a substituent, and those described in the definition of V can be exemplified as the examples of the substituents. n represents 0, 1 or 2, and when n represents 2, a plurality of $V_1$ may be the same or different.

$V_2$ and $V_3$ each represents a hydrogen atom or a substituent and those described in the definition of V can be exemplified as the examples of the substituents $V_2$ and $V_3$ may form a condensed ring containing $V_2$ and $V_3$. As the condensed ring containing $V_2$ and $V_3$, an aromatic hydrocarbon ring or a heterocyclic ring can be exemplified. As the aromatic hydrocarbon ring, a benzene ring, a naphthalene ring and an anthracene ring can be exemplified, and as the heterocyclic ring, those described in the definition of $Z_2$ and $Z_1$ can be exemplified. $V_2$ and $V_3$ preferably represent a hydrogen atom, a substituted or unsubstituted aromatic hydrocarbon ring, i.e., a condensed ring containing $V_2$ and $V_3$, or a heterocyclic ring.

The case where at least one substituent represented by V, $V_1$, $V_3$ or $Z_2$ is a group having at least one dissociable group is preferred. The dissociable group used herein may be any group so long as it has a dissociable proton and has negative charge at proton dissociation, e.g., a sulfo group, a carboxyl group, a phosphonic acid group, and a hydroxyl group, can be exemplified, preferred groups are a sulfo group, a carboxyl group, and particularly preferred group is a sulfo group. Such a dissociable group may not have a proton and form a salt with a counter cation in the form of an anion.

$R_3$ represents a hydrogen atom or a substituent, and those described in the definition of V can be exemplified as the examples of the substituents. $R_3$ preferably represents a hydrogen atom, an unsubstituted alkyl group having 18 or less carbon atoms (e.g., methyl, ethyl, propyl, butyl, pentyl), a substituted alkyl group (as the substituents, e.g., a halogen atom, an alkoxyl group, a cyano group, a sulfo group, a hydroxyl group, an acyl group, an acylamino group, an aryloxy group, and an alkyl group substituted with an arylamino group can be exemplified), an unsubstituted aryl group having 20 or less carbon atoms (e.g., phenyl, naphthyl), and a substituted aryl group (as the substituents, e g., a halogen atom, an alkoxyl group, a cyano group, a sulfo group, a hydroxyl group, an acyl group, an acylamino group, an aryloxy group, and an aryl group substituted with an arylamino group can be exemplified), an unsubstituted heterocyclic group having 18 or less carbon atoms (e.g., furan, thiophene, pyrrole), a substituted heterocyclic group (as the substituents, e.g., a halogen atom, an alkoxyl group, a cyano group, a sulfo group, a hydroxyl group, an acyl group, an acylamino group, an aryloxy group, and a heterocyclic group substituted with an arylamino group can be exemplified), an alkoxyl group, a cyano group, a sulfo group, a hydroxyl group, an acyl group, an acylamino group, an aryloxy group, or an arylamino group, more preferably represents a hydrogen atom, an unsubstituted alkyl group having 18 or less carbon atoms (e.g., methyl, ethyl, propyl, butyl, pentyl), or a substituted alkyl group (as the substituents, e.g., a halogen atom, an alkoxyl group, a cyano group, a sulfo group, a hydroxyl group, an acyl group, an acylamino group, an aryloxy group, and an alkyl group substituted with an arylamino group can be exemplified), and particularly preferably represents a methyl group, an ethyl group, a propyl group, a butyl group, an alkoxyalkyl group, a cyanoalkyl group, a sulfoalkyl group, a hydroxyalkyl group, a carboxyalkyl group, or an aminoalkyl group.

$R_1$ preferably represents a hydrogen atom, a mercapto group a halogen atom (e.g., fluorine, chlorine, bromine, iodine), an unsubstituted alkyl group having 18 or less carbon atoms (e g., methyl, ethyl, propyl), a substituted alkyl group (as the substituents, e.g., a halogen atom, an alkoxyl group, a cyano group, a sulfo group, a hydroxyl group, an acylamino group, an aryloxy group, and an alkyl group substituted with an arylamino group can be exemplified), an unsubstituted alkenyl group having 18 or less carbon atoms (e.g., vinyl, propenyl, butenyl, isopropenyl, isobutenyl), a substituted alkenyl group (as the substituents, e.g., a halogen atom, an alkoxyl group, a cyano group, a sulfo group, a hydroxyl group, an acylamino group, an aryloxy group, and an alkenyl group substituted with an arylamino group can be exemplified), an unsubstituted aryl group having 18 or less carbon atoms (e.g., phenyl, naphthyl), a substituted aryl group (as the substituents, e.g., a halogen atom, an alkoxyl group, a cyano group, a sulfo group, a hydroxyl group, an acylamino group, an aryloxy group, and an aryl group substituted with an arylamino group can be exemplified), an unsubstituted alkylthio group having 18 or less carbon atoms (e.g., methylthio, ethylthio, propylthio, butylthio, pentylthio), a substituted alkylthio group (as the substituents, e.g., a halogen atom, an alkoxyl group, a cyano group, a sulfo group, a hydroxyl group, an acylamino group, an aryloxy group, and an alkylthio group substituted with an arylamino group can be exemplified), an alkenylthio group having 18 or less carbon atoms (e.g., vinylthio, propenylthio, butenylthio), a substituted alkenylthio group (as the substituents, e.g., a halogen atom, an alkoxyl group, a cyano group, a sulfo group, a hydroxyl group, an acylamino group, an aryloxy group, and an alkenylthio group substituted with an arylamino group can be exemplified), an unsubstituted arylthio group having 18 or less carbon atoms (e.g., phenylthio, naphthylthio), or a substituted arylthio group (as the substituents, e.g., a halogen atom, an alkoxyl group, a cyano group, a sulfo group, a hydroxyl group, an acylamino group, an aryloxy group, and an arylthio group substituted with an arylamino group can be exemplified).

$R_1$ more preferably represents a hydrogen atom, a mercapto group, a halogen atom, an unsubstituted alkyl group having 8 or less carbon atoms (e.g., methyl, ethyl, propyl), an unsubstituted aryl group having 8 or less carbon atoms (e.g., phenyl, naphthyl), an unsubstituted alkylthio group having 8 or less carbon atoms (e.g., methylthio, ethylthio, propylthio, butylthio, pentylthio), or an unsubstituted arylthio group having 10 or less carbon atoms (e.g., phenylthio, naphthylthio).

$R_1$ particularly preferably represents a hydrogen atom, a mercapto group, a halogen atom, an unsubstituted alkyl group having 3 or less carbon atoms (e.g., methyl, ethyl, propyl), or an unsubstituted alkylthio group having 3 or less carbon atoms (e.g., methylthio, ethylthio, propylthio).

$L_1$ and $L_2$ each represents a methine group. The methine group represented by $L_1$ and $L_2$ may have a substituent, and examples of the substituents include a substituted or unsubstituted alkyl group having from 1 to 15, preferably from 1 to 10, and particularly preferably from 1 to 5, carbon atoms (e.g., methyl, ethyl, 2-carboxyethyl), a substituted or unsubstituted aryl group having from 6 to 20, preferably from 6 to 15, and more preferably from 6 to 10, carbon atoms (e.g., phenyl, o-carboxyphenyl), a substituted or unsubstituted heterocyclic group having from 3 to 20, preferably from 4 to 15, and more preferably from 6 to 10, carbon atoms (e.g., N,N-dimethylbarbitutic acid radical), a halogen atom (e.g., chlorine, bromine, iodine, fluorine,), an alkoxyl group having from 1 to 15, preferably from 1 to 10, and more preferably from 1 to 5, carbon atoms (e.g., methoxy, ethoxy), an amino group having from 0 to 15, preferably from 2 to 10, and more preferably from 4 to 10, carbon atoms (e.g., methylamino, N,N-dimethylamino, N-methyl-N-phenylamino, N-methylpiperadino), an alkylthio group having from 1 to 15, preferably from 1 to 10, and more preferably from 1 to 5, carbon atoms (e.g., methylthio, ethylthio), and an arylthio group having from 6 to 20, preferably from 6 to 12, and more preferably from 6 to 10, carbon atoms (e.g., phenylthio, p-methylphenylthio). The methine group represented by $L_1$ and $L_2$ may form a ring together with other methine groups or can form a ring with an auxochrome.

$p_1$ represents 0 or 1 preferably 0.

$R_2$ represents a substituted or unsubstituted alkyl group or a substituted or unsubstituted aryl group, and those described in the definition of V can be exemplified as the examples of the substituents. As the alkyl group, e.g., an unsubstituted alkyl group having from 1 to 18, preferably from 1 to 7, and more preferably from 1 to 4, carbon atoms (e.g., methyl, ethyl, propyl, isopropyl, butyl, isobutyl, hexyl, octyl, dodecyl, octadecyl), an aralkyl group (e.g., benzyl, 2-henylethyl, naphthylmethyl, 2-(4-biphenyl)ethyl), unsaturated hydrocarbon group (e.g., allyl, crotyl), a hydroxyalkyl group (e.g., 2-hydroxyethyl, 3-hydroxypropyl), an alkoxyalkyl group (e.g., 2-methoxyethyl, 2-(2-methoxyethoxy)ethyl), an aryloxyalkyl group (e.g., 2-phenoxyethyl, 2-(1-naphthoxy)ethyl, 2-(4-biphenyloxy)ethyl, 2-(o, m, p-halophenoxy)ethyl, 2-(o, m, p-methoxyphenoxy)ethyl), an alkoxycarbonylalkyl group (e.g., ethoxycarbonylethyl, 2-benzyloxycarbonylethyl), an aryloxycarbonylalkyl group (e.g., 3-phenoxycarbonylpropyl, 2-(1-naphthoxycarbonyl) ethyl), an acyloxyalkyl group (e.g., 2-acetyloxyethyl), an acylalkyl group (e.g., 2-acetylethyl), a carbamoylalkyl group (e.g., 2-morpholinocarbonylethyl), a sulfamoylalkyl group (e.g., N,N-dimethylsulfamoylmethyl), and a heterocyclic alkyl group (e.g., 2-(pyrrolidine-2-one-1-yl)ethyl) can be exemplified. $R_2$ preferably represents an alkyl group having an aryl group or a heterocyclic group as a substituent, an aryl group, or a heterocyclic group.

$M_1$ is included in the formula to show the presence or absence of a cation or an anion when a counter ion is necessary for neutralizing the ionic charge in the molecule of the compound. Examples of representative cations include a hydrogen ion ($H^+$) an inorganic-ion such as an alkali metal ion (e.g., a sodium ion, a potassium ion, a lithium ion), and an alkaline earth metal ion (e.g., a calcium ion), and an organic ion such as an ammonium ion (e.g., an ammonium ion, a tetraalkylammonium ion, a pyridinium ion, an ethylpyridinium ion). Anions may be either inorganic or organic anions, e.g., a halogen anion (e.g., a fluorine ion, a chlorine ion, a bromine ion, an iodine ion), a substituted arylsulfonate ion (e.g., a p-toluenesulfonate ion, a p-chlorobenzenesulfonate ion), an aryldisulfonate ion (e.g., a 1,3-benzenedisulfonate ion, a 1,5-naphthalenedisulfonate ion, a 2,6-naphthalenedsulfonate ion), an alkylsulfate ion (e.g., a methylsulfate ion), a sulfate ion, a thiocyanate ion, a perchlorate ion, a tetrafluoroborate ion, a picrate ion, an acetate ion, and a trifluoromethanesulfonate ion can be exemplified. Further, ionic polymers or molecules having a counter charge against the molecules can also be used $m_1$ represents a number necessary to neutralize the electric charge of the molecule. When inner salt is formed, $m_1$ represents 0.

Any methine dye can be formed by $Q_1$ but preferred are a cyanine dye, a merocyanine dye, a rhodacyanine dye, a trinuclear merocyanine dye, a holopolar dye, a hemicyanine dye, a styryl dye, etc. These dyes are described in detail in F. M. Harmer, *Heterocyclic Compounds—Cyanine Dyes and Related Compounds*, John Wiley & Sons, New York, London (1964), D. M. Sturmer, *Heterocyclic Compounds—Special Topics in Heterocyclic Chemistry*, Chap. 18, Clause 14, pp 482 to 515, John Wiley-& Sons, New York, London (1977), etc.

Formulae (XI), (XII) and (XIII) disclosed in U.S. Pat. No. 5,340,694, pp. 21 and 22 are preferred as formulae of the cyanine, merocyanine and rhodacyanine dyes, respectively.

Further, when a cyanine dye is formed by Q in formula (III), it can be represented by the following resonance formula:

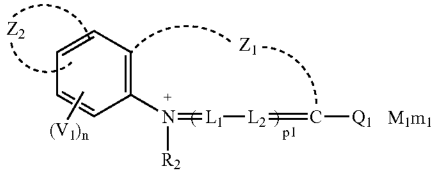

The number of the methine group in $Q_1$ is preferably from 0 to 7, more preferably from 0 to 5, and particularly preferably 3. When $Q_1$ is to form the above-described dyes (a cyanine dye, a merocyanine dye, a rhodacyanine dye, a trinuclear merocyanine dye, a holopolar dye, a hemicyanine dye, a styryl dye, etc.), the number of the methine group in $Q_1$ may be 0 (e.g., simple merocyanine) It is preferred that the methine group is substituted with a substituent necessary to form a methine dye (e.g., a heterocyclic group, an aliphatic group, or an aromatic group). The preferred substituent is a heterocyclic group or an aromatic group, and particularly preferred is an aromatic group. As the examples of the heterocyclic groups, those described as the examples of $Z_1$ are preferred.

As the examples of the aromatic groups, substituted or unsubstituted aromatic groups (e.g., 4-dimethylaminophenyl, 4-methoxyphenyl, phenyl; 4-dimethylaminonaphthyl) can be exemplified.

As the aliphatic groups, an alkoxycarbonyl group (e.g., ethoxycarbonyl) and an acyl group (e.g., acetyl) can be preferred. In addition to the above, substituents described in V above can be exemplified, and a substituted or unsubstituted amino group (e.g., amino, dimethylamino), a cyano group, an alkoxycarbonyl group (e.g., ethoxycarbonyl), a substituted or unsubstituted alkylsulfonyl group (e.g., methylsulfonyl), and a substituted or unsubstituted acyl group (e.g., acetyl) are preferably used.

Specific examples of the compounds represented by formula (I) (including formulae (IV) and (V) of subordinate concept) according to the present invention are shown below but it should not be construed as the present invention is limited thereto.

I-1

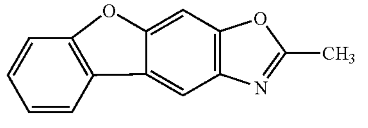

I-2

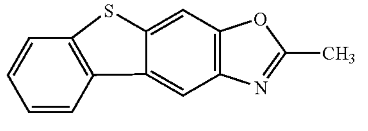

I-3

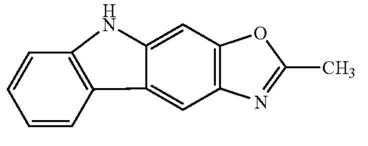

-continued
I-4
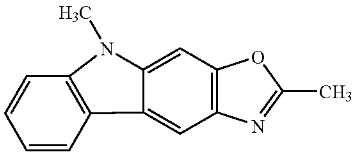
I-5
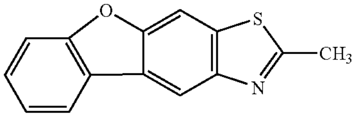
I-6
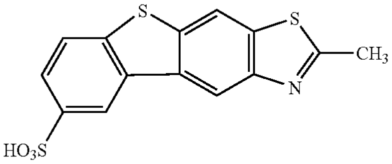
I-7
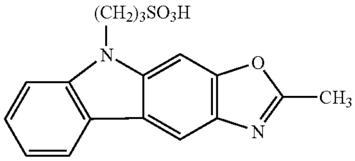
I-8
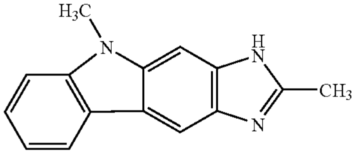
I-9
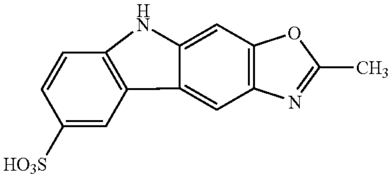
I-10
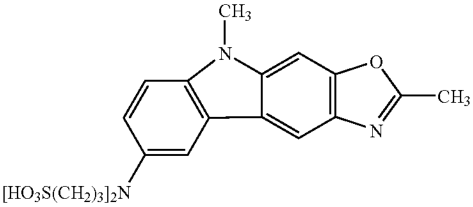
I-11
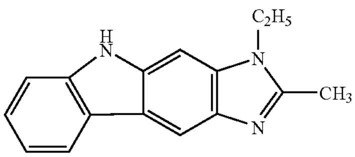
I-12
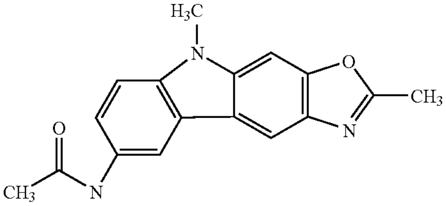
-continued
I-13
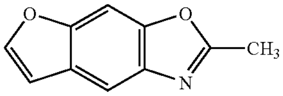
I-14
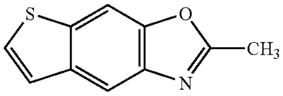
I-15
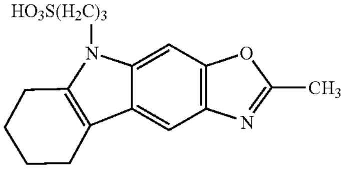
I-16
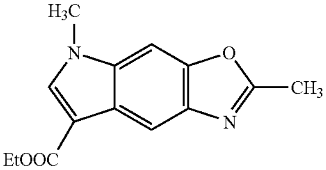
I-17
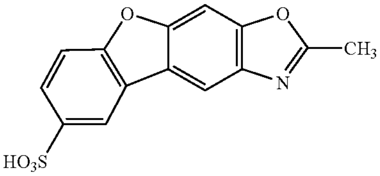
I-18
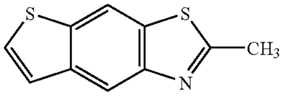
I-19
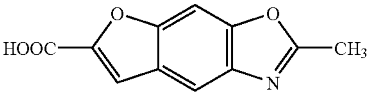
I-20
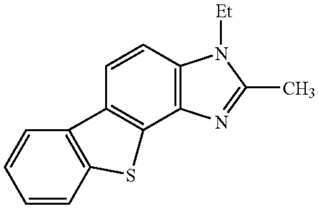
I-21
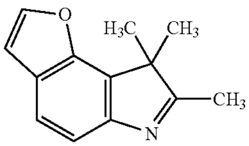
I-22
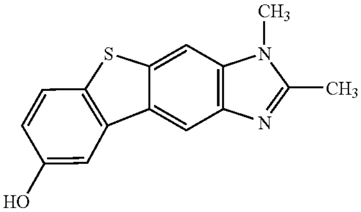

-continued
I-23
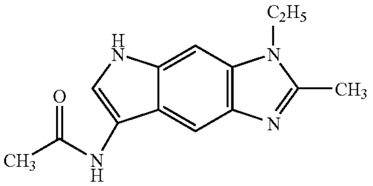
I-24
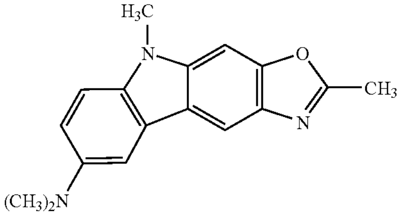
I-25
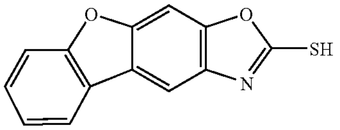
I-26
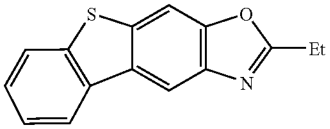
I-27
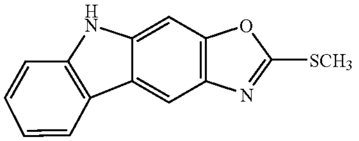
I-28
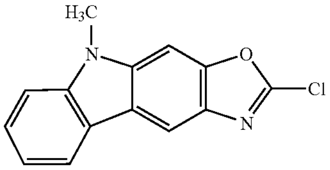
I-29
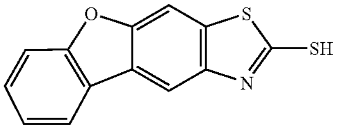
I-30
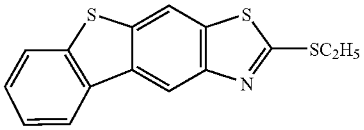
I-31
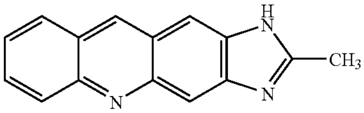
I-32
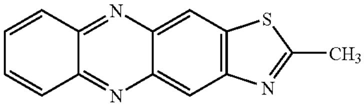
-continued
I-33
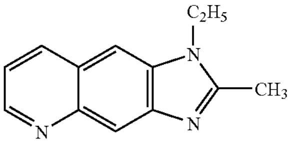
I-34
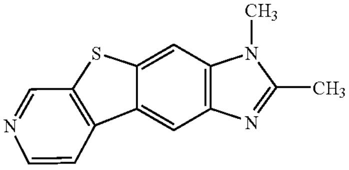
I-35
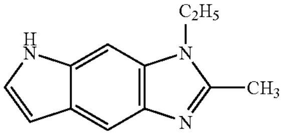
I-36
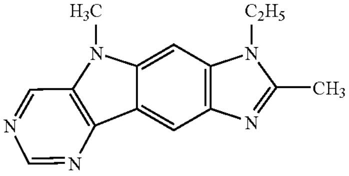
I-37
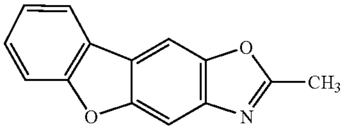
I-38
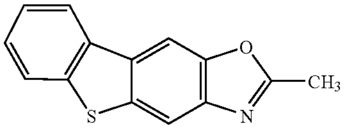
I-39
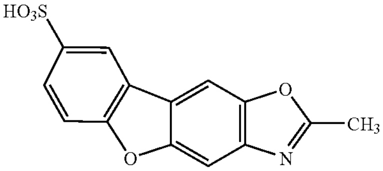
I-40
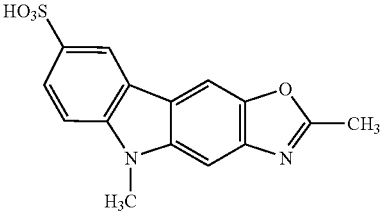
I-41
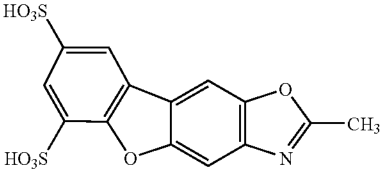

-continued
I-42
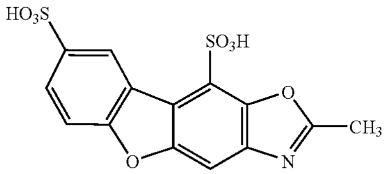
I-43
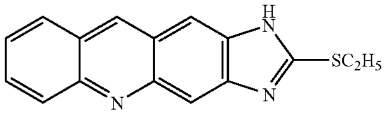
I-44
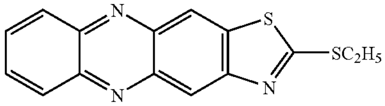
I-45
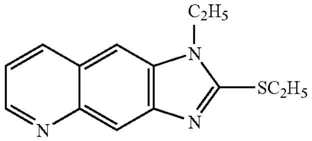
I-46
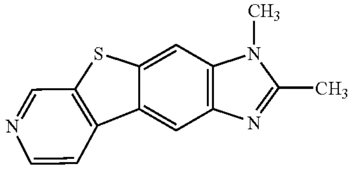
I-47
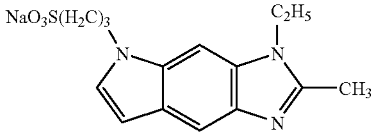
I-48
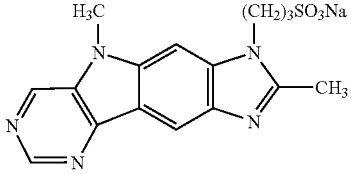
Specific examples of the compounds represented by formula (II) (including formulae (VI) and (VII) of subordinate concept) according to the present invention are shown below but it should not be construed as the present invention is limited thereto.
II-1
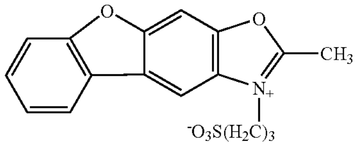
II-2
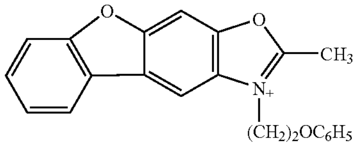
-continued
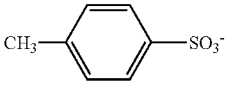
II-3
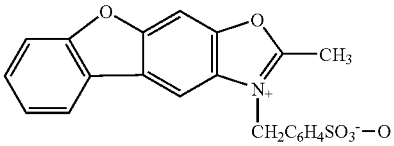
II-4
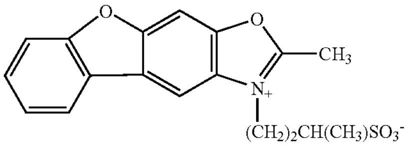
II-5
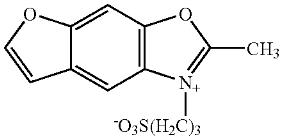
II-6
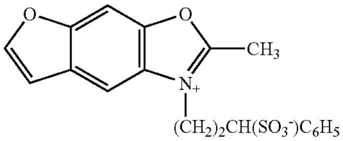
II-7
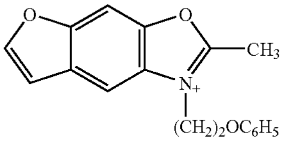
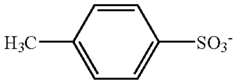
II-8
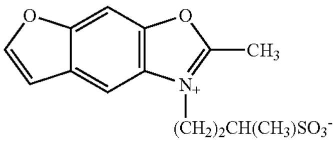
II-9
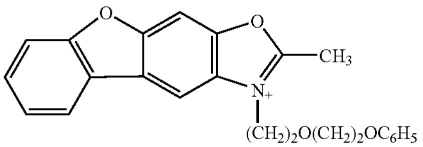
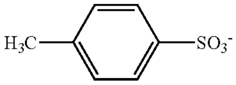
II-10
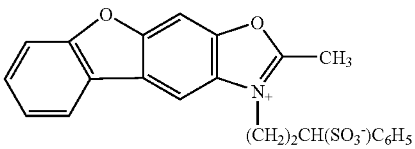

-continued
II-11
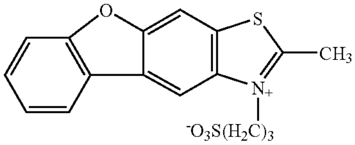
II-12
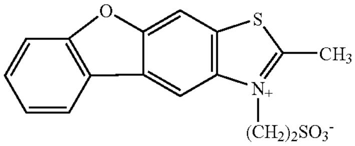
II-13
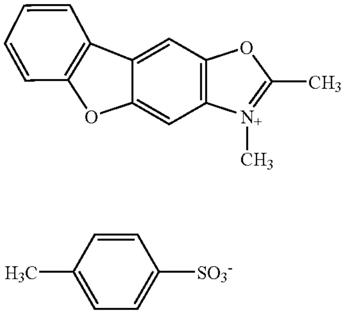
II-14
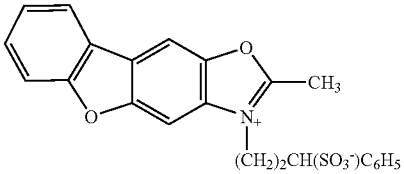
II-15
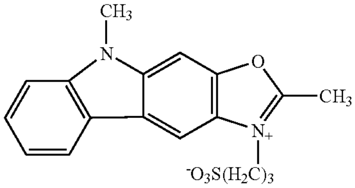
II-16
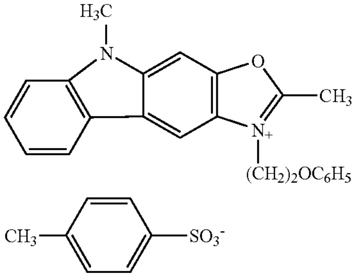
II-17
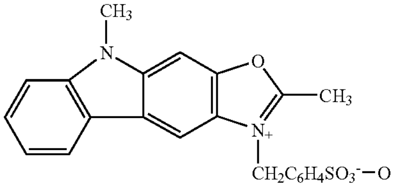
-continued
II-18
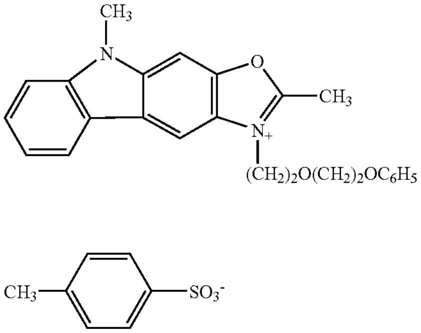
II-19
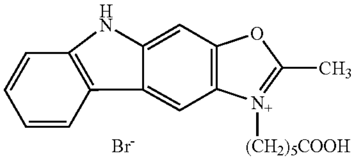
II-20
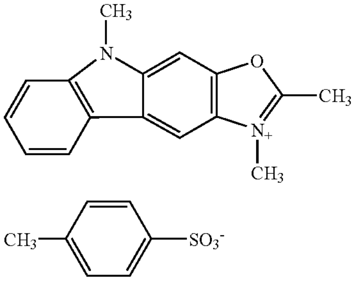
II-21
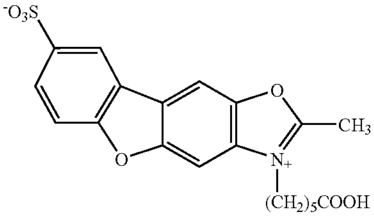
II-22
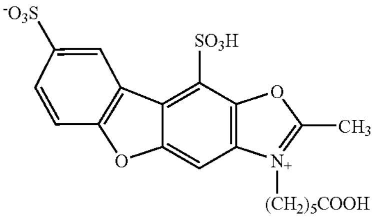
II-23
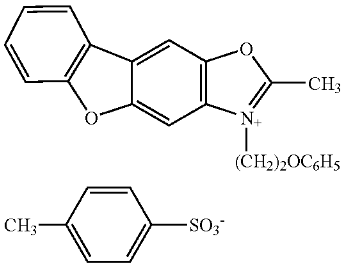

-continued
II-24
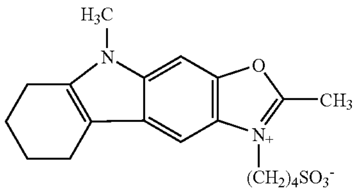
II-25
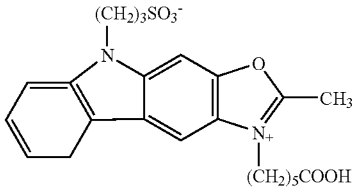
II-26
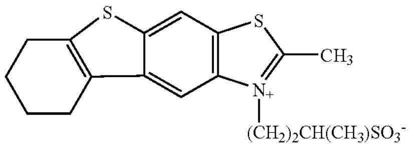
II-27
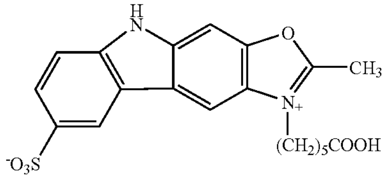
II-28
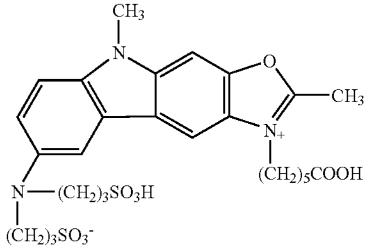
II-29
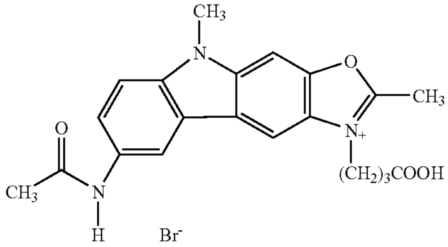
II-30
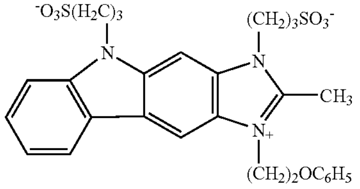
-continued
II-31
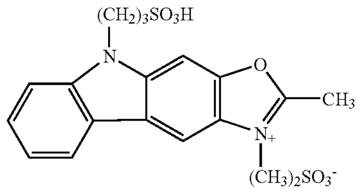
II-32
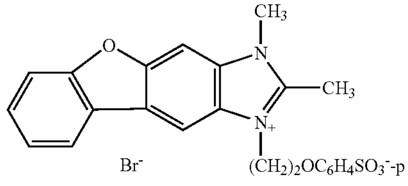
II-33
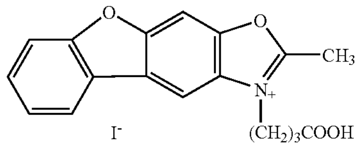
II-34
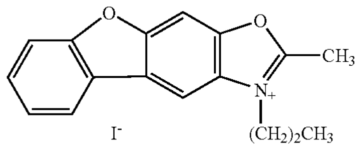
II-35
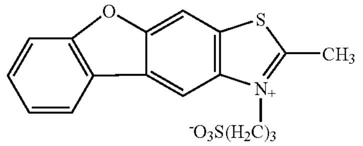
II-36
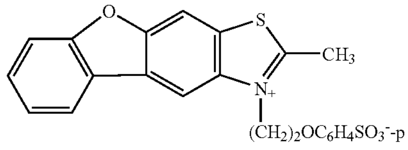
II-37
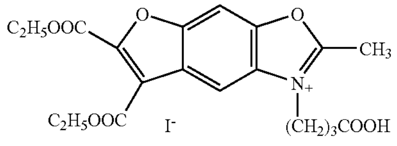
II-38
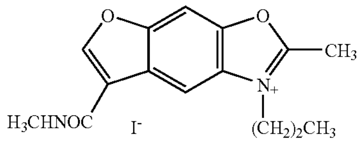
II-39
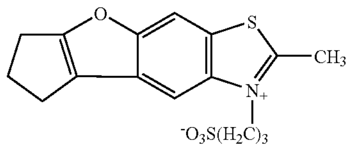

-continued
II-40
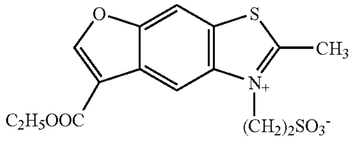
II-41
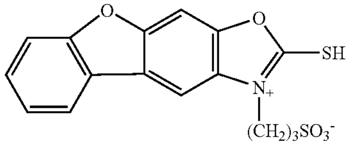
II-42
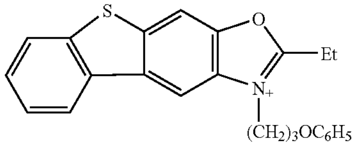
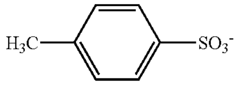
II-43
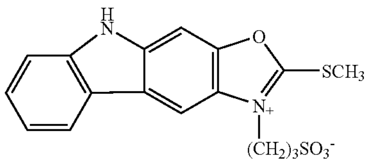
II-44
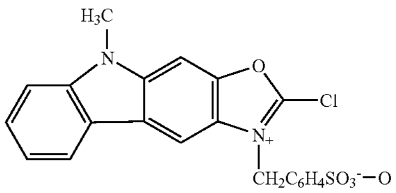
II-45
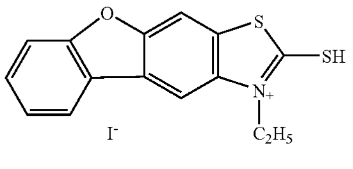
II-46
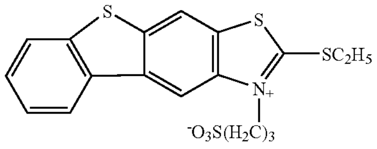
II-47
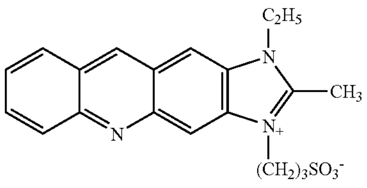
-continued
II-48
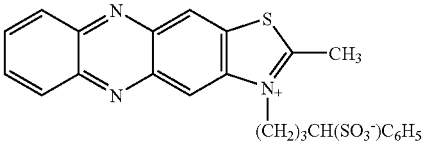
II-49
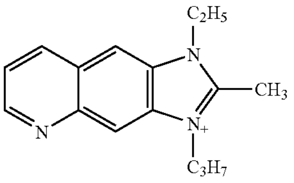
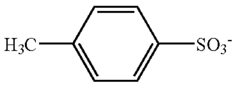
II-50
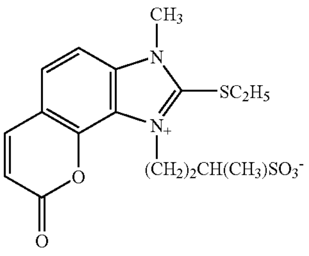
II-51
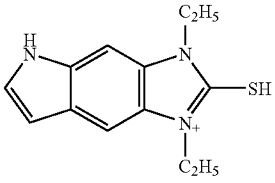
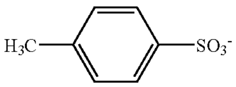
II-52
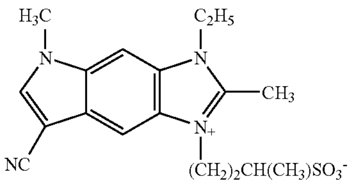
Specific examples of the compounds represented by formula (III) (including formulae (VIII) and (IX) of subordinate concept) according to the present invention are shown below but it should not be construed as the present invention is limited thereto.

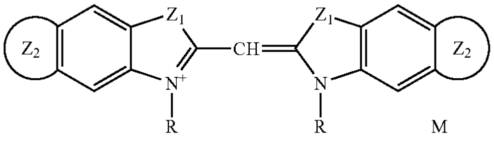

| No. | $Z_1$ | $Z_2$ | R | M |
|---|---|---|---|---|
| III-1 | S | 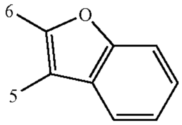 | $(CH_2)_2OC_6H_5$ | $p\text{-}CH_3C_6H_4SO_3^-$ |
| III-2 | S | " | $CH_2C_6H_4SO_3^-\text{-}p$ | $HN^+(C_2H_5)_3$ |
| III-3 | S | " | $(CH_2)_4SO_3^-$ | $HN^+(C_2H_5)_3$ |
| III-4 | S | 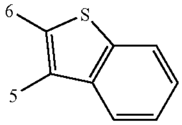 | $(CH_2)_2OC_6H_5$ | $p\text{-}CH_3C_6H_4SO_3^-$ |
| III-5 | S | 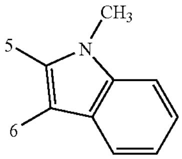 | $(CH_2)_3SO_3^-$ | $HN^+(C_2H_5)_3$ |
| III-6 | S | 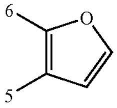 | $(CH_2)_2CH(SO_3^-)Ph$ | $HN^+(C_2H_5)_3$ |
| III-7 | S | " | $(CH_2)_2OC_6H_4Br$ | $p\text{-}CH_3C_6H_4SO_3^-$ |
| III-8 | S | 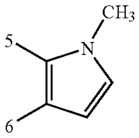 | $(CH_2)_2OC_6H_5$ | $p\text{-}CH_3C_6H_4SO_3^-$ |
| III-9 | S | 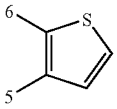 | $(CH_2)_2OC_6H_5$ | $p\text{-}CH_3C_6H_4SO_3^-$ |
| III-10 | S | 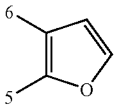 | $(CH_2)_2OC_6H_4C_6H_5\text{-}p$ | $p\text{-}CH_3C_6H_4SO_3^-$ |
| III-11 | S | " | $(CH_2)_2OC_6H_5$ | $p\text{-}CH_3C_6H_4SO_3^-$ |
| III-12 | O | 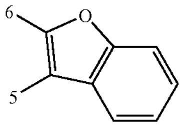 | $CH_2C_6H_4SO_3^-\text{-}p$ | $HN^+(C_2H_5)_3$ |
| III-13 | O | " | $(CH_2)_3OC_6H_5$ | $p\text{-}CH_3C_6H_4SO_4^-$ |

-continued

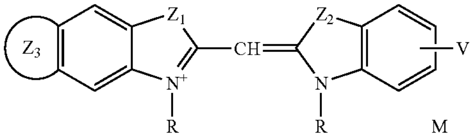

| No. | $Z_1$ | $Z_3$ | $Z_2$ | V | R | M |
|---|---|---|---|---|---|---|
| III-14 | S | 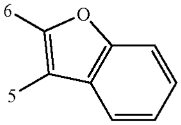 | S | 5-Cl | $(CH_2)_2OC_6H_5$ | $p\text{-}CH_3C_6H_4SO_3^-$ |
| III-15 | S | " | S | 5-Ph | $(CH_2)_2CH(SO_3^-)Ph$ | $Na^+$ |
| III-16 | S | " | S | 5-(2-Thienyl) | $(CH_2)_3OC_6H_5$ | $p\text{-}CH_3C_6H_4SO_3^-$ |
| III-17 | S | 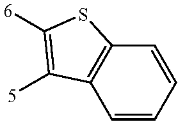 | S | 5-(2-Furyl) | $(CH_2)_2OC_6H_4OCH_3\text{-}p$ | $p\text{-}CH_3C_6H_4SO_3^-$ |
| III-18 | S | 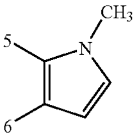 | S | 5-Ph | $(CH_2)_2OC_6H_4OCH_3\text{-}p$ | $p\text{-}CH_3C_6H_4SO_3^-$ |
| III-19 | O | 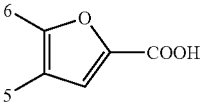 | S | 4,5-Benzo | $(CH_2)_2OC_6H_5$ | $p\text{-}CH_3C_6H_4SO_3^-$ |
| III-20 | O | 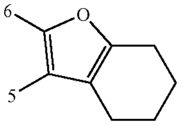 | S | 5-Cl | $(CH_2)_2OC_6H_5$ | $p\text{-}CH_3C_6H_4SO_3^-$ |
| III-21 | O | 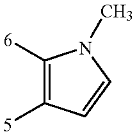 | O | $5\text{-}OCH_3$ | $(CH_2)_3SO_3^-$ | $Na^+$ |
| III-22 | O | 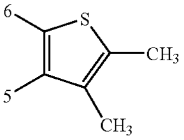 | O | 5-Cl | $(CH_2)_2OC_6H_4OCH_3\text{-}p$ | $Br^-$ |
| III-23 | S | 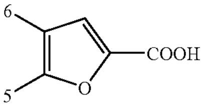 | O | 5-Ph | $(CH_2)_2OC_6H_4OCH_3\text{-}p$ | $Br^-$ |
| III-24 | S | 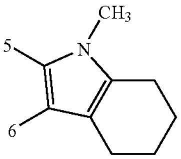 | S | 5-Ph | $(CH_2)_2C_6H_6$ | $p\text{-}CH_3C_6H_4SO_3^-$ |

-continued

| | | | | | | |
|---|---|---|---|---|---|---|
| III-25 | O | 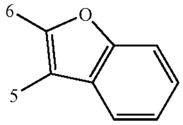 | S | 4,5-Benzo | $CH_2C_6H_4SO_3^-$—O | $HN^+(C_2H_5)_3$ |
| III-26 | O | " | O | 5-Ph | $(CH_2)_3CH(CH_3)SO_3^-$ | $Na^+$ |

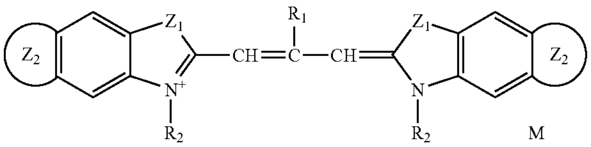

| No. | $Z_1$ | $Z_2$ | $R_1$ | $R_2$ | M |
|---|---|---|---|---|---|
| III-27 | S | 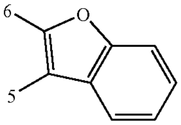 | $C_2H_5$ | $(CH_2)_3OC_6H_5$ | $p\text{-}CH_3C_6H_4SO_3^-$ |
| III-28 | S | " | $C_2H_5$ | $CH_2C_6H_4SO_3^-$—O | $Na^+$ |
| III-29 | S | " | $C_2H_5$ | $(CH_2)_2OC_6H_5$ | $Br^-$ |
| III-30 | S | 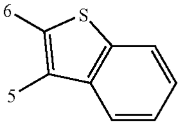 | $C_2H_5$ | $(CH_2)_2OC_6H_5$ | $p\text{-}CH_3C_6H_4SO_3^-$ |
| III-31 | S | 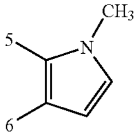 | $C_2H_5$ | $(CH_2)_2OC_6H_5$ | $p\text{-}CH_3C_6H_4SO_3^-$ |
| III-32 | S | 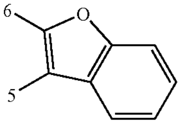 | $C_2H_5$ | $(CH_2)_2O(CH_2)_2OPh$ | $p\text{-}CH_3C_6H_4SO_3^-$ |
| III-33 | S | " | $C_2H_5$ | $(CH_2)_2CH(SO_3^-)Ph$ | $HN^+(C_2H_5)_3$ |
| III-34 | S | 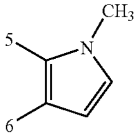 | $C_2H_5$ | $CH_2C_6H_4SO_3^-$—O | $HN^+(C_2H_5)_3$ |
| III-35 | S | 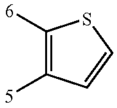 | $C_2H_5$ | $(CH_2)_2OC_6H_5$ | $p\text{-}CH_3C_6H_4SO_3^-$ |
| III-36 | S | 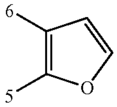 | H | $(CH_2)_3SO_3^-$ | $HN^+(C_2H_5)_3$ |

-continued

| | | | | | |
|---|---|---|---|---|---|
| III-37 | S | " | H | $(CH_2)_5COOH$ | $Br^-$ |
| III-38 | S | 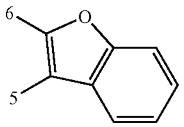 | $CH_3$ | $(CH_2)_2OC_6H_5$ | $Br^-$ |
| III-39 | S | " | $CH_3$ | $(CH_2)_2OC_6H_4C_6H_5$-p | p-$ClC_6H_4SO_3^-$ |
| III-40 | O | " | $C_2H_5$ | $CH_2C_6H_4SO_3^-$—O | $HN^+(C_2H_5)_3$ |
| III-41 | O | " | $C_2H_5$ | $(CH_2)_2OC_6H_5$ | p-$CH_3C_6H_4SO_3^-$ |
| III-42 | O | " | $C_2H_5$ | $(CH_2)_2OC_6H_4OCH_3$-p | p-$ClC_6H_4SO_3^-$ |
| III-43 | O | 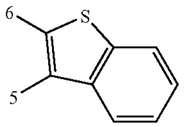 | $C_2H_5$ | $(CH_2)_4SO_3^-$ | $HN^+(C_2H_5)_3$ |
| III-44 | | 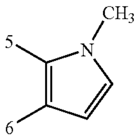 | $C_2H_5$ | $(CH_2)_4SO_3^-$ | $HN^+(C_2H_5)_3$ |
| III-45 | O | 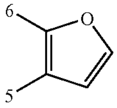 | $C_2H_5$ | $(CH_2)_2OC_6H_4C_6H_5$-p | p-$ClC_6H_4SO_3^-$ |
| III-46 | O | " | H | $(CH_2)_3COOH$ | $Br^-$ |
| III-47 | O | 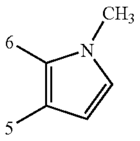 | $C_2H_5$ | $(CH_2)_2C_6H_5$ | p-$CH_3C_6H_4SO_3^-$ |
| III-48 | O | 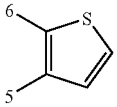 | $C_2H_5$ | $(CH_2)_2OC_6H_5$ | p-$CH_3C_6H_4SO_3^-$ |
| III-49 | O | 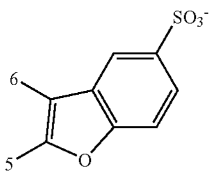 | $C_2H_5$ | $(CH_2)_3SO_3^-$ | $3Na^+$ |
| III-50 | O | " | $C_2H_5$ | $(CH_2)_2OC_6H_4OCH_3$-p | p-$CH_3C_6H_4SO_3^-$ |
| III-51 | O | 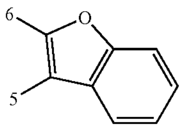 | $C_2H_5$ | $(CH_2)_3SO_3^-$ | $HN^+(C_2H_5)_3$ |

-continued

| | | | | | |
|---|---|---|---|---|---|
| III-52 | O | " | $CH_3$ | $(CH_2)_2OC_6H_4C_6H_5$-p | p-$ClC_6H_4SO_3^-$ |

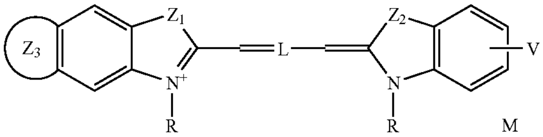

| No. | $Z_1$ | $Z_3$ | $Z_2$ | V | L | R | M |
|---|---|---|---|---|---|---|---|
| III-53 | S | 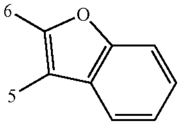 | S | 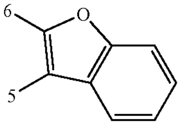 | $=CH—CH=CH—$ | $(CH_2)_2OC_6H_5$ | p-$CH_3C_6H_4SO_3^-$ |
| III-54 | O | " | O | " | 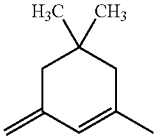 | $(CH_2)_3SO_3^-$ | $HN^+(C_2H_5)_3$ |
| III-55 | O | " | O | 5-Ph | " | $(CH_2)_2OC_6H_4OCH_3$-p | p-$CH_3C_6H_4SO_3^-$ |
| III-56 | O | 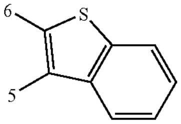 | O | 5-(2-Furyl) | $=CH—CH=CH—$ | $(CH_2)_2OC_6H_5$ | p-$CH_3C_6H_4SO_3^-$ |
| III-57 | O | 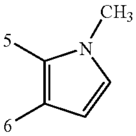 | O | 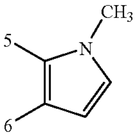 | 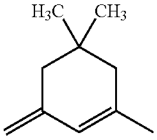 | $CH_2C_6H_4SO_3^-—O$ | $HN^+(C_2H_5)_3$ |
| III-58 | O | 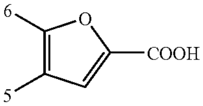 | O | 4,5-Benzo | 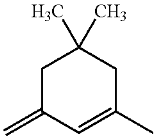 | $(CH_2)_2CH(SO_3^-)Ph$ | $HN^+(C_2H_5)_3$ |
| III-59 | O | 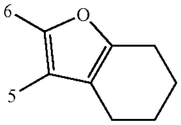 | O | 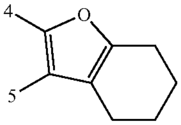 | " | $(CH_2)_2OC_6H_5$ | p-$CH_3C_6H_4SO_3^-$ |
| III-60 | O | 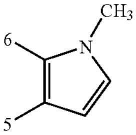 | O | 5-$OCH_3$ | " | $(CH_2)_2OC_6H_4C_6H_5$-p | p-$ClC_6H_4SO_3^-$ |
| III-61 | O | 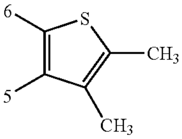 | O | 5-Cl | $=CH—CH=CH—$ | $(CH_2)_2OC_6H_5$ | p-$CH_3C_6H_4SO_3^-$ |
| III-62 | S | 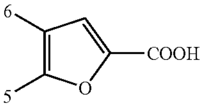 | O | 5-Ph | $=CH—CH=CH—$ | $(CH_2)_4SO_3^-$ | $Na^+$ |

-continued
| | | | | | | | |
|---|---|---|---|---|---|---|---|
| III-63 | S | 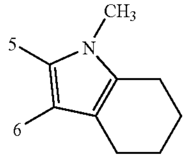 | S | 5-Ph | 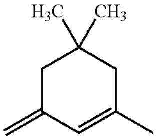 | $(CH_2)_2SO_3^-$ | $Na^+$ |
| III-64 | O | 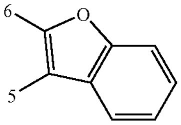 | S | 4,5-Benzo | " | $(CH_2)_2SO_3^-$ | $Na^+$ |
| III-65 | O | " | O | 5-Ph | " | $(CH_2)_2SO_3^-$ | $Na^+$ |
III-66
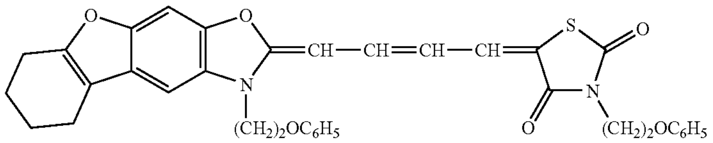
III-67
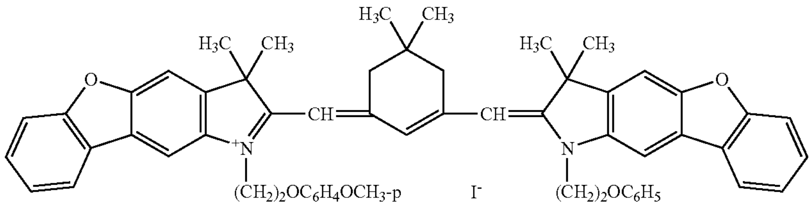
III-68
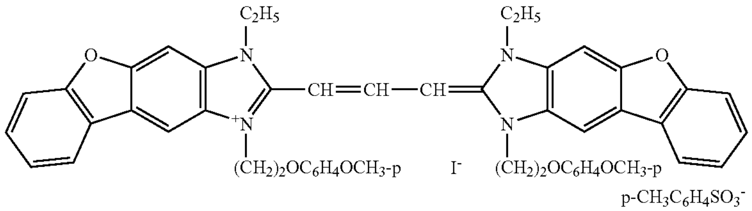
III-69
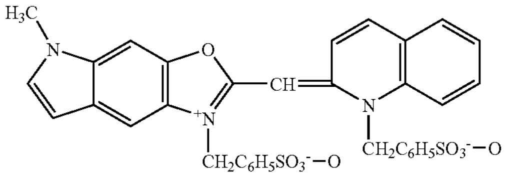
III-70
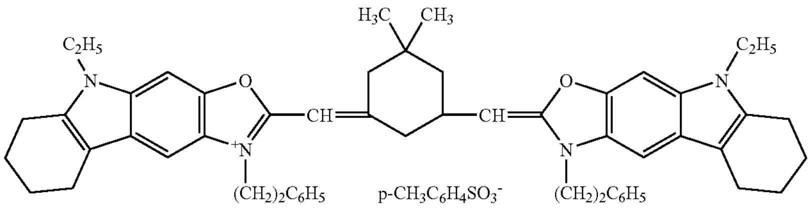

-continued
III-71
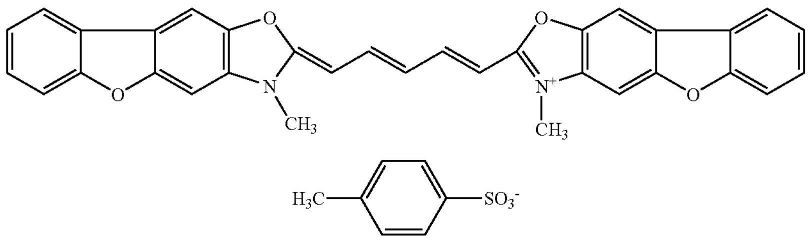
III-72
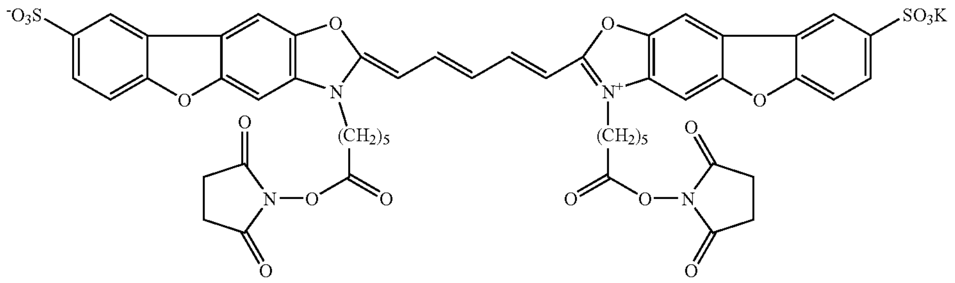
III-73
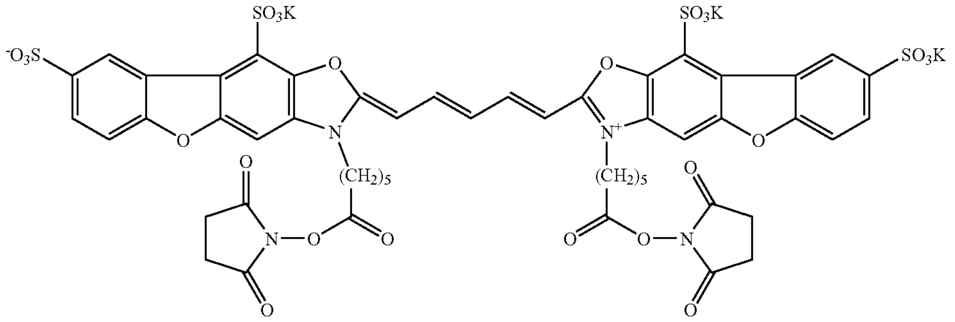
III-74
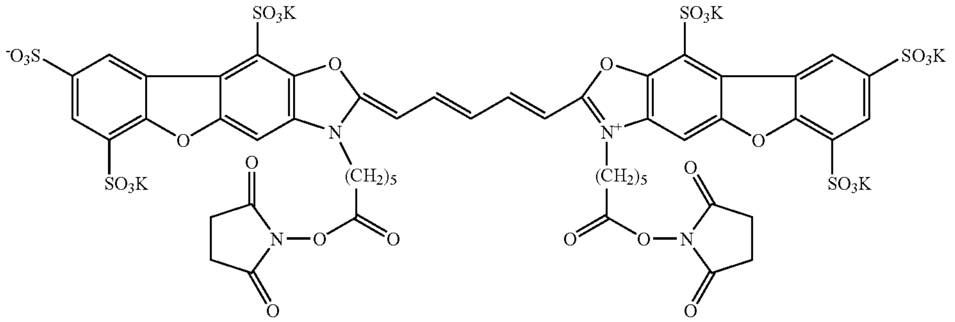
III-75
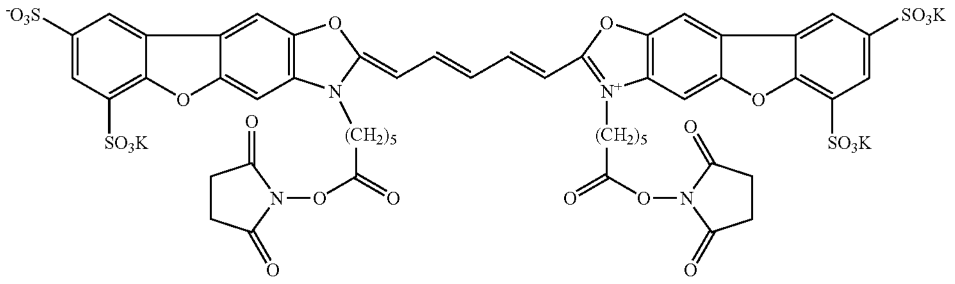

-continued
III-76
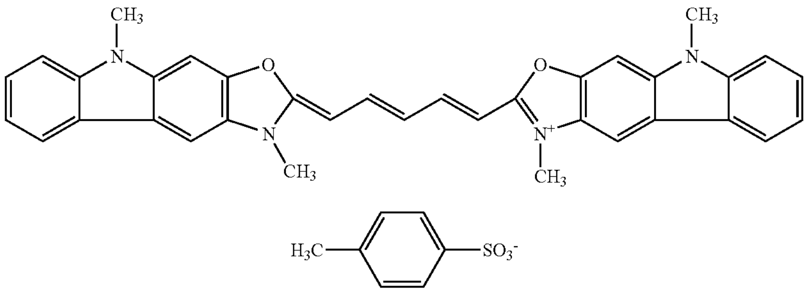
III-77
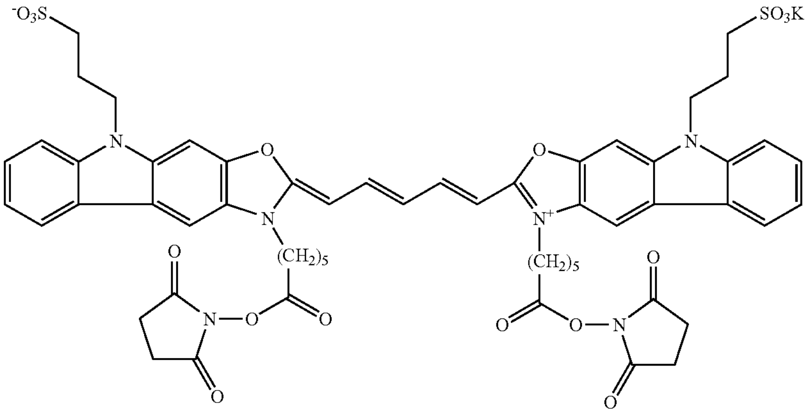
III-78
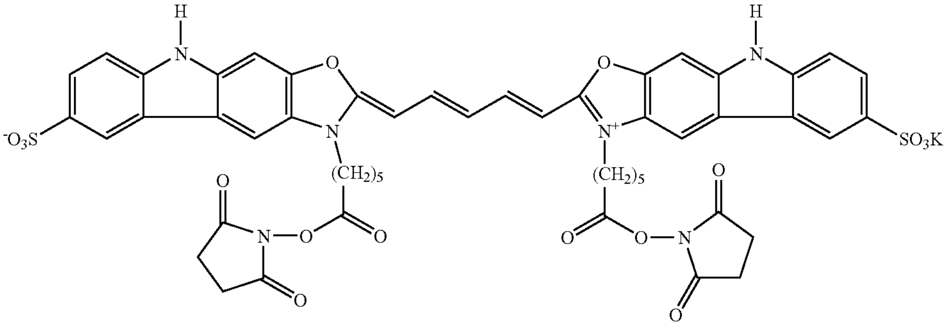
III-79
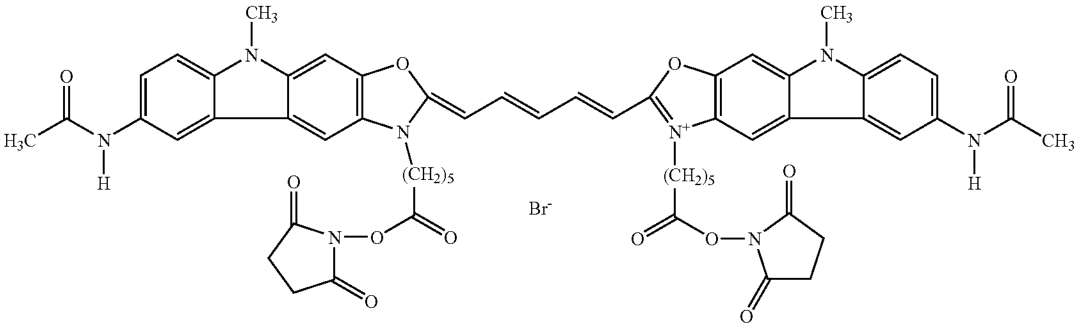

-continued

III-80

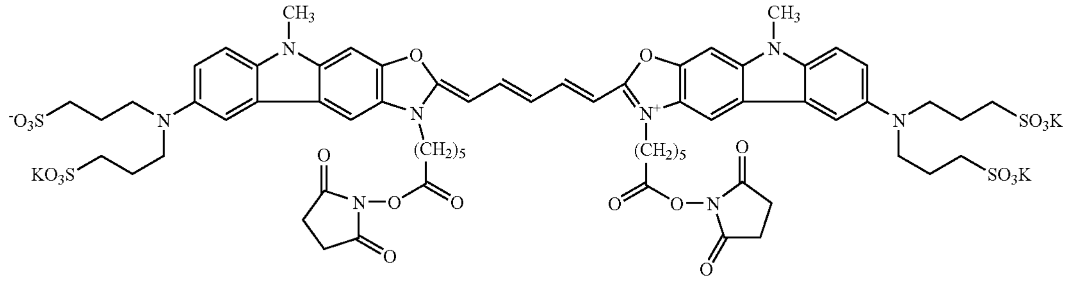

The compounds represented by formulae (I), (II) and (III) (including formulae (IV) to (IX) of subordinate concept) according to the present invention can be synthesized by referring to the compounds described in F. M. Harmer, *Heterocyclic Compounds—Cyanine Dyes and Related Compounds*, John Wiley & Sons, New York, London (1964), D. M. Sturmer, *Heterocyclic Compounds—Special Topics in Heterocyclic Chemistry*, Chap. 18, Clause 14, pp. 482 to 515, John Wiley & Sons, New York, London, (1977), and *Rodd's Chemistry of Carbon Compounds*, 2nd Ed., Vol. IV, Part B, Chep. 15, pp. 369 to 422, Elsevier Science Publishing Company Inc., New York (1977), etc.

The use of methine dyes is not particularly limited. Methine dyes are useful as a coloring agent, a light absorber, a dye for an optical disc, spectral sensitizing dyes for a silver halide photograph and an electrophotograph, or a marker for diagnosis. For example, methine dyes can-be excited with an inexpensive helium-neon laser light source (633 nm), and the fluorescent intensity of methine dyes is stronger than that of the conventionally used dyes, hence extremely useful as the marker of various substances. The substances which can be marked with the methine dye according to the present invention are not particularly restricted and, for example, antibody, protein, peptide, enzyme substrate, hormone, lymphokine, metabolite, receptor, antigen, hapten, lectin, avidin, streptavidin, toxine, carbohydrate, polysaccharide, nucleic acid, deoxy nucleic acid, derived nucleic acid, derived deoxy nucleic acid, DNA fragment, RNA fragment, derived DNA fragment, derived RNA fragment, natural medicine, virus corpuscle, bacteria corpuscle, virus component, yeast component, blood cell, blood cell component, bacteria, bacteria component, natural or synthetic lipid, synthetic medicine, poisonous medicine, environmental pollutional substance, polymer, polymer particle, glass particle, plastic particle, and polymer film can be exemplified.

The silver halide photographic emulsion and the silver halide photographic material according to the present invention will be described in detail below.

In the present invention, light absorption strength means the light absorptive a real strength per a unit surface area of a grain by a sensitizing dye, and is defined as the value obtained by integrating optical density Log $(I_0/(I_0-I))$ to wavelength ($cm^{-1}$), when the light amount to be incident on the unit surface area of a grain is taken as $I_0$ and the light amount to be absorbed by a sensitizing dye on the surface is taken as I. The coverage of integration is from 5,000 $cm^{-1}$ to 35,000 $cm^{-1}$.

It is preferred for the silver halide photographic emulsion according to the present invention to contain silver halide grains having the light absorption strength of 100 or more in the proportion of 1/2 or more of the entire projected area of silver halide grains when the spectral absorption maximum wavelength exceeds 500 nm, and silver halide grains having the light absorption strength of 60 or more in the proportion of 1/2 or more of the entire projected area of silver halide grains when the spectral absorption maximum wavelength is 500 nm or less. Further, when the spectral absorption maximum wavelength of the grain exceeds 500 nm, the light absorption strength is preferably 150 or more, more preferably 170 or more, and particularly preferably 200 or more, and when the spectral absorption maximum wavelength is 500 nm or less, the light absorption strength is preferably 90 or more, more preferably 100 or more, and particularly preferably 120 or more. The upper limit of the light absorption strength is not particularly restricted but is preferably 2,000 or less, more preferably 1,000 or less, and particularly preferably 500 or less.

With respect to the grains having the spectral absorption maximum wavelength of 500 nm or more, the spectral absorption maximum wavelength is preferably 350 nm or more.

As one example of measuring the light absorption strength, a method of using a microspectrophotometer can be exemplified. A microspectrophotometer is an apparatus capable of measuring the absorption spectrum of a minute area, and it is possible to measure the transmission spectrum of one grain. Regarding the measurement of the absorption spectrum of one grain by a microspectral method, Yamashita et al., *The Substances of the Lectures in Annual Meeting in* 1996, Nihon Shashin Gakkai, p. 15 can be referred to. The absorption strength per one grain can be obtained from the absorption spectrum. As the light which transmits a grain is absorbed at two planes of an upper plane and a lower plane, the light absorption strength per a unit area of a grain surface can be obtained as 1/2 of the absorption strength per one grain obtained by the above method. The coverage of the integration of absorption spectrum is from 5,000 $cm^{-1}$ to 35,000 $cm^{-1}$ in the definition of light absorption strength, but in view of experiment the coverage of the integration may be the coverage including 500 $cm^{-1}$ before and behind the region where a sensitizing dye has absorption.

The light absorption strength can also be found by measuring transmission spectrum by juxtaposing grains not overlapping each other but closely without using the microspectral method.

The light absorption strength is a value determined univocally by the ad-molecule number per a unit area and the oscillator strength of a sensitizing dye, hence the light absorption strength is convertible from the oscillator strength of a sensitizing dye, the adsorption amount of a dye and the surface area of a grain.

As the oscillator strength of a sensitizing dye can be obtained experimentally as a value proportional to the absorption area strength of a sensitizing dye solution (optical density×$cm^{-1}$), the light absorption strength can be obtained according to the following equation within the errors-of about 10% with taking the absorption area strength of a sensitizing dye per 1 M as A (optical density×$cm^{-1}$) the adsorption amount of a sensitizing dye as B (mol/mol Ag), and the surface area of a grain as C ($m^2$/mol Ag):

$$0.156\times A\times B/C$$

The light absorption strength found from the above equation is substantially the same as the value obtained by integrating the light absorption strength measured according to the above definition [Log ($I_0/(I_0-I)$)] to wavelength ($cm^{-1}$).

It is preferred to use the sensitizing dyes according to the present invention in combination with the following methods which can be exemplified as preferred methods to realize silver halide grains having a spectral absorption maximum wavelength of less than 500 nm and light absorption strength of 60 or more, or a spectral absorption maximum wavelength of 500 nm or more and light absorption strength of 100 or more.

Such methods include, for instance, the methods of using a dye having an aromatic group or a cationic dye having an aromatic group in combination with an anionic dye as disclosed in JP-A-10-239789, JP-A-8-269009, JP-A-10-123650 and JP-A-8-328189, the method of using a dye having polyvalent charge as disclosed in JP-A-10-171058, the method of using a dye having a pyridinium group as disclosed in JP-A-10-104774, the method of using a dye having a hydrophobic group as disclosed in JP-A-10-186559, and the method of using a dye having a coordination bond group as disclosed in JP-A-10-197980.

The particularly preferred usages of the sensitizing dyes according to the present invention are the methods of using a dye having at least one aromatic group as disclosed in JP-A-10-239789, JP-A-8-269009, JP-A-10-123650 and JP-A-8-328189, and the dye compounds according to the present invention are used as the cationic dyes in these methods. Among these methods, there are a method of preferably using only a dye positively charged, and a method of using dyes positively charged and negatively charged in combination and either of the dye positively charged or the dye negatively charged has at least one aromatic group as a substituent. The dye compounds according to the present invention show the intended effect of the present invention when used as cationic dyes in each method. Further, the dyes of the present may be used as betaine dyes.

The layer number of adsorption of a dye chromophore onto silver halide grains is preferably 1.5 layers or more, more preferably 1.7 layers or more, and particularly preferably 2 layers or more, in total. The upper limit of the number of layers is not particularly limited but is preferably 10 layers or more, more preferably 5 layers or more.

In the present invention, when the saturated adsorption amount per a unit area attained by a dye having the smallest dye occupation area of the silver halide grain surface among the sensitizing dyes added to the emulsion is taken as one layer saturation covering amount, the state in which one or more layers of the chromophore is adsorbed onto the surface of a silver halide grain means the state in which the adsorption amount of the chromophore per a unit area is more than the one layer saturation covering amount. The layer number of adsorption means the adsorption amount with the one layer saturation covering amount as the standard. In the case of a dye comprising dye chromophores connected by covalent bonding, the dye occupation area of each dye in the state of not being connected can be made standard.

The dye occupation area can be obtained from the adsorption isothermal line showing the relationship between a free dye density and an adsorption dye amount and the surface area of a grain. The adsorption isothermal line can be found by referring to A. Herz et al., *Adsorption from Aqueous Solution* in Advances in Chemistry Series, No. 17, p 173 (1968), for instance.

The amount of a sensitizing dye adsorbed onto emulsion grains can be obtained from a method comprising centrifuging the emulsion onto which a dye is adsorbed, separating the emulsion into emulsion grains and a supernatant gelatin solution, obtaining the non-adsorbed dye-density by spectral absorption determination of the supernatant and subtracting the thus-obtained non-adsorbed dye density from the addition amount of the dye to thereby obtain the adsorbed amount of the dye, and from a method comprising drying the precipitated emulsion grains, dissolving a specific weight of the precipitate in a 1/1 mixed solution of an aqueous sodium thiosulfate solution and methanol, and obtaining the adsorbed amount of the dye by spectral absorption determination. When a plurality of sensitizing dyes are used, the adsorption amount of each dye can also be found, for example, by high speed liquid chromatography. A method of obtaining a dye adsorption amount by determining the dye amount in a supernatant is described, for example, in W. West et al., *Journal of Physical Chemistry*, Vol. 56, p. 1054 (1952). However, when large amounts of dyes are added, even non-adsorbed dyes sometimes precipitate, hence a correct adsorption amount cannot necessarily be obtained by the method of measuring the dye density in a supernatant. On the other hand, with the method of dissolving precipitated silver halide grains and determining the dye adsorption amount, as the precipitation speed of emulsion grains is overwhelmingly faster than that of a dye and the silver halide grains, the dye can be separated easily, and only the amount of the dye adsorbed onto the silver halide grains can be correctly determined, and this method is the most reliable method for obtaining the dye adsorption amount.

As one example of measuring methods of a silver halide grain surface area, a method of calculating a form and size of each grain from a transmission electromicrophotograph by a replica method is available. In this case, the thickness of a tabular grain is calculated from the length of the shadow of a replica. As for the photographing method of a transmission electromicrophotograph, *Denshi Kenbikyo Shiryo Gijutsu-Shu*, compiled by Nihon Denshi Kenbikyo Gakkai Kanto Branch, published by Seibundo Shinkosha Co., Ltd. (1970) and P. B. Hirsch et al., *Electron Microscopy of Thin Crystals*, Butterworths, London (1965) can be referred to.

As other methods, e.g., A. M. Kragin et al., *The Journal of Photographic Science*, Vol. 14, p. 185 (1966), J. F. Paddy, *Transactions of the Faraday Society*, Vol 60, p. 1325 (1964), S. Boyer et al., *Journal de Chimie Physique et de Physicochimie Biologique*, Vol. 63, p. 1123 (1963), W. West et al., *Journal of Physical Chemistry*, Vol. 56, p. 1054 (1952), compiled by H. Sauvenier, E. Klein et al., *International Coloquim*, Liege (1959), and *Scientific Photography* can be referred to.

The dye occupation area can be obtained by the above methods as to individual case experimentally, but as the molecule occupation area of generally used sensitizing dyes is about 80 Å$^2$, adsorption layer number can also be estimated roughly with taking the dye occupation area of all the dyes as 80 Å$^2$ for convenience' sake.

When dye chromophores are multilayer-adsorbed onto silver halide grains in the present invention, the reduction potentials and oxidation potentials of the chromophore of the so-called first layer and the chromophores of on and after the second layers are not particularly restricted, but it is preferred that the value of the reduction potential of the chromophore of the first layer is more positive than the value obtained by subtracting 0.2 v from the value of the reduction potential of the chromophore of on and after the second layers.

Reduction potential and oxidation potential can be measured by various methods but a measuring method by phase discriminating second harmonic AC polarography is preferred, by which a correct value can be obtained. The measuring method of potential according to phase discriminating second harmonic AC polarography is described in *Journal of Imaging Science*, Vol. 30, p. 27 (1986).

Further, dye chromophores of on and after the second layers are preferably luminescent dyes. As the kinds of luminescent dyes, those having a basic structure of dyes which are used for dye laser are preferred. Such luminescent dyes are described, for example, in Mitsuo; Maeda, *Laser Kenkyu*, Vol. 8, pp. 694, 803 and 958 (1980), and Vol. 9, p. 85 (1981), and F. Sehaefer, *Dye Lasers*, Springer (1973).

It is preferred that the absorption maximum wavelength of the chromophore of the first layer in a silver halide photographic material is longer than the absorption maximum wavelength of the chromophore of on and after the second layers. Further, it is preferred that the light emission of on and after the second layers overlap the absorption of the chromophore of the first layer It is preferred for the chromophore of the first layer to form a J-aggregate. Moreover, for silver halide grains to have absorption and spectral sensitivity in a desired wavelength region, it is also preferred for the chromophore of on and after the second layers to form a J-aggregate.

The meanings of the terminologies for use in the present invention are described below.

Dye occupation area: The occupation area per a molecule of a dye. The dye occupation area can be obtained experimentally from the adsorption isothermal line. In the case of a dye comprising dye chromophores connected by covalent bonding, the dye occupation area of each dye in the state of not being connected is made standard. It is regarded as 80 Å$^2$ for convenience' sake.

One layer saturation covering amount: The adsorption amount of a dye per a unit surface area of a silver halide grain at one layer saturation covering, which is a reciprocal of the occupation area attained by a dye having the smallest dye occupation area among the sensitizing dyes added to the emulsion.

Multilayer adsorption: The state in which the adsorption amount of a dye chromophore per a unit surface area of a grain is more than the one layer saturation covering amount.

Adsorption layer number: The adsorption layer number means the adsorption amount of a dye chromophore per a unit surface area of a grain when the one layer saturation covering amount is taken as the standard.

The distance between the shortest wavelength and the longest wavelength respectively showing 50% of the maximum value of spectral absorption factor Amax and the maximum value of spectral sensitivity Smax by a sensitizing dye of the emulsion containing silver halide photographic emulsion grain having light absorption strength of 100 or more is preferably 100 nm or less.

The distance between the shortest wavelength and the longest wavelength respectively showing 80% of Amax and Smax is 20 nm or more, and preferably 100 nm or less, more preferably 80 nm or less, and most preferably 50 nm or less.

The distance between the shortest wavelength and the longest wavelength respectively showing 20% of Amax and Smax is preferably 180 nm or less, more preferably 150 nm or less, particularly preferably 120 nm or less, and most preferably 100 nm or less.

Silver halide grains having light absorption strength of 60 or more at the spectral absorption maximum wavelength of less than 500 nm or light absorption strength of 100 or more at the spectral absorption maximum wavelength of 500 nm or more can be realized by the above preferred method, but as dyes of on and after the second layers are generally in the state of monomers, an absorption band and a spectral sensitivity band become broader than desired ranges in almost all the cases. Accordingly, to realize high sensitivity at a desired wavelength region, it is preferred for the dyes adsorbed onto on and after the second layers to form J-aggregates.

In the present invention, the dyes of on and after the second layers are dyes which are adsorbed onto silver halide grains but not directly adsorbed onto silver halide grains.

In the present invention, the J-aggregates of the dyes of on and after the second layers are defined such that the absorption band on the long wavelength side of the absorption shown by the dyes adsorbed onto on and after the second layers is two times or less of the absorption band on the long wavelength side of the absorption shown by a dye solution in a monomer state which is free from the interaction between dye chromophores. "The absorption band on the long wavelength side" herein means the energy breadth between the absorption maximum wavelength and the wavelength longer than the absorption maximum wavelength and shows the absorption of 1/2 of the absorption maximum. It is known that when a dye forms a J-aggregate, the absorption band on the long-wavelength side becomes small as compared with the time when the dye is in the state of a monomer. When a dye is adsorbed onto on and after the second layers in the state of a monomer, the absorption band of the dye becomes 2 times or more larger than that of the dye solution in a monomer state on the long wavelength side due to the position of adsorption and unevenness of conditions. Therefore, the J-aggregates of on and after the second layers can be defined by the above definitions.

The spectral absorption of the dyes adsorbed onto on and after the second layers can be obtained by subtracting the spectral absorption by the dye of the first layer from the spectral absorption of the emulsion at large.

The spectral absorption by the dye of the first layer can be obtained by measuring the absorption spectrum of the time when only the dye of the first layer is added Further, the spectral absorption spectrum by the dye of the first layer can also be measured by adding a dye desorbing agent to the emulsion onto which sensitizing dyes are multilayer-adsorbed to thereby desorb the dyes of on and after the second layers.

In the experiment of desorbing dyes from the surface of a grain with a dye desorbing agent, as the dye of the first layer is generally desorbed after the dyes of on and after the second layers have been desorbed, the spectral absorption by the dye of the first layer can be obtained if appropriate desorbing conditions are selected, hereby it becomes possible to obtain the spectral absorption of the dyes of on and after the second layers. The method of using a dye desorbing agent is described in Asanuma et al., *Journal of Physical Chemistry B*, Vol. 101, pp. 2149 to 2153 (1997).

The methine compound represented by formula (I) according to the present invention can be used in combination with other sensitizing dyes in a silver halide photographic material.

The time of the addition of the methine compounds according to the present invention the present invention to the silver halide emulsion may be at any stage of the preparation of the emulsion recognized as useful hitherto. For example, they may be added at any stage if it is before coating, i.e., before grain formation stage of silver halide grains and/or before desalting stage, during desalting stage and/or after desalting and before beginning of chemical sensitization, as disclosed in U.S. Pat. Nos. 2,735,766, 3,628,960, 4,183,756, 4,225,666, JP-A-58-184142 and JP-A-60-196749, or immediately before or during chemical ripening, after chemical ripening and before coating of the emulsion as disclosed in JP-A-58-113920. Further, as disclosed in U.S. Pat. No. 4,225,666and JP-A-58-7629, the sensitizing dyes can be used as a single compound alone or in combination with compounds having different structures, and they can be divided and added separately, for example, one part of them is added during grain formation stage and the remaining is added during chemical ripening stage or after completion of chemical ripening, alternatively one part is added prior to chemical ripening or during ripening stage and the remaining after completion of chemical sensitization. The kinds of compounds added separately and combinations of compounds may be varied.

Dyes other than the dye represented by formulae (III) (including formulae (VIII) and (IX) of subordinate concept hereinafter) may be used in the present invention, but the dye represented by formula (III) accounts for 50% or more, more preferably 70% or more, and most preferably 90% or more, of the total addition amount of-dyes.

The addition amount of the methine compound of the present invention varies according to the forms and sizes of silver halide grains to be used, but it can be used in an amount of from $1\times10^{-6}$ to $8\times10^{-2}$ mol per mol of the silver halide. For example, when the sizes of the silver halide grains are from 0.2 to 1.3 μm, the addition amount is preferably from $2\times10^{-6}$ to $3.5\times10^{-2}$ mol per mol of the silver halide, and more preferably from $7.5\times10^{-6}$ to $1.0\times10^{-2}$ mol per mol of the silver halide.

The compound represented by formula (I), (II) or (III) according to the present invention may be directly dispersed in an emulsion, or may be dissolved in a single or mixed solvent of methyl alcohol, ethyl alcohol, methyl cellosolve, aqueous acetone, pyridine, DMF, fluorine alcohol, etc., and the compound may be added to the emulsion in the form of the solution. Additives such as an acid, a base and a surfactant may coexist at that time. Further, ultrasonic waves can be used for dissolution. Moreover, various methods can be used for the addition of the compound represented by formula (I), (II) or (III) to an emulsion, e.g., a method in which the compound is dissolved in a volatile organic solvent, the solution is dispersed in hydrophilic colloid and this dispersion is added to an emulsion as disclosed in U.S. Pat. No. 3,469,987, a method comprising dispersing the compound in a water-soluble solvent and adding the dispersion to an emulsion as disclosed in JP-B-46-24185, a method comprising dissolving the compound in a surfactant and adding the solution to an emulsion as disclosed in U.S. Pat. No. 3,822,135, a method comprising dissolving the compound using a compound capable of red-shifting and adding the solution to-an emulsion as disclosed in JP-A-51-74624, or a method comprising dissolving the methine compound in an acid substantially not containing water and adding the solution to an emulsion as disclosed in JP-A-50-80826 can be used In addition, methods disclosed in U.S. Pat. Nos. 2,912,343, 3,342,605, 2,996,287, and 3,429,835 can be used for adding the compound to an emulsion.

The compound according to the present invention can contain various filter dyes, irradiation preventing dyes, and antihalation dyes for the purpose of improving sharpness and color separation ability.

These compounds can be contained in coating solutions for a silver halide photographic photosensitive layer, a filter layer, and/or an antihalation layer by ordinary methods. The use amount of the dyes should be sufficient to color photographic layers and those skilled in the art can easily select the amount according to use purposes. It is preferred in general to select the amount to give optical density of from 0.05 to 3.0.

The dyes may be added at any stage if it is before coating.

Further, polymers having the countercharges to dye ions may be contained in the same layer as a mordant to interact with dye molecules, thereby dyes can be localized in a specific layer.

Polymer mordants disclosed in U.S. Pat. Nos. 2,548,564, 4,124,386, 3,625,694, 3,958,995, 4,168,976 and 3,445,231 can be used in the present invention.

Supersensitizers preferably used in spectral sensitization in the present invention are, e.g., pyrimidylamino compounds, triazinylamino compounds, and azolium compounds disclosed in U.S. Pat. Nos. 3,511,664, 3,615,613, 3,615,632, 3,615,641, 4,596,767, 4,945,038 and 4,965,182, and using methods disclosed in these patents are also preferably used.

In the present invention, any of silver bromide, silver iodobromide, silver chlorobromide, silver iodide, silver iodochloride, silver iodobromochloride, and silver chloride may be used in a photographic emulsion constituting photosensitive mechanism. When the iodide content of the halogen composition of the outermost surface of an emulsion is preferably 0.1 mol % or more, more preferably 1 mol % or more, and particularly preferably 5 mol % or more, stronger multilayer adsorption structure can be constructed.

The grain size distribution may be either broad or narrow but narrow distribution is preferred.

Silver halide grains in a photographic emulsion may have a regular crystal form such as a cubic, octahedral, tetradecahedral, or rhombic dodecahedral form, an irregular crystal form such as a spherical or tabular form, a crystal form which has a {hkl} plane, or a form which is a mixture of these crystal forms, but tabular grain forms are preferably used. Tabular grains are described in detail below. Grains having a {hkl} plane are described in *Journal of Imaging Science*, Vol. 30, pp. 247 to 254 (1986).

The silver halide photographic emulsion for use in the present invention may contain the above silver halide grains alone or in combination of two or more. The interior and the surface layer of the silver halide grains may comprise different phases, may have a multi-phase structure having conjugation structure, may have a local phase on the surfaces of grains, or the entire grain may comprise a uniform phase. Silver halide grains may also comprise mixtures of these phases.

These emulsions may be a surface latent image type mainly having a latent image on the surface of a grain or an internal latent image type mainly having a latent image inside of a grain.

The silver halide emulsions for use in the present invention comprise preferably tabular silver halide grains onto which the sensitizing dyes according to the present invention are adsorbed and have higher surface area/volume ratio. The tabular silver halide grains have an aspect ratio of from 2 to 100, preferably from 5 to 80, and more preferably from 8 to 80, and a grain thickness of preferably less than 0.2 μm, more preferably less than 0.1 μm, and still more preferably less than 0.07 μm. For producing thin tabular grains having such a high aspect ratio, the following techniques are applied.

In the present invention, tabular silver halide grains having halogen compositions comprising silver chloride, silver bromide, silver chlorobromide, silver iodobromide, silver chloroiodobromide, and silver iodochloride are preferably used. The tabular grains having {100} or {111} main planes are preferably used. The tabular grains having {111} main planes (hereinafter referred to as "{111} tabular grains") generally have triangular or hexagonal planes. In general, the more uniform the grain size distribution, the higher is the ratio of tabular grains having hexagonal planes. Hexagonal monodispersed tabular grains are disclosed in JP-B-5-61205.

The tabular grains having {100} main planes (hereinafter referred to as "{100} tabular grains") have a rectangular form or a square form. In this emulsion, grains having an adjacent side ratio of less than 5/1, not acicular grains, are called tabular grains. In silver chloride or tabular grains having a high silver chloride content, {100} tabular grains are originally high in main plane stability as compared with {111} tabular grains. With {111} tabular grains, it is essential to stabilize {111} main planes, and JP-A-9-80660, JP-A-9-80656 and U.S. Pat. No. 5,298,388 can be referred to.

Silver chloride or {111} tabular grains having a high silver chloride content for use in the present invention are disclosed in U.S. Pat. Nos. 4,414,306, 4,400,463, 4,713,323, 4,783,398, 4,962,491, 4,983,508, 4,804,621, 5,389,509, 5,217,858, and 5,460,934.

High silver bromide content {111} tabular grains for use in the present invention are disclosed in U.S. Pat. Nos. 4,425,425, 4,425,426, 4,434,266, 4,439,520, 4,414,310, 4,433,048, 4,647,528, 4,665,012, 4,672,027, 4,678,745, 4,684,607, 4,593,964, 4,722,886, 4,755,617, 4,755,456, 4,806,461, 4,801,522, 4,835,322, 4,839,268, 4,914,014, 4,962,015, 4,977,074, 4,985,350, 5,061,609, 5,061,616, 5,068,173, 5,132,203, 5,272,048, 5,334,469, 5,334,495, 5,358,840 and 5,372,927.

{100}Tabular grains for use in the present invention are disclosed in U.S. Pat. Nos. 4,386,156, 5,275,930, 5,292,632, 5,314,798, 5,320,938, 5,319,635, 5,356,764, European Patents 569971, 737887, JP-A-6-308648 and JP-A-9-5911.

The silver halide emulsions for use in the present invention are generally chemically sensitized. In chemical sensitization according to the present invention, chalcogen sensitization (e.g., sulfur sensitization, selenium sensitization and tellurium sensitization), noble metal sensitization (e.g., gold sensitization), and reduction sensitization are used alone or in combination.

In the present invention, at least selenium-sensitized silver halide emulsions are preferably used. That is, selenium sensitization alone, combination of selenium sensitization and other chalcogen sensitization and/or noble metal sensitization (in particular, gold sensitization) are preferred, and combination of selenium sensitization and noble metal sensitization is particularly preferred.

Labile selenium compounds-are used in selenium sensitization as a sensitizer. Labile selenium compounds are disclosed in JP-B-43-13489, JP-B-44-15748, JP-A-4-25832, JP-A-4-109240, JP-A-4-271341, and JP-A-5-40324. Specific examples of selenium sensitizers include colloidal metal selenium, selenoureas (e.g., N,N-dimethylselenourea, trifluoromethylcarbonyltrimethylselenourea, acetyltrimethylselenourea), selenoamides (e.g., selenoacetamide, N,N-diethylphenylselenoamide), phosphineselenides (e.g. triphenylphosphineselenide, pentafluorophenyltriphenylphosphineselenide), selenophosphates (e.g., tri-p-tolyl-selenophosphate, tri-n-butylselenophosphate), seleno ketones (e.g., selenobenzophenone), isoselenocyanates, seleno-carboxylic acids, seleno esters, and diacylselenides. In addition, relatively stable selenium compounds, such as selenious acid, potassium selenocyanide, selenazoles and selenides (disclosed in JP-B-46-4553 and JP-B-52-34492) can also be used as a selenium sensitizer.

In sulfur sensitization, labile sulfur compounds are used as a sensitizer. Labile sulfur compounds are disclosed in P. Glafkides, *Chimie et Physique Photographigue,* 5th Ed., Paul Montel (1987) and *Research Disclosure,* Vol. 307, No. 307105. Specific examples of sulfur sensitizers include thiosulfates (e.g., hypo), thioureas (e.g., diphenylthiourea, triethylthiourea, N-ethyl-N'-(4-methyl-2-thiazolyl)thiourea, carboxymethyltrimethylthiourea), thioamides (e.g., thio-acetamide), rhodanines (e.g., diethyl rhodanine, 5-benzylidene-N-ethyl rhodanine), phosphine sulfides (e.g., trimethylphosphine sulfide), thiohydantoins, 4-oxo-oxazolidine-2-thiones, disulfides or polysulfides (e.g., dimorpholine disulfide, cystine, hexathiocane thione), mercapto compounds (e.g., cysteine), polythionate, and elemental sulfur. Active gelatins-can also be used as a sulfur sensitizer.

Labile tellurium compounds are used in tellurium sensitization as a sensitizer. Labile tellurium compounds are disclosed in Canadian Patent 800,958, British Patents 1,295, 462, 1,396,696, JP-A-4-204640, JP-A-4-271341, JP-A-4-333043 and JP-A-5-303157. Specific examples of tellurium sensitizers include telluroureas (e.g., tetramethyltellurourea, N,N'-dimethylethylenetellurourea, N,N'-diphenyl-ethylenetellurourea), phosphinetellurides (e.g., butyl-diisopropylphosphinetelluride, tributylphosphinetelluride, tributoxyphosphinetelluride, ethoxydiphenylphosphinetelluride), diacyl(di)tellurides (e.g., bis(diphenylcarbamoyl)ditelluride, bis(N-phenyl-N-methylcarbamoyl)-ditelluride, bis(N-phenyl-N-methylcarbamoyl)telluride, bis(ethoxycarbonyl)telluride), isotellurocyanates, telluro-amides, tellurohydrazides, telluro esters (e.g., butylhexyl-telluro ester), telluro ketones (e.g., telluroacetophenone), colloidal tellurium, (di)tellurides, and other tellurium compounds (e.g., potassium telluride, sodium telluropentathionate).

In noble metal sensitization, noble metal salts of gold, platinum, palladium, and iridium are used as sensitizers. Noble metal salts are disclosed in P. Glafkides, *Chimie et Physique Photographique,* 5th Ed., Paul Montel (1987) and *Research Disclosure,* Vol 307, No. 307105. Gold sensitization is particularly preferred. As described above, the effect of the present invention is particularly exhibited in the mode of conducting gold sensitization.

It is described in *Photographic Science and Engineering*, Vol. 19322 (1975) and *Journal of Imaging Science*, Vol. 3228 (1988) that gold can be removed from the sensitization speck of an emulsion grain using a solution containing potassium cyanide (KCN). According to these descriptions, a cyanogen ion makes a gold atom or a gold ion adsorbed onto a silver halide grain liberate as a cyanogen complex to thereby hinder gold sensitization. The action of gold sensitization can be sufficiently obtained by suppressing the occurrence of cyanogen according to the present invention.

Examples of gold sensitizers include chloroauric acid, potassium chloroaurate, potassium aurithiocyanate, gold sulfide, and gold selenide, as well as gold compounds disclosed in U.S. Pat. Nos. 2,642,361, 5,049,484 and 5,049,485.

Reducing compounds are used as a sensitizer in reduction sensitization. Reducing compounds are described in P. Glafkides, *Chimie et Physique Photographique,* 5th Ed., Paul Montel (1987), and *Research Disclosure*, Vol. 307, No. 307105. Examples of reducing sensitizers include aminoiminomethanesulfinic acid (thiourea dioxide), borane compounds (e.g., dimethylamineborane), hydrazine compounds (e.g., hydrazine, p-tolylhydrazine), polyamine compounds (e.g., diethylenetriamine, triethylenetetramine), stannous chloride, silane compounds, reductones (e.g., ascorbic acid), sulfite, aldehyde compounds, and hydrogen gas. Reduction sensitization can be performed in the atmosphere of high pH and excessive silver ion (so-called silver ripening). Reduction sensitization is preferably conducted during silver halide grain formation.

The use amount of a sensitizer is in general determined according to the kind of silver halide grains to be used and the conditions of chemical sensitization.

The use amount of a chalcogen sensitizer is generally from $10^{-8}$ to $10^{-2}$ mol, preferably from $10^{-7}$ to $5\times10^{-3}$ mol, per mol of the silver halide.

The use amount of a noble metal sensitizer is preferably from $10^{-7}$ to $10^{-2}$ mol per mol of the silver halide.

The conditions of chemical sensitization are not particularly limited. pAg is in general from 6 to 11, preferably from 7 to 10, pH is preferably from 4 to 10, and temperature is preferably from 40 to 95° C., and more preferably from 45 to 85° C.

The disclosure in JP-A-10-239789, from line 36, column 63 to line 2, column 65 can be applied to the producing method of the photographic emulsion for use in the present invention.

Also, with respect to additives such as color couplers, the addition of additives to photographic materials, the kinds of the photographic materials which are applicable to the present invention, and the processing of photographic materials, the disclosure in JP-A-10-239789, from line 3, column 65 to line 13, column 73 is applicable.

EXAMPLE

The present invention will be described in detail below with reference to specific examples, but it should not be construed as being limited thereto.

Example 1

Synthesis of Compound III-41

Compound III-41 was synthesized according to the following reaction scheme 1.

Reaction Scheme 1

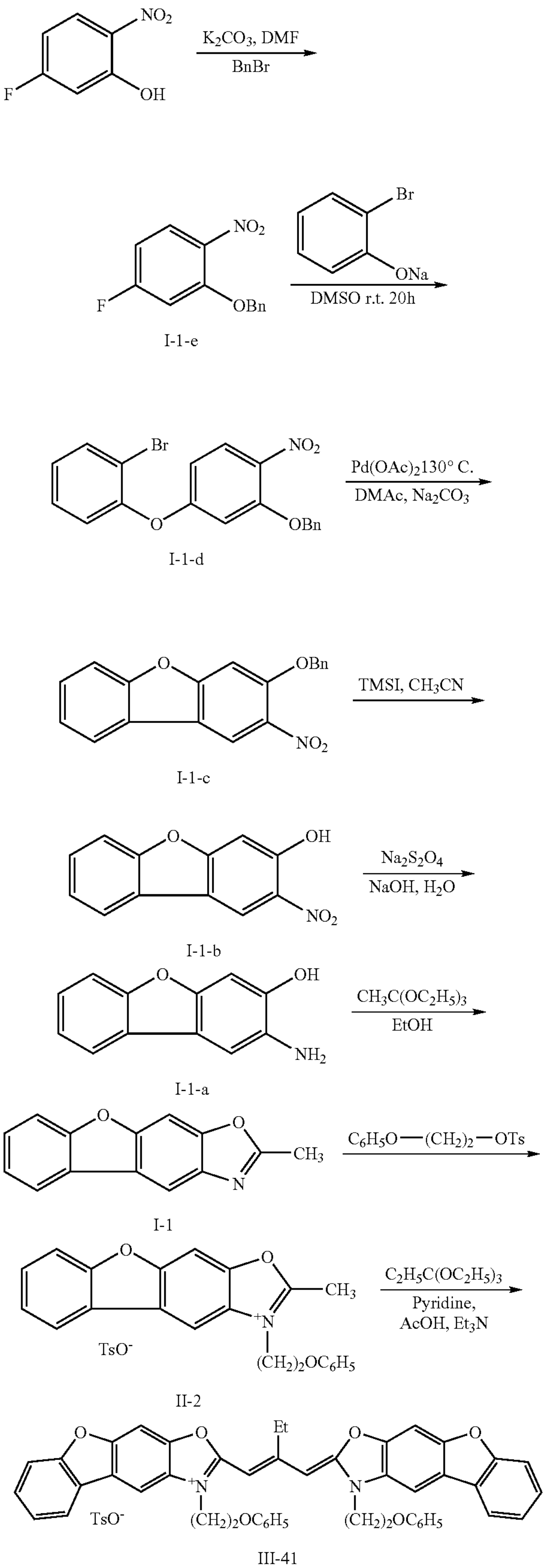

I-1-e, I-1-d, I-1-c, I-1-b, I-1-a, I-1, II-2, III-41

Synthesis-of Compound I-1-e

5-Fluoro-2-nitrophenol (10 g) was put into a three-neck flask having a capacity of 300 ml, and 70 ml of DMF was added thereto to dissolve the content. Subsequently, 10 g of potassium carbonate and 10.8 g of benzyl bromide were added to the reaction solution and the solution was stirred for 3 hours at room temperature. Thereto was added 500 ml of water and the reaction mixture was extracted with 500 ml of ethyl acetate. The organic phase was separated, washed with 200 ml of water two times, then with 100 ml of a saturated brine, dried over magnesium sulfate, filtered, and the solvent was distilled off under reduced pressure. Crude crystals of Compound I-1-e thus-obtained was recrystallized with methanol to obtain 7.0 g of Compound I-1-e (yield: 64%).

Synthesis of Compound I-1-d

Sodium hydride (6.4 g) was put into a three-neck flask having a capacity of 300 ml under nitrogen atmosphere, washed with 0.10 ml of toluene two times, 300 ml of DMSO and 23.1 g of o-bromophenol were successively added thereto, and the reaction mixture was stirred for 20 minutes at outer temperature of 80° C. After the reaction mixture was cooled to room temperature, 33.0 g of Compound I-1-e was added thereto, followed by stirring the reaction mixture at room temperature for 25 hours. To the reaction solution were added 100 ml of a saturated aqueous solution of ammonium chloride and 500 ml of distilled water, and the reaction solution was extracted with 600 ml of dichloromethane. The organic phase was washed successively with 500 ml of distilled water and 200 ml of a saturated brine After the organic phase was dried over magnesium sulfate, the solvent was distilled off under reduced pressure. The organic layer was washed with methanol and filtered after cooling, thereby 34.5 g of Compound I-1-d was obtained (yield: 65%, melting point: 72° C.)

Synthesis of Compound I-1-c

Under nitrogen atmosphere, 10.0 g of Compound I-1-d was put into an egg plant-shaped flask having a capacity of 300 ml equipped with a magnetic stirrer, and 150 ml of dimethylacetamide and 50 ml of acetonitrile were added thereto. After stirring the content, 5.0 g of sodium carbonate, 2.5 g of palladium acetate and 11.6 g of triphenylphosphine were successively added to the reaction solution, and the reaction solution was heated at outer temperature of 170° C., followed by stirring the mixture for 4 hours at the same temperature. Subsequently, 500 ml of distilled water was added thereto and the reaction solution was extracted with 500 ml-of ethyl acetate. The extract was successively washed with 300 ml of distilled water and 100 ml of a saturated brine, dried over magnesium sulfate, and the solvent was distilled off under reduced pressure The dried product was dissolved in acetonitrile, dusts were filtered, and 30 ml of a 1N aqueous sodium hydroxide solution was added thereto, thereby crystals were precipitated. The crystals precipitated were collected by filtration. The procedure from the dissolution in acetonitrile was repeated one more time. The crystals obtained were dried under reduced pressure, thereby 19 g of Compound I-1-c was obtained (yield: 24%).

Synthesis of Compound I-1-b

Under nitrogen atmosphere, 19 g of Compound I-1-c was put into an egg plant-shaped flask having a capacity of 300 ml equipped with a magnetic stirrer, and 150 ml of acetonitrile was added thereto. After stirring the content, 2.5 ml of trimethylsilyl iodide was added to the reaction solution, heated at outer temperature of 50° C. for 1 hour, and then 2.0 ml of trimethylsilyl iodide was added, followed by stirring the reaction solution for 2 hours at the same temperature. After cooling, the reaction mixture was rendered acidic with the addition of sulfuric acid, and then extracted with dichloromethane. The extract was washed with a saturated brine, dried over magnesium sulfate, and the solvent was distilled off under reduced pressure. The residue was purified by silica gel column chromatography ($SiO_2$: 100 g, solvent: hexane/ethyl acetate, 100 to 20), thereby 0.95 g of Compound I-1-b was obtained (yield: 70%, melting point 159° C.)

Synthesis of Compound I-1

Compound I-1-b (0.9 g) was put into an egg plant-shaped flask having a capacity of 200 ml equipped with a magnetic stirrer, 1.5 g of sodium dithionite, 10 ml of water, 6 ml of ethanol, and 12 ml of a 1N aqueous sodium hydroxide solution were successively added thereto. The reaction mixture was heated at outer temperature of 80° C. for 30 minutes, then cooled, dusts were filtered, and pH was adjusted to about 6 with the addition of sulfuric acid The crystals precipitated were collected by filtration and dried under reduced pressure to thereby obtain Compound I-1-a. The thus-obtained Compound I-1-a was put into an egg plant-shape flask having a capacity of 200 ml equipped with a magnetic stirrer, 5 ml of triethyl orthoacetate and 40 ml of ethanol were added thereto, and the reaction mixture was heated at outer temperature of 110° C. for 25 hours, and then the solvent was distilled off under reduced pressure. The residue was purified by silica gel column chromatography ($SiO_2$: 100 g, solvent: hexane/ethyl acetate, 7), thereby 400 mg of compound I-1 was obtained (yield from Compound I-1-b: 46%, melting point 124° C.)

$^1$H-NMR δ (DMSO-$d_6$, 300 MHz): 2.69 (3H, s, Me), 7.43 (1H, t, J 8.2 Hz), 7.53 (1H, dt, J 14 Hz, 8.2 Hz), 7.71 (1H, d, J 8.2 Hz), 8.05 (1H, s), 8.22 (1H, d, J 8.2 Hz), 8.41 (1H, s).

Synthesis of Compound II-2

Compound I-1 (0.2 g) and 0.5 g of phenoxyethyl tosylate were mixed and stirred at 150° C. for 3 hours. After cooling the reaction mixture, 100 ml of ethyl acetate was added thereto and then the reaction mixture was stirred at room temperature for 2 hours. The crystals were collected by filtration and dried to thereby obtain 0.39 g of Compound II-2 (yield: 84%, melting point: 272° C.).

Synthesis of Compound III-41

Compound II-2 (0.39 g), 1.5 ml of triethyl orthopropionate, 1.5 ml of pyridine, 0.5 ml of acetic acid, and 0.5 ml of triethylamine were mixed and stirred at 1.50° C. for 20 minutes. After the reaction mixture was cooled, 50 ml of ethyl acetate was added thereto, followed by stirring the mixture at room temperature for 30 minutes. The crystals were collected by filtration. Acetone was added to the crystals obtained and the crystals were boiled for 30 minutes, cooled, filtered, and dried under reduced pressure to thereby obtain 0.10 g of Compound III-41 (yield: 29%).

($\lambda_{max}$: 5218 nm, $\epsilon$: $1.71\times10^5$, melting point: 255° C.)

Example 2

Synthesis of Compound III-40

Compound III-40 was synthesized according to the following reaction scheme.

Reaction Scheme

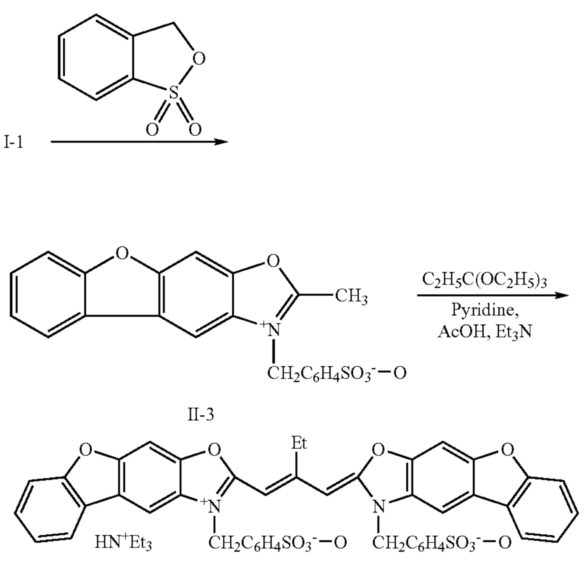

I-1

II-3

III-40

Synthesis of Compound II-3

Compound I-1 (0.2 g) and 0.5 g of tolylsultone were mixed and stirred at 150° C. for 3 hours. After the reaction mixture was cooled, 100 ml of ethyl acetate was added thereto, followed by stirring the mixture at room temperature for 2 hours. The crystals were collected by filtration and dried, thereby 0.48 g of Compound II-3 was obtained (yield: 100%, melting point: 279° C.)

Synthesis of Compound III-40

Compound III-40 (0.48 g), 1.5 ml of triethyl orthopropionate, 1.5 ml of pyridine, 0.6 ml of acetic acid, and 0.5 ml of triethylamine were mixed and stirred at 150° C. for 20 minutes. After the reaction mixture was cooled, 50 ml of ethyl acetate was added thereto, followed by stirring the mixture at room temperature for 30 minutes. The crystals were collected by filtration. The crystals obtained were dissolved in a 1/1 mixed solution of methanol/chloroform with heating. After dusts were filtered, the solution was boiled for 30 minutes, and when concentrated to 1/2 of the initial amount, cooled and allowed to stand. The crystals precipitated were filtered and dried under reduced pressure to thereby obtain 0.20 g of Compound III-40 (yield: 48%). ($\lambda_{max}$: =522.0 nm, $\epsilon$: $1.71\times10^5$, melting point: 248° C.)

Example 3

Synthesis of Compound II-1

Compound II-1 was synthesized according to the following reaction scheme.

Reaction Scheme

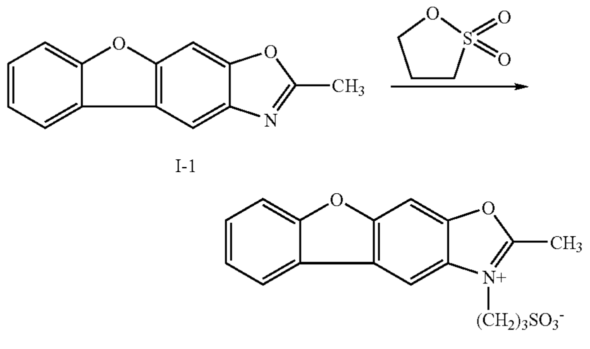

I-1

II-1

Synthesis of Compound II-1

Compound I-1 (0.3 g) and 0.5 g of propanesultone were mixed and stirred at 150° C. for 3 hours. After the reaction mixture was cooled, 100 ml of ethyl acetate was added thereto, followed by stirring the mixture at room temperature for 2 hours. The crystals were collected by filtration and dried, thereby 0.44 g of Compound II-1 was obtained (yield: 95%, melting point: 283° C.)

Example 4

Synthesis of Compound III-51

Compound III-51 was synthesized according to the following reaction scheme.

Reaction Scheme

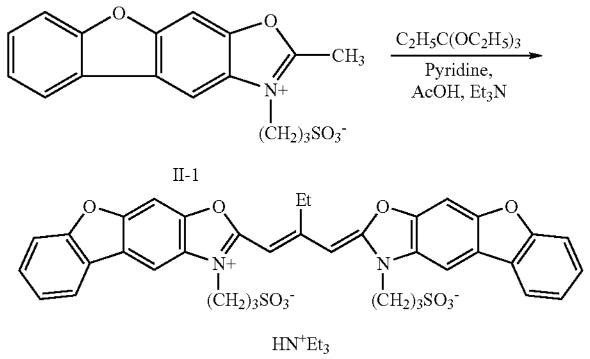

II-1

III-51

Synthesis of Compound III-51

Compound II-1 (0.44 g), 1.5 ml of triethyl orthopropionate, 15 ml of pyridine, 0.6 ml of acetic acid, and 0.7 ml of triethylamine were mixed and stirred at 150° C. for 20 minutes. After the reaction mixture was cooled, 50 ml of ethyl acetate was added thereto, followed by stirring the mixture at room temperature for 30 minutes. The crystals were collected by filtration. Acetone was added to the crystals obtained and the crystals were boiled for 30 min utes, cooled, filtered, and dried under reduced pressure to thereby obtain 0.33 g of Compound III-51 (yield: 63%).

($\lambda_{max}$: 520 nm, $\epsilon$: $1.34\times10^5$, melting point: 269° C.)

Example 5

Synthesis of Compound III-71

Compound III-71 was synthesized according to the following reaction scheme.

H-NMR (DMSO-$d_6$) δ: 7.97–7.93 (m, 2H), 7.78 (s, 1H), 7.56 (d, 1H), 7.47 (t, 1H), 7.34 (t, 1H), 2.70 (s, 3H)

Mass (posi): 224 $(M+H)^+$

Synthesis of Compound II-13

To 0.96 g (4.3 mmol) of Compound I-37 were added 1.2 g (6.4 mmol) of methyl p-toluenesulfonate and 2 ml of anisole, and the reaction solution was stirred with heating at 140° C. for one hour. The temperature of the reaction solution was then lowered to room temperature, and ethyl Reaction Scheme

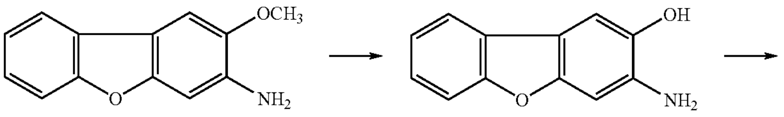

I-37-a

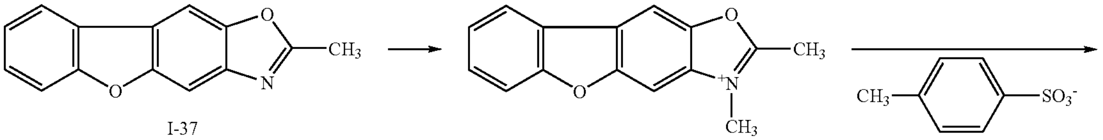

I-37

II-13

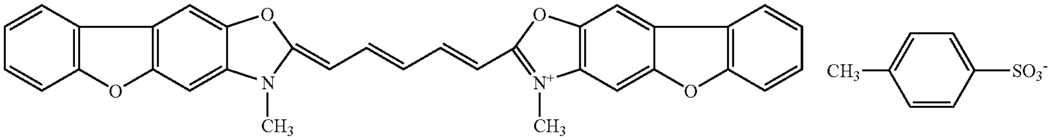

III-71

Synthesis of Compound I-37-a

3-Amino-2-methoxybenzofuran (42.6 g) (0.2 mol) was dissolved in 400 ml of acetic acid, 340 ml of a 47% aqueous hydrogen bromide solution was added thereto, and the reaction solution was refluxed with heating for 12 hours. The reaction solution was neutralized with an aqueous solution of sodium hydroxide and extracted with ethyl acetate. The ethyl acetate phase was concentrated under reduced pressure, and the residue obtained was recrystallized with ethanol to obtain Compound I-37-a. Yielded amount: 38 g, Yield: 95.4%.

H-NMR (DMSO-$d_6$) δ: 7.80–7.74 (m, 1H), 7.50–7.43 (m, 1H), 7.30–7.19 (m, 3H), 6.83 (d, 1H)

Mass (posi): 200 $(M+H)^+$

Synthesis of Compound I-37

To 19.9 g (0.1 mol) of Compound I-37-a were added 55 ml (0.3 mol) of ethyl orthoacetate and 50 ml of ethanol, and the reaction solution was heated at outer temperature of 115° C. for, 30 minutes. Crystals were obtained by cooling the reaction solution, and the crystals were filtered to thereby obtain Compound I-37. Yielded amount: 21 g, Yield: 94%.

acetate was added thereto, thereby crystals were precipitated. The crystals precipitated were filtered, thus Compound II-13 was obtained. Yielded amount: 1.7 g, Yield: 95%.

Mass (posi): 238 $(M)^+$

Synthesis of Compound III-71

Compound II-13 (1.0 g) (2.4 mmol) and 0.26 g (1.2 mmol) of malondialdehydodianil were dissolved in 15 ml of dimethylformamide, and 0.35 ml (2.5 mmol) of triethylamine and 0.24 ml (25 mmol) of acetic anhydride were added thereto. The reaction solution was allowed to react at 60° C. for one hour. The reaction solution was cooled with water, thereby crystals were precipitated. The crude crystals collected by filtration were recrystallized with a mixed solvent of chloroform and methanol. Thus, Compound III-71 was obtained. Yielded amount: 0.28 g, Yield: 34%.

Mass (posi): 511 $(M+H)^+$

Absorption maximum wavelength (methanol): 618 nm

Molecular extinction coefficient. (methanol): 220,000

Excitation maximum wavelength (methanol): 622 nm (concentration: $1.0\times10^{-6}$ M)

Fluorescence maximum wavelength (methanol): 641 nm (concentration: $1.0\times10^{-6}$ M)

Example 6

Synthesis of Compound III-72

Compound III-72 was synthesized according to the following reaction scheme.

the reaction solution to precipitate crystals, and the, crystals precipitated were filtrated to thereby obtain Compound II-21. Yielded amount: 0.94 g, Yield: 45%.

Mass (nega): 416 (M−H)

Synthesis of Compound III-72-a

Compound II-21 (0.42 g) (1 mmol) and 0.11 g (0.5 mmol) of malondialdehydodianil were dissolved in 5 ml of dim- Reaction Scheme

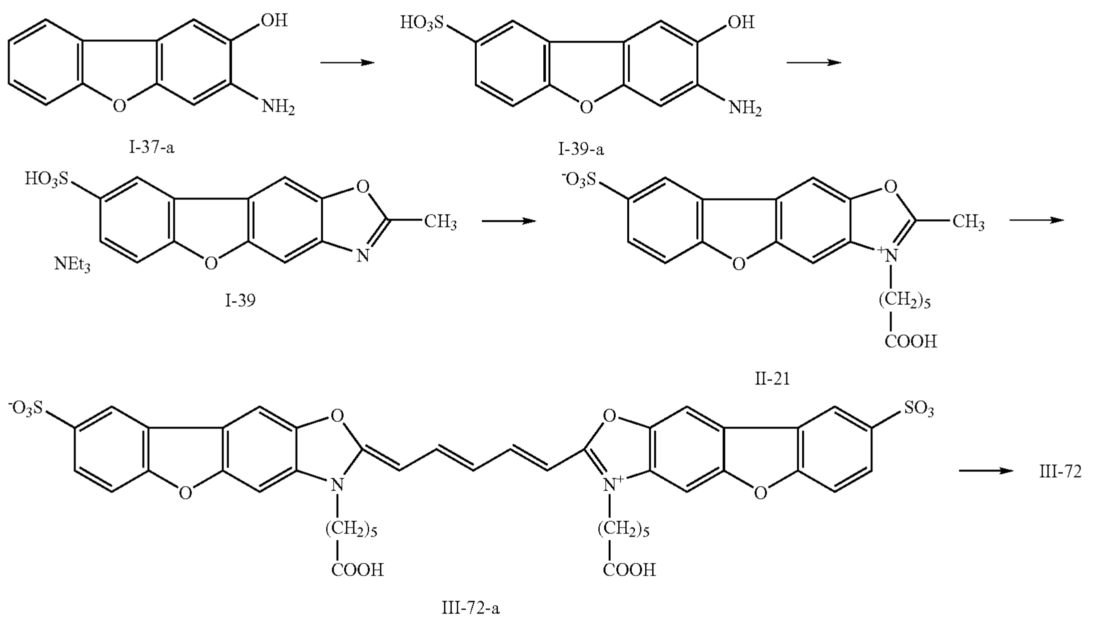

I-37-a I-39-a I-39 II-21 III-72-a III-72

Synthesis of Compound I-39-a

Compound I-37-a (4.0 g) (20 mmol) and 57 ml of concentrated sulfuric acid were mixed while cooling with water, and the mixture was allowed to react while cooling with water for 5 minutes and at room temperature for further 5 minutes. The reaction solution was added to 300 ml of ethyl acetate to precipitate crystals. The crystals were collected by filtration, thereby Compound I-39-a was obtained. Yielded amount: 4.9 g, Yield: 88%.

$^1$H-NMR (DMSO-$d_6$) δ: 10.8 (bs, 1H), 8.25 (s, 1H), 7.80 (d, 1H), 7.65 (s, 1H), 7.61 (d, 1H), 7.53 (s, 1H)

Synthesis of Compound I-39

To 4.0 g (14.3 mmol) of Compound I-39-a were added 16 ml of ethanol, 2.0 ml of triethylamine, and 8 ml of ethyl orthoacetate, and the reaction solution was heated at outer temperature of 115° C. for 30 minutes. The reaction solution was concentrated under reduced pressure, isopropyl alcohol was added to the residue to precipitate crystals, and the crystals precipitated were filtrated to thereby obtain Compound I-39. Yielded amount: 4.7 g, Yield: 81%.

H-NMR (DMSO-$d_6$) δ: 8.56 (s, 1H), 8.48 (d, 1H), 7.95 (s, 1H), 7.79 (dd, 1H), 7.63 (d, 1H), 3.10 (dd, 6H), 2.68 (s, 3H), 1.18 (t, 9H)

Synthesis of Compound II-21

Compound I-39 (2.0 g) (5 mmol) and 1.1 g (5.5 mmol) of 6-bromohexanic acid were dissolved in 2 ml of dimethylacetamide, and the reaction solution was heated at 145° C. for 1 hour and 155° C. for 3 hours. Ethyl acetate was added to ethylformamide, and 0.14 ml (1 mmol) of triethylamine and 0.1 ml (1 mmol) of acetic anhydride were added thereto. The reaction solution was allowed to react at 60° C. for one hour. The reaction solution was cooled with water, and crystals precipitated were filtered. The crude crystals obtained were purified by column packed with Sephadex LH-20 (manufactured by Pharmacia Biotech Co.), thereby triethylamine salt of Compound III-72-a was obtained. The thus-obtained triethylamine salt was dissolved in methanol, and potassium acetate was added thereto to precipitate III-72-a (potassium salt). The crystals were filtered, and recrystallized with methanol to thereby obtain Compound III-72-a. Yielded amount: 91 mg, Yield: 20%.

Mass (nega): 870 (M−K)

Absorption maximum wavelength (methanol): 622 nm

Molecular extinction coefficient (methanol): 220,000

Excitation maximum wavelength (methanol): 626 nm (concentration: $1.0\times10^{-6}$ M)

Fluorescence maximum wavelength (methanol): 645 nm (concentration: $1.0\times10^{-6}$ M)

Synthesis of Compound III-72

Compound III-72-a (91 mg) (0.1 mmol) was dissolved in 1.5 ml of dimethylformamide and 0.1 ml of pyridine, and 77 mg (03 mmol) of N,N'-disuccinimidylcarbonate was added thereto, and the reaction mixture was allowed to react at 45°

C. for 3 hours. Acetone was added to the reaction solution to precipitate crystals, and the crystals were filtered, thereby Compound III-72 was obtained. Yielded amount: 105 mg, Yield: 95%.

Mass (nega): 1064 (M−K).

Absorption maximum wavelength (methanol): 622 nm

Molecular extinction coefficient (methanol): 220,000

Excitation maximum wavelength (methanol): 626 nm (concentration: $1.0\times10^{-6}$ M)

Fluorescence maximum wavelength (methanol): 645 nm (concentration: $1.0\times10^{-6}$ M)

Example 7

Synthesis of Compound III-73

Compound III-73 was synthesized according to the following reaction scheme.

Absorption maximum wavelength (methanol): 625 nm

Molecular extinction coefficient (methanol): 215,000

Excitation maximum wavelength (methanol): 628 nm (concentration: $1.0\times10^{-6}$ M)

Fluorescence maximum wavelength (methanol): 648 nm (concentration: $1.0\times10^{-6}$ M)

Example 8

Synthesis of Oxazolocarbazole Derivatives

Oxazolocarbazole derivatives I-4, I-3, I-7, I-9, I-12 and I-10 shown below were synthesized according to the synthesis method described in *Journal of Organic Chemistry*, Vol. 41, p. 1118 (1976). As the substitution introduction methods of oxazolocarbazole skeletons to benzene rings, (1) general nitration to unsubstituted oxazolocarbazole, introduction of an amino group by reduction and alkylation or Reaction Scheme

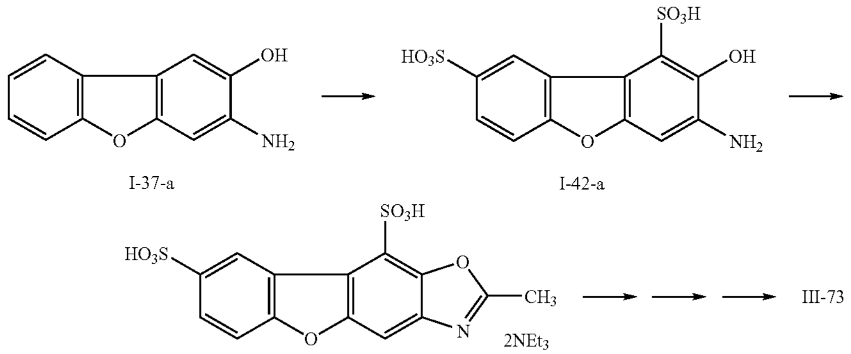

I-37-a

I-42-a

I-42

III-73

Synthesis of Compound I-42-a

Concentrated sulfuric acid (10 ml) and 10 ml of 60% fuming sulfuric acid were mixed under cooling with water, 2.0 g (10 mmol) of Compound I-37-a was added thereto and the reaction solution was-stirred at room temperature for 10 hours. The reaction solution was added to 200 ml of ethyl acetate to precipitate crystals, and the crystals precipitated were filtrated to thereby obtain Compound I-42-a. Yielded amount: 2.5 g, Yield: 69%.

H-NMR ($D_2O$) δ: 9.05 (d, 1H), 7.81 (dd, 1H), 7.68 (s, 1H), 7.57 (d, 1H)

Mass (nega): 358 (M−H)

Synthesis of Compound I-42

To 2.0 g (5.6 mmol) of Compound I-42-a were added 6 ml of ethanol, 1.8 ml of triethylamine, and 6 ml of ethyl orthoacetate, and the reaction solution was heated at outer temperature of 115° C. for 1 hour. The reaction solution was concentrated under reduced pressure, isopropyl alcohol was added to the residue to precipitate crystals, and the crystals precipitated were filtrated to thereby obtain Compound I-42. Yielded amount: 2.8 g, Yield: 86%.

H-NMR (DMSO-$d_6$) δ: 9.28 (d, 1H), 7.92 (s, 1H), 7.78 (dd, 1H), 7.55 (d, 1H), 3.12 (dd, 12H), 2.65 (s, 3H), 1.18 (t, 18H)

Synthesis of Compound III-730

Compounds I-42 to Compound III-73 were obtained in the same manner as in the synthesis of Compound III-72.

acylation of the amino group, (2) sulfation by concentrated sulfuric acid, and (3) acylation by Friedel-Crafts reaction were used.

I-4

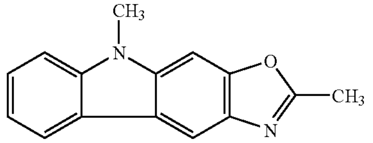

I-3

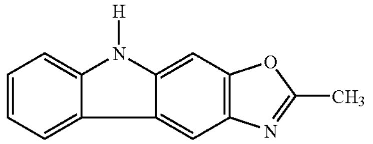

I-7

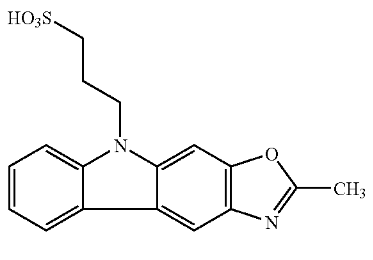

-continued

I-9

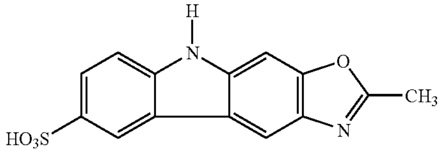

I-12

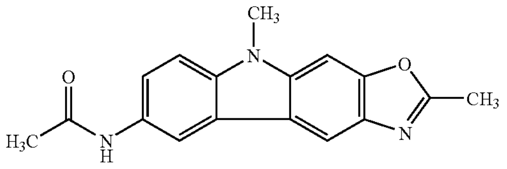

I-10

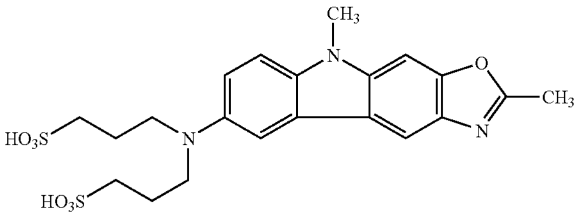

Example 9

Conversion of Oxazolocarbazole Derivative to Quaternary Salt

Oxazolocarbazole derivatives synthesized in Example 8 were converted to quaternary salt compounds II-20, II-19, II-25, II-27, II-28, II-29, II-15 and II-31 shown below.

II-20

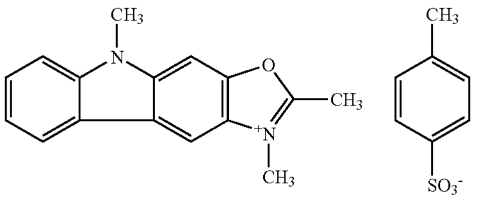

II-19

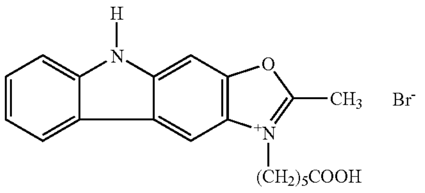

II-25

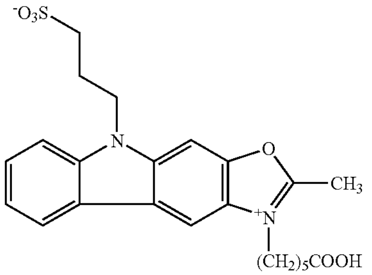

-continued

II-27

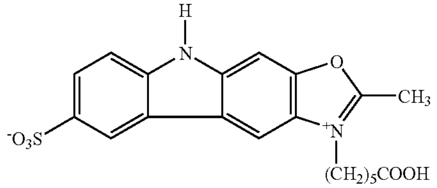

II-29

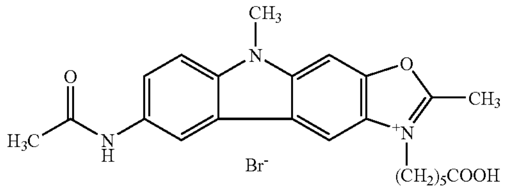

II-28

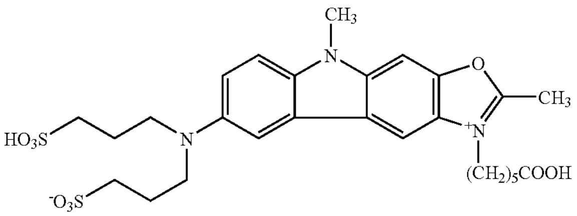

II-15

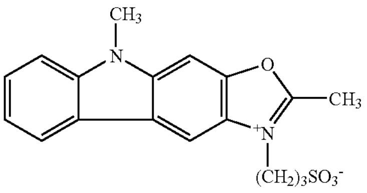

II-31

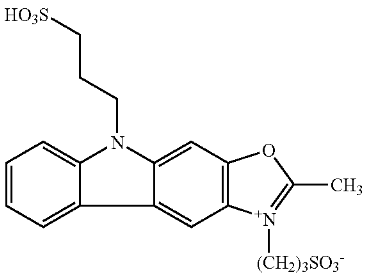

Synthesis of Compound II-20

To 2.4 g (10 mmol) of Compound I-37-a were added 2.8 g (15 mmol) of methyl p-toluenesulfonate and 5 ml of anisole, and the reaction solution was stirred with heating at 140° C. for one hour. The temperature of the reaction solution was then lowered to room temperature, and ethyl acetate was added thereto, thereby crystals were precipitated. The crystals precipitated were filtered, thus Compound II-20 was obtained. Yielded amount: 4.2 g, Yield: quantitative.

Mass (posi): 251

Synthesis of Compound II-19

Compound I-37 (2.2 g) (10 mmol) and 2.2 g (11 mmol) of 6-bromohexanoic acid were dissolved in 2 ml of dimethylacetamide, and the reaction solution was heated at 145° C. for 1 hour and 155° C. for 3 hours Ethyl acetate was added to the reaction solution to precipitate crystals, and the crystals precipitated were filtrated to thereby obtain Compound II-19. Yielded amount: 2.3 g, Yield: 55%.

Mass (nega): 337

Synthesis of Compound II-25

Compound II-13 (3.4 g) (10 mmol) and 2.2 g (11 mmol) of 6-bromohexanoic acid were dissolved in 10 ml of dimethylacetamide, and the reaction solution was heated at 155° C. for 6 hours. Acetone was added to the reaction solution to precipitate crystals, and the crystals precipitated were filtrated to thereby obtain Compound II-25. Yielded amount: 2.7 g, Yield: 60%.

Mass (nega): 458

Syntheses of Compounds II-27, II-29, II-28

Syntheses were performed in the same manner as the synthesis of Compound II-25.

Example 10

Compounds III-76 to III-80 were synthesized by making the quaternary salts of oxazolocarbazole derivatives shown in Example 9 couple with the following compounds. Commercially available product was used as Compound IV-1.

IV-1

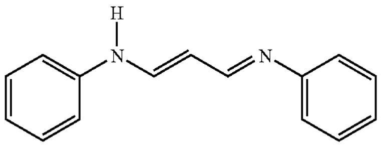

IV-2

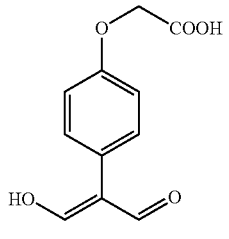

IV-3

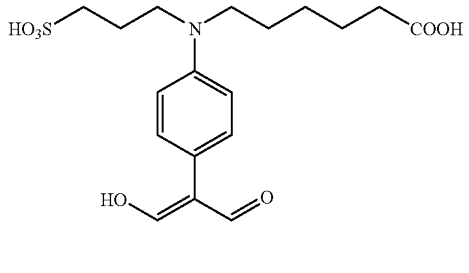

Compound IV-2 was synthesized according to the reaction scheme shown below.

Reaction Scheme

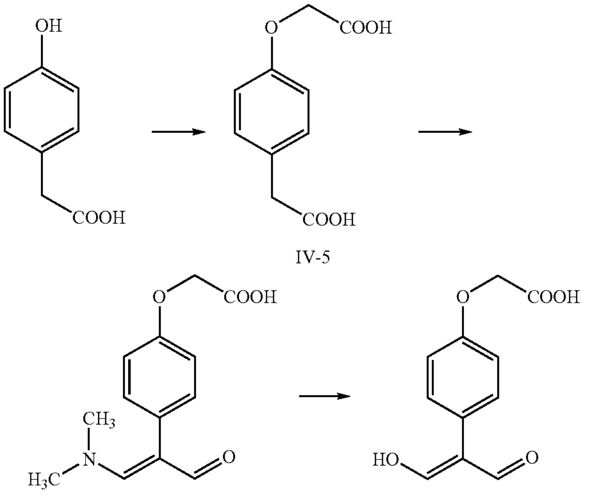

IV-5

IV-6

IV-2

Synthesis of Compound IV-5

4-Hydroxyhenylacetic acid (10.0 g) (66 mmol) was dissolved in 80 ml of a 10% aqueous sodium hydroxide solution, 6.4 g (66 mmol) of chloroacetic acid was added thereto, and the reaction solution was refluxed with heating for 3 hours. The reaction solution was cooled with ice, and rendered acidic with the addition of concentrated hydrochloric acid, thereby crystals of Compound IV-5 were precipitated. The crystals were collected by filtration. Yielded amount: 12.4 g, Yield: 90%.

H-NMR (DMSO-$d_6$) δ: 7.17 (d, 2H), 6.82 (d, 2H), 4.63 (s, 2H9, 3.52 (s, 2H)

Mass (posi): 211 (M+H)

Synthesis of Compound IV-6

To 20 ml of dimethylformamide was added 5.6 ml (60 mmol) of phosphorus oxychloride with ice-cooling such that the inner temperature did not exceed 10° C., then the temperature was risen to room temperature and the reaction solution was stirred for 20 minutes. To the reaction solution was added 4.2 g (20 mmol) of Compound IV-5, and the reaction solution was allowed to react at room temperature for 30 minutes, at 70° C. for 2 hours, and at 85° C. for 2 hours. The reaction solution was poured into 60 g of ice, 7.2 g of sodium hydroxide was added thereto, and stirred until the solution became homogeneous. Further, 40 ml of a 10 M aqueous sodium hydroxide solution was added thereto such that the inner temperature did not exceed 30° C., followed by stirring at room temperature for 2 hours. Subsequently, concentrated hydrochloric acid was added to the reaction solution with ice-cooling until the pH became 2, thereby the crystals of Compound IV-6 were precipitated. Yielded amount: 4.9 g, Yield: quantitative.

H-NMR (DMSO-$d_6$) δ: 8.90 (s, 1H), 7.15 (s, 1H), 6.95 (d, 2H), 6.82 (d, 2H), 4.62 (s, 2H), 3.50–2.50 (m, 6H)

Mass (posi): 250 (M+H)

Synthesis of Compound IV-2

To 2.5 g (10 mmol) of Compound IV-6 were added 15 ml of ethanol and 20 ml of a 25% aqueous sodium hydroxide solution, and the reaction solution was refluxed with heating for 3 hours. The reaction solution was concentrated under reduced pressure to distill off ethanol, and then neutralized with concentrated hydrochloric acid, thereby the crystals of Compound IV-2 were precipitated. Yielded amount: 1.6 g, Yield: 73%.

H-NMR (DMSO-$d_6$) δ: 12.5 (bs, 1H), 8.40 (bs, 2H), 7.40 (d, 2H), 6.86 (d, 2H), 4.65 (s, 2H)

Mass (posi): 223 (M+H)

Compound IV-3 was synthesized according to the reaction scheme shown below.

Reaction Scheme

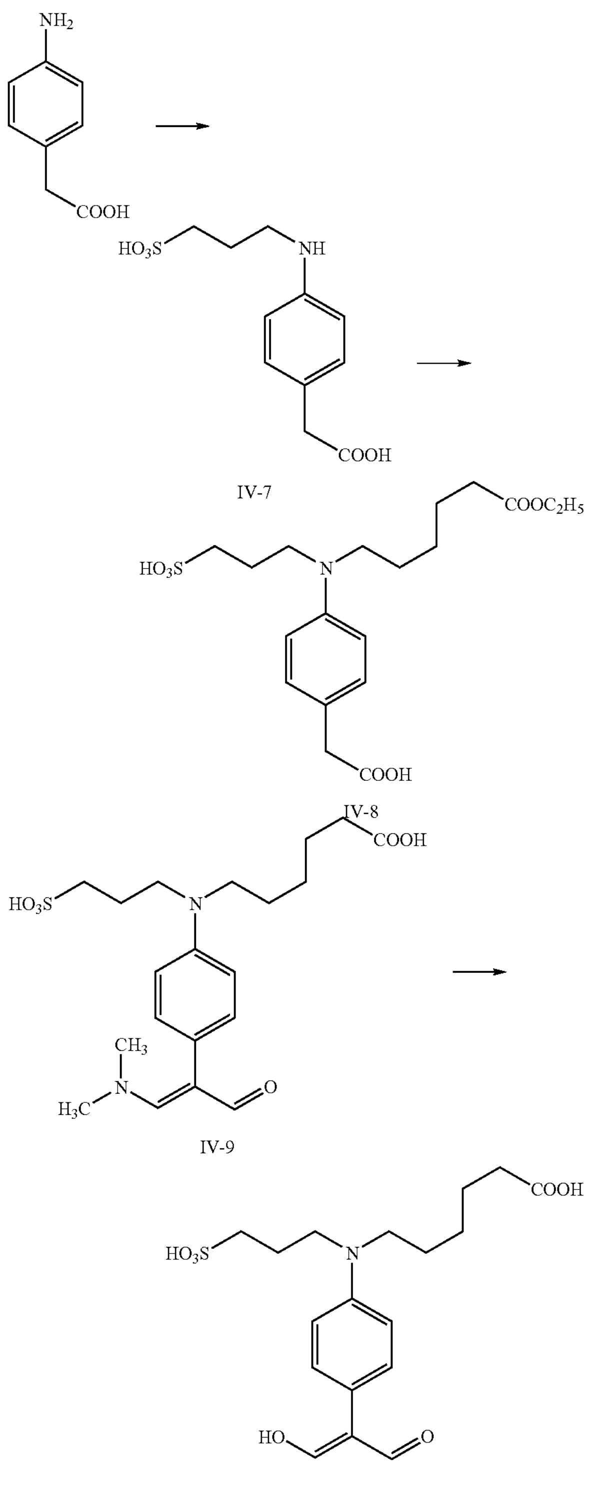

IV-7

IV-8

IV-9

IV-3

Synthesis of Compound IV-7

4-Aminophenylacetic acid (15.1 g) (0.1 mol) was dissolved in a mixed solvent of 120 ml of toluene and 100 ml of dimethylformamide, 9 ml of propanesultone was added thereto, and the reaction solution was allowed to react at 80° C. for 3 hours. The crystals precipitated in the reaction system were filtered and Compound IV-7 was obtained. Yielded amount: 19 g, Yield: 70%.

Mass (nega): 272 (M−H)

Synthesis of Compound IV-8

Compound IV-7 (27 g) (0.1 mol) was dissolved in 100 ml of dimethylacetamide, 40 g of potassium carbonate and 21 ml (0.12 mol) of 6-bromohexanoic acid ethyl ester were added thereto, and the reaction solution was allowed to react at 120° C. for 4 hours. The reaction solution was poured into ice water, neutralized with concentrated hydrochloric acid, and extracted with chloroform. The chloroform phase was concentrated under reduced pressure, thereby Compound IV-8 was obtained. Yielded amount: 29 g, Yield: 70%.

Mass (nega): 414 (M−H)

Synthesis of Compound IV-3

Compound IV-3 was synthesized in the same manner as the preparation of Compound IV-6 and Compound IV-2.

Mass (nega): 398 (M−H)

Example 11

Synthesis of Methine Compound

Synthesis of Compound III-76

Compound II-20 (4.2 g) (10 mmol) and 1.1 g (5 mmol) of Compound IV-1 were dissolved in 180 ml of dimethylformamide, and 1.4 ml (10 mmol) of triethylamine and 0.95 ml (10 mmol) of acetic anhydride were added thereto, and the reaction solution was allowed to react at 60° C. for 1 hour. The reaction solution was cooled with water, and crystals precipitated were filtered. The crude crystals obtained were recrystallized from a mixed solvent of chloroform and methanol, thereby Compound III-76 was obtained. Yielded amount: 1.2 g, Yield. 34%.

Mass (posi): 538

Synthesis of Compound III-77

Compound II-25 (0.46 g) (1 mmol) and 0.11 g (0.5 mmol) of Compound IV-1 were dissolved in 5 ml of dimethylformamide, and 0.14 ml (1 mmol) of triethylamine and 0.1 ml (1 mmol) of acetic anhydride were added thereto, and the reaction solution was allowed to react at 60° C. for 1 hour.The reaction solution was cooled with water, and crystals precipitated were filtered. The crude crystals obtained were purified by column packed with Sephadex LH-20 (manufactured by Pharmacia Biotech Co.), thereby triethylamine salt of carboxyl body of Compound III-77 was obtained. Thethus-obtained triethylamine salt was dissolved in methanol, and potassium acetate was added thereto to precipitate potassium salt of carboxyl body. The potassium salt of carboxyl body was dissolved in 1.5 ml of dimethylformamide and 0.1 ml of pyridine, and 0.4 g (1.5 mmol) of N,N'-disuccinimidylcarbonate was added thereto, and the reaction mixture was allowed to react at 45° C. for 3 hours. Acetone was added to the reaction solution to precipitate crystals, and the crystals were filtered, thereby Compound III-77 was obtained. Yielded amount: 0.19 g, Yield: 32%.

Mass (nega): 1146 (M−K)

Synthesis of Compound III-78

Compound III-78 was synthesized in the same manner as the preparation of Compound III-77 by using Compound II-27 and Compound IV-1. Yielded amount: 0.11 g, Yield: 20%.

Mass (nega): 1061 (M−K)

Synthesis of Compound III-79

Compound II-29 (4.8 g) (10 mmol) and 1.1 g (5 mmol) of Compound IV-1 were dissolved in 180 ml of dimethylformamide, and 1.4 ml (10 mmol) of triethylamine and 0.95 ml (10 mmol) of acetic anhydride were added thereto, and the reaction solution was allowed to react at 60° C. for 1 hour. The reaction solution was cooled with water, and crystals precipitated were filtered. The crude crystals obtained were recrystallized from a mixed solvent of chloroform and methanol, thereby carboxyl body of Compound III-79 was obtained The carboxyl body was dissolved in 15 ml of dimethylformamide and 3 ml of pyridine, and 4.0 g (1.5 mmol) of N,N'-disuccinimidylcarbonate was added thereto, and the reaction mixture was allowed to react at 45° C. for 3 hours. Acetone was added to the reaction solution to precipitate crystals, and the crystals were filtered, thereby Compound III-79 was obtained. Yielded amount: 2.3 g, Yield: 42%.

Mass (posi): 1045 (M−Br)

Synthesis of Compound III-80

Compound III-80 was synthesized in the same manner as the preparation of Compound III-77 by using Compound II-28 and Compound IV-1. Yielded amount: 0.25 g, Yield: 33%.

Mass (nega): 1499 (M−K)

Example 12

(1) Preparation of Emulsion

An aqueous solution of 1.9 M $AgNO_3$ and an aqueous solution of 19 M KBr were added by a double jet method to an aqueous solution containing gelatin having an average molecular weight of 15,000 (containing 1,200 ml of water, 7.0 g of gelatin, and 4.5 g of KBr) at a temperature maintained at 30° C. while stirring at a rate of 25 ml/min over 70 seconds to form tabular nuclei. Of the emulsion, 400 ml portion was seed crystals, to which were added 650 ml of an aqueous inert gelatin solution (containing 20 g of gelatin and 1.2 g of KBr), the temperature was risen to 75° C. and the mixture was subjected to ripening for 40 minutes. Subsequently, an aqueous $AgNO_3$ solution (containing 1.7 g of $AgNO_3$) was added to the above emulsion over 1 minute and 30 seconds, then 7.0 ml of an aqueous $NH_4NO_3$ solution (50 wt %) and 7.0 ml of an aqueous $NH_3$ solution (25 wt %) were added thereto, followed by ripening for further 40 minutes.

The pH of the emulsion was then adjusted to with $HNO_3$ (3N) and 1.0 g of KBr was added thereto, then 366.5 ml of an aqueous solution of 1.9 M $AgNO_3$ and an aqueous KBr solution, then 53.6 ml of an aqueous solution of 1.9 M $AgNO_3$ and an aqueous KBr solution (containing 33.3 mol % of KI), and then 160.5 ml of an aqueous solution of 1.9 M $AgNO_3$ and an aqueous KBr solution were added to the emulsion with maintaining pAg at 7.9, thus Emulsion 1 was obtained.

Emulsion 1 thus obtained was triple structural grain emulsion having the highest silver iodide content part at the intermediate shell, and the average aspect ratio of Emulsion 1 was 2.8. Tabular grains having an aspect ratio of 3 or more accounted for 26% of the entire projected area of the tabular grains. The variation coefficient of grain size was 7%, and the average grain size was 0.98 μm as an equivalent-sphere diameter.

Emulsion 1 was desalted according to an ordinary flocculation method, and a sensitizing dye was added per mol of the silver, and subjected to gold, sulfur and selenium sensitization optimally in the presence of the sensitizing dye.

Preparation of Coated Sample

On a triacetyl cellulose film support having an undercoat layer, the emulsion layer and the protective layer as shown in Table 1 were coated to prepare Sample Nos. 201 to 212.

TABLE 1

Emulsion Coating Conditions

| | | |
|---|---|---|
| (1) | Emulsion Layer | |
| | Emulsion: Emulsion 1 (used dye is shown in Table 2) | (silver, $2.1 \times 10^{-2}$ mol/m$^2$) |
| | Coupler | ($1.5 \times 10^{-3}$ mol/m$^2$) |
| | 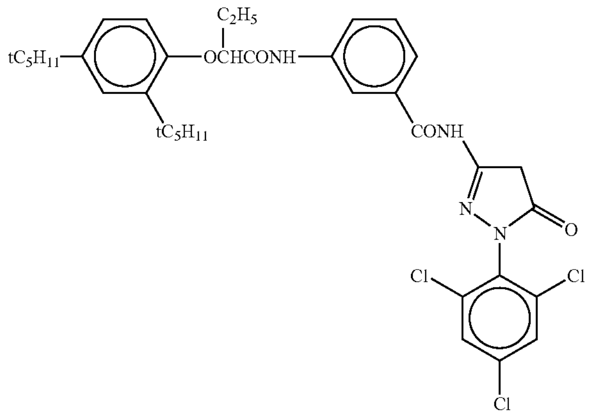 | |
| | Tricresyl phosphate | 1.10 g/m$^2$ |
| | Gelatin | 2.30 g/m$^2$ |
| (2) | Protective Layer | |
| | Sodium 2,4-dichloro-6-hydroxy-s-triazine | 0.08 g/m$^2$ |
| | Gelatin | 1.80 g/m$^2$ |

The absorption spectrum of each coated sample was measured with a spectrophotometer equipped with an integrating sphere, U-3410 (manufactured by Hitachi, Ltd.). Sensitivity is a value obtained by integrating the absorption strength on the longer wavelength side than 350 nm to axis of abscissa (eV) The results obtained are shown in Table 2.

Each sample was subjected to sensitometric exposure for 1/100 sec. and to the following development process.

| Processing Step | | | | |
|---|---|---|---|---|
| Step | Processing Time | Processing Temperature (° C.) | Replenishment Rate* (ml) | Tank Capacity (liter) |
| Color Development | 2 min 45 sec | 38 | 33 | 20 |
| Bleaching | 6 min 30 sec | 38 | 25 | 40 |
| Washing | 2 min 10 sec | 24 | 1,200 | 20 |
| Fixing | 4 min 20 sec | 38 | 25 | 30 |
| Washing (1) | 1 min 05 sec | 24 | counter-current system from (2) to (1) | 10 |
| Washing (2) | 1 min 00 sec | 24 | 1,200 | 10 |
| Stabilization | 1 min 05 sec | 38 | 25 | 10 |
| Drying | 4 min 20 sec | 55 | | |

Replenishment rate: per 1 meter of 35 mm wide

The composition of each processing solution is described below.

| | Mother Solution (g) | Replenisher (g) |
|---|---|---|
| Color Developing Solution | | |
| Diethylenetriaminepentaacetic Acid | 1.0 | 1.1 |
| 1-Hydroxyethylidene-1,1-diphosphonic Acid | 3.0 | 3.2 |
| Sodium Sulfite | 4.0 | 4.4 |
| Potassium Carbonate | 30.0 | 37.0 |
| Potassium Bromide | 1.4 | 0.7 |
| Potassium Iodide | 1.5 mg | — |
| Hydroxylamine Sulfate | 2.4 | 2.8 |
| 4-(N-Ethyl-N-β-hydroxyethylamino)-2-methylaniline Sulfate | 4.5 | 5.5 |
| Water to make | 1.0 l | 1.0 l |
| pH | 10.05 | 10.05 |
| Bleaching Solution | | |
| Sodium Ethylenediaminetetraacetato Ferrate Trihydrite | 100.0 | 120.0 |
| Disodium Ethylenediaminetetraacetate | 10.0 | 11.0 |
| Ammonium Bromide | 140.0 | 160.0 |
| Ammonium Nitrate | 30.0 | 35.0 |
| Aqueous Ammonia (27%) | 6.5 ml | 4.0 ml |
| Water to make | 1.0 l | 1.0 l |
| pH | 6.0 | 5.7 |
| Fixing Solution | | |
| Sodium Ethylenediaminetetraacetate | 0.5 | 0.7 |
| Sodium Sulfite | 7.0 | 8.8 |
| Sodium Bisulfite | 5.0 | 5.5 |
| Aqueous Solution of Ammonium Thiosulfate (70%) | 170.0 ml | 200.0 ml |
| Water to make | 1.0 l | 1.0 l |
| pH | 6.7 | 6.6 |
| Stabilizing Solution | | |
| Formalin (37%) | 2.0 ml | 3.0 ml |
| Polyoxyethylene-p-monononylphenyl Ether (polymerization degree: 10) | 0.3 | 0.45 |
| Disodium Ethylenediaminetetraacetate | 0.05 | 0.08 |

-continued

| | Mother Solution (g) | Replenisher (g) |
|---|---|---|
| Water to make | 1.0 l | 1.0 l |
| pH | 5.8–8.0 | 5.8–8.0 |

The density of processed sample was measured through a green filter.

The reciprocal of the exposure amount giving a density of fog (density)+0.2 is taken as sensitivity, and sensitivity is shown as a relative value taking the value of Sample No. 201 as 100. The emulsion and methine compound used in each sample and the sensitivity of each sample are shown in Table 2 below.

Comparative Dye

TABLE 2

| | Sensitizing Dye | | |
|---|---|---|---|
| Sample No. | Kind | Addition Amount | Sensitivity |
| 201 (Comparison) | S-1 | $4 \times 10^{-4}$ | 100 (control) |
| 202 (Invention) | III-51 | $4 \times 10^{-4}$ | 113 |
| 203 (Invention) | III-43 | $4 \times 10^{-4}$ | 120 |
| 204 (Invention) | III-44 | $4 \times 10^{-4}$ | 115 |
| 205 (Comparison) | S-2 | $4 \times 10^{-4}$ | 101 |
| 206 (Invention) | III-3 | $4 \times 10^{-4}$ | 115 |

S-1

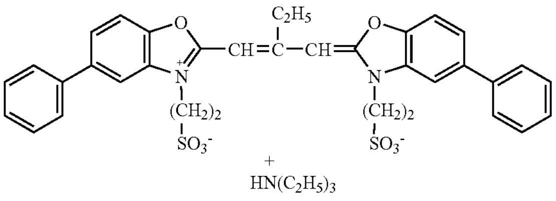

S-2

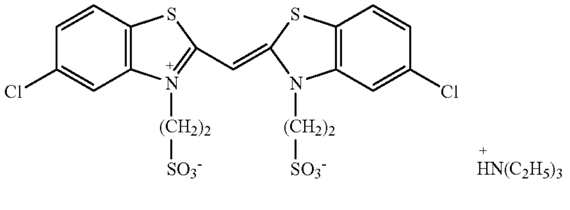

From the results in Table 2, it is apparent that samples according to the present invention show high sensitivity as compared with comparative samples.

Example 13

Preparations of Pure Silver Bromide Tabular Grain Emulsion and Silver Iodobromide Tabular Grain Emulsion In 1.2 liters of water were dissolved 6.4 g of potassium bromide and 6.2 g of low molecular weight gelatin having an average molecular weight of 15,000 or less, and 8.1 ml of a 16.4% aqueous silver nitrate solution and 7.2 ml of a 23.5% aqueous potassium bromide solution were added thereto by a double jet method over 10 seconds while maintaining the temperature at 30° C. Then, a 11.7% aqueous gelatin solution was further added to the reaction solution and ripening was performed for 40 minutes by increasing the temperature to 75° C., followed by the addition of 370 ml of a 32.2% aqueous silver nitrate solution and a 20% aqueous potassium bromide solution over 10 minutes with maintaining the silver potential at −20 mV. Ripening was performed for 1 minute and then the temperature was lowered to 35° C. Thus, a monodispersed pure silver bromide tabular grain emulsion (specific gravity: 1.15) having an average projected area diameter of 2.32 μm, a thickness of 0.09 μm and a variation coefficient of diameter of 15.1% was obtained.

Soluble salts were removed from the emulsion by a coagulation precipitation method. The temperature of the emulsion was maintained at 40° C., and 45.6 g of gelatin, 10 ml of an aqueous sodium hydroxide solution having concentration of 1 mol/liter, 167 ml of water, and 10 ml of a 5% phenol were added to the emulsion, pAg and pH were adjusted to 6.88 and 6.16, respectively, thereby Emulsion A was obtained.

Emulsion B was prepared in the same manner as the preparation of Emulsion A except that the 20% aqueous potassium bromide solution used in tabular grain growth was replaced with a mixed aqueous solution of 17% potassium bromide and 3% potassium iodide.

Subsequently, potassium thiocyanate, chloroauric acid and sodium thiosulfate were added to Emulsions A and B, and ripening was performed at 55° C. for 50 minutes so as to be optimally sensitized.

With maintaining each of the thus-obtained emulsion at 50° C., the first dye shown in Table 3 was added to each emulsion and the emulsion was stirred at 50° C. for 30 minutes, further the second dye was added and stirred at 50° C. for 30 minutes.

TABLE 3

| | | First Dye | | Second Dye | |
|---|---|---|---|---|---|
| | Emulsion | Kind | Amount ($10^{-3}$ mol/Ag mol) | Kind | Amount ($10^{-3}$ mol/Ag mol) |
| Comparison 1 | A | H-1 | 6.60 | None | — |
| Comparison 2 | A | H-1 | 3.60 | H-2 | 3.00 |
| Comparison 3 | A | None | — | H-2 | 6.60 |
| Invention 1 | A | H-1 | 3.60 | III-40 | 3.00 |
| Invention 2 | A | III-41 | 3.60 | III-40 | 3.00 |
| Invention 3 | A | III-41 | 3.60 | H-2 | 3.00 |
| Invention 4 | A | III-42 | 3.60 | III-40 | 3.00 |
| Invention 5 | B | III-41 | 6.60 | None | — |

H-1

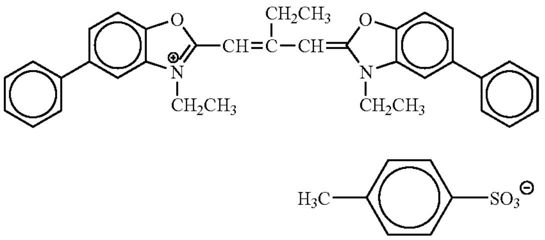

H-2 (=S-2)

TABLE 3-continued

| | | First Dye | | Second Dye | |
|---|---|---|---|---|---|
| | Emulsion | Kind | Amount ($10^{-3}$ mol/Ag mol) | Kind | Amount ($10^{-3}$ mol/Ag mol) |

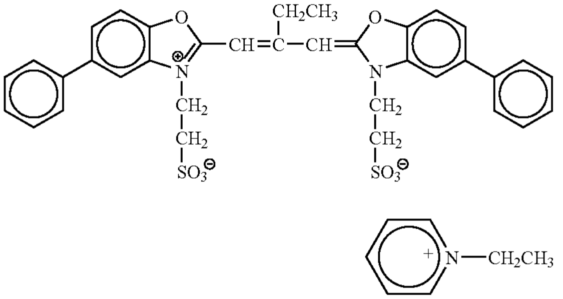

The dye adsorption amount was obtained as follows: The emulsion obtained was centrifuged at 10,000 rpm for 10 minutes to be precipitated, and the precipitate was freeze-dried, 25 ml of a 25% aqueous sodium thiosulfate solution and methanol was added to 0.05 g of the precipitate to make the volume 50 ml. This solution was analyzed by a high speed liquid chromatography and dye concentration was determined.

The measurement of the light absorption strength per unit area was conducted as follows: that is, the obtained emulsion was coated thinly on a slide glass and transmission spectrum and reflection spectrum of each grain were measured using a microspectrophotometer MSP 65 produced by Carl Zeiss Corp. according to the following method, from which absorption spectrum was searched for A portion where grains were not present was taken as a reference of transmission spectrum and silicon carbide the reflectance of which was known was measured and the obtained value was made a reference of reflection spectrum. The measuring part was a circular aperture of a diameter of 1 μm, and transmission spectrum and reflection spectrum were measured in the wave number region of from 14,000 $cm^{-1}$ (714 nm) to 28,000 $cm^{-1}$ (357 nm) by adjusting the position so that the aperture part was not overlapped with the contour of the grain. Absorption spectrum was found taking 1−T (transmittance)−R (reflectance) as absorption factor A, one from which the absorption by silver halide was deducted was taken as absorption A'. The value obtained by integrating −Log (1−A') to wave number ($cm^1$) was divided by 2 and this value was made the light absorption strength per unit surface area. The integrated region was from 14,000 $cm^{-1}$ to 28,000 $cm^{-1}$. A tungsten lamp was used as a light source and the light source voltage was 8 V. For minimizing the injury of a dye by irradiation of light, a primary monochromator was used, the distance of wavelength was 2 nm, and a slit width was 2.5 nm.

A gelatin hardening agent and a coating aid were added to the emulsion obtained, which was coated in a coating silver amount of 3.0 g-Ag/$m^2$ on a cellulose triacetate film support with a gelatin protective layer by a simultaneous coating method. The film obtained was exposed with a tungsten lamp (color temperature: 285° K) for 1 second through a continuous wedge color filter. As a color filter, UVD33S filter was combined with V40 filter (a product of Toshiba Glass Co., Ltd.) for blue exposure for exciting silver halide and the-sample was irradiated with light of wavelength range of 330 nm to 400 nm. Fuji gelatin filter SC-52 (a product of Fuji Photo Film Co., Ltd.) was used for minus blue exposure for exciting the dye side and the sample was irradiated with the light of 520 nm or less being cut off. The exposed sample was development processed at. 20° C. for 10 minutes with the following surface developing solution MAA-1.

| Surface Developing Solution MAA-1 | |
|---|---|
| Metol | 2.5 g |
| L-Ascorbic Acid | 10 g |
| Nabox (a product of Fuji Photo Film Co., Ltd.) | 35 g |
| Potassium Bromide | 1 g |
| Water to make | 1 liter |
| pH | 9.8 |

Optical density of the development processed film was measured using a Fuji automatic densitometer. Sensitivity was the reciprocal of the exposure amount required to give an optical density of fog +0.2 and expressed as a relative value taking Comparison 1 as a control, with fog being the density at the unexposed part.

The results obtained are shown in Tables 4 and 5 below As is shown in Table 4, using the two kinds of dyes according to the present invention, multilayer adsorption, onto the grain surface became feasible and the light absorption strength per unit area of a grain surface (1/2 of the light absorption strength of one grain) was conspicuously increased. Further, as a result, as shown in Table 5, color sensitization sensitivity was remarkably increased.

TABLE 4

| | Light Absorption | First Dye | | | Second Dye | | |
|---|---|---|---|---|---|---|---|
| | Strength per Unit Surface Area | Kind | Adsorption Amount ($10^{-3}$ mol/mol-Ag) | Covering Rate (%) | Kind | Adsorption Amount ($10^{-3}$ mol/mol-Ag) | Covering Rate (%) |
| Comparison 1 | 83 | H-1 | 1.47 | 98 | None | — | — |
| Comparison 2 | 82 | H-1 | 1.28 | 85 | H-2 | 0.17 | 11 |
| Comparison 3 | 76 | None | — | — | H-2 | 1.41 | 94 |
| Invention 1 | 132 | H-1 | 1.31 | 92 | III-40 | 1.07 | 79 |
| Invention 2 | 182 | III-41 | 2.15 | 142 | III-40 | 1.55 | 110 |
| Invention 3 | 215 | III-41 | 3.33 | 229 | H-2 | 2.15 | 145 |
| Invention 4 | 309 | III-42 | 3.08 | 204 | III-40 | 2.32 | 153 |
| Invention 5 | 210 | III-41 | 5.41 | 340 | None | — | — |

TABLE 5

| | Blue Sensitivity | Minus Blue Sensitivity | Color Sensitization Sensitivity (minus blue sensitivity/ blue sensitivity) |
|---|---|---|---|
| Comparison 1 | 100 | 100 | 100 |
| Comparison 2 | 97 | 99 | 102 |
| Comparison 3 | 95 | 96 | 101 |
| Invention 1 | 92 | 135 | 135 |
| Invention 2 | 99 | 170 | 175 |
| Invention 3 | 93 | 142 | 149 |

TABLE 5-continued

| | Blue Sensitivity | Minus Blue Sensitivity | Color Sensitization Sensitivity (minus blue sensitivity/ blue sensitivity) |
|---|---|---|---|
| Invention 4 | 94 | 207 | 214 |
| Invention 5 | 99 | 179 | 179 |

Example 14

Preparation of Silver Iodobromide Cubic Emulsion

One thousand (1,000) ml of water, 25 g of deionized ossein gelatin, 15 ml of a 50% aqueous solution of $NH_4NO_3$, and 7.5 ml of a 25% aqueous solution of $NH_3$ were put in a reaction vessel and stirred thoroughly, while maintaining the temperature at 50° C., then 750 ml of a 1N silver nitrate aqueous solution and an aqueous solution containing 1 mol/liter of potassium bromide and 0.05 mol/liter of potassium iodide were added over 50 minutes with maintaining the silver potential during reaction at +50 mV to a saturated calomel electrode.

The thus-obtained silver iodobromide grains were cubic having a side length of 0.78±0.06 nm. The temperature of the above emulsion was lowered, a copolymer of isobutene and monosodium maleate was added thereto as a coagulant, and the precipitate was washed with water and desalted. In the next place, 95 g of deionized ossein gelatin and 430 ml of water were added and pH and pAg were adjusted to 6.5 and 8.3, respectively, at 50° C. Subsequently, sodium thiosulfate was added and ripening was carried out over 50 minutes at 55° C. to obtain optimal sensitivity. One (1) kg of this emulsion contained 0.74 mol of silver bromide. This emulsion was designated Emulsion C.

Emulsion C was weighed each in 50 g portion and, with maintaining the temperature at 60° C., the mixture of the first dyes shown in Table 6 below was added to each emulsion and stirred at 60° C. for 10 minutes, then, the mixture of the second dyes was added and stirred for further 30 minutes at 60° C., thereafter each emulsion was coated as described below.

The coating amount of silver was 2.5 g/$m^2$ and the coating amount of gelatin was 3.8 g/$m^2$. An aqueous solution comprising as main components 0.22 g/liter of sodium dodecyl-benzenesulfonate, 0.50 g/liter of sodium p-sulfostyrene homopolymer, 3.1 g/liter of sodium 2,4-chloro-6-hydroxy-1,3,5-triazine, and 50 g/liter of gelatin was coated as an upper layer by a simultaneous coating method such that the coating amount of gelatin became 1.0 g/$m^2$.

Measurement of the dye adsorption amount, exposure and development were conducted in the same manner as in Example 12. Optical density of the development processed film was measured using a Fuji automatic derisitometer. Sensitivity was the reciprocal of the exposure amount required to give an optical density of fog +0.2 and expressed as a relative value taking Comparison 1 as a control, with fog being the density at the unexposed part.

TABLE 6

| | First Dye | | Second Dye | |
|---|---|---|---|---|
| | Kind of Dye and Addition Amount ($10^{-3}$ mol/mol-Ag) | Kind of Dye and Addition Amount ($10^{-3}$ mol/mol-Aq) | Kind of Dye and Addition Amount ($10^{-3}$ mol/mol-Ag) | Kind of Dye and Addition Amount ($10^{-3}$ mol/mol-Ag) |
| Comparison 1 | H-3 (1.60) | — | — | — |
| Comparison 2 | H-4 (1.60) | — | — | — |
| Invention 1 | H-4 (0.35) | III-29 (0.60) | H-5 (0.15) | III-28 (0.50) |
| Invention 2 | — | III-29 (0.95) | H-5 (0.15) | III-28 (0.50) |
| Invention 3 | H-4 (0.35) | III-29 (0.60) | — | III-28 (0.65) |

H-3

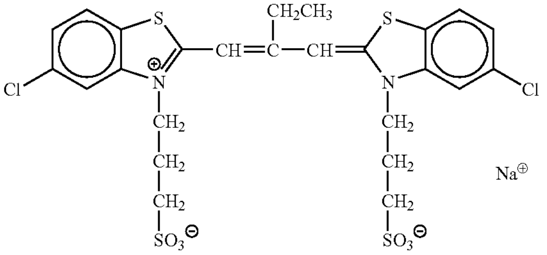

TABLE 6-continued

| First Dye | | Second Dye | |
|---|---|---|---|
| Kind of Dye and Addition Amount ($10^{-3}$ mol/mol-Ag) | Kind of Dye and Addition Amount ($10^{-3}$ mol/mol-Aq) | Kind of Dye and Addition Amount ($10^{-3}$ mol/mol-Ag) | Kind of Dye and Addition Amount ($10^{-3}$ mol/mol-Ag) |

H-4

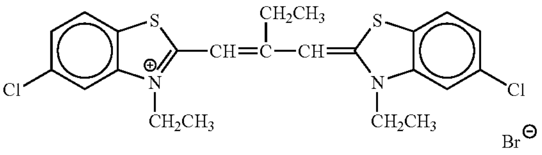

H-5

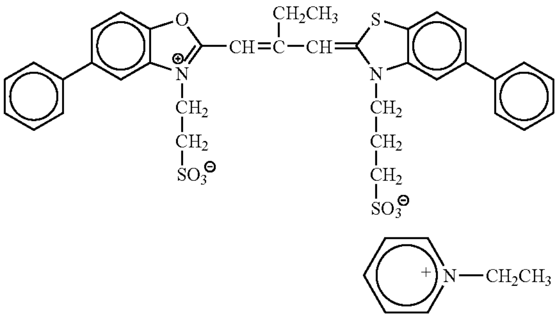

The results obtained are shown in Tables 7 and 8. As is shown in Table 7, using the two kinds of dyes according to the present invention, multilayer adsorption onto the grain surface became feasible As is shown in Table 8, color sensitization sensitivity was conspicuously increased.

TABLE 7

| | First Dye | | | Second Dye | | |
|---|---|---|---|---|---|---|
| | Kind of Dye and Adsorption Amount ($10^{-3}$ mol/ mol-Ag) | Kind of Dye and Adsorption Amount ($10^{-3}$ mol/ mol-Ag) | Total Covering Rate (%) | Kind of Dye and Adsorption Amount ($10^{-3}$ mol/ mol-Ag) | Kind of Dye and Adsorption Amount ($10^{-3}$ mol/ mol-Ag) | Total Covering Rate (%) |
| Comparison 1 | H-3 (0.62) | — | 95 | — | — | — |
| Comparison 2 | H-4 (0.59) | — | 90 | — | — | — |
| Invention 1 | H-4 (0.17) | III-29 (0.58) | 132 | H-5 (0.07) | III-29 (0.35) | 62 |
| Invention 2 | — | III-29 (0.91) | 143 | H-5 (0.05) | III-28 (0.47) | 88 |
| Invention 3 | H-4 (0.21) | III-29 (0.59) | 138 | — | III-28 (0.62) | 92 |

TABLE 8

| | Blue Sensitivity | Minus Blue Sensitivity | Color Sensitization Sensitivity (minus blue sensitivity/ blue sensitivity) |
|---|---|---|---|
| Comparison 1 | 100 | 100 | 100 |
| Comparison 2 | 99 | 99 | 100 |
| Invention 1 | 98 | 136 | 139 |
| Invention 2 | 99 | 173 | 178 |
| Invention 3 | 95 | 203 | 210 |

Example 15

To 500 g of Emulsion B was added 0.5 liters of water with maintaining the temperature at 40° C., then the first dye shown in Table 9 was added in the amount indicated as Addition A in Table 9 and stirred for 10 minutes at 40° C. The temperature was thereafter risen to 55° C., 7.8 ml of an aqueous solution containing 0.1M of potassium thiocyanate and 3 ml of 0.01% chloroauric acid were added, and further 6.6 ml of 0.01% sodium thiosulfate and 5.3 ml of M/10,000 (diphenyl)-(pentafluorophenyl)-phosphineselenide were added and ripening was conducted at 55° C. for 30 minutes. Subsequently, the first dye was added in the amount indicated as Addition B in Table 9 and stirred at 55° C. for 30 minutes, then 0.6 liters of the second dye in concentration of 1/500 mol/liter was added thereto and stirred at 55° C. for 30 minutes.

The dye adsorption amount of the obtained emulsion and the light absorption strength per unit surface area of emulsion grains were found in the same manner as in Example 13.

Exposure and development were also conducted in the same manner as in Example 13. Optical density of the development processed film was measured using a Fuji automatic densitometer. Sensitivity was the reciprocal of the exposure amount required to give an optical density of fog +0.2 and expressed as a relative value taking Comparison 1 as a control, with fog being the density at the unexposed part.

TABLE 9

| | First Dye | | | Second Dye | |
|---|---|---|---|---|---|
| | Kind | Addition A ($10^{-3}$ mol/ mol-Ag) | Addition B ($10^{-3}$ mol/ mol-Ag) | Kind | Amount ($10^{-3}$ mol/ mol-Ag) |
| Comparison 1 | H-6 | 1.45 | 4.5 | H-7 | 3.2 |
| Comparison 2 | III-68 | 1.45 | 4.5 | — | — |
| Invention 1 | III-68 | 1.45 | 4.5 | III-40 | 3.2 |
| Invention 2 | III-68 | 5.95 | — | III-40 | 3.2 |
| Invention 3 | III-68 | 1.45 | 4.5 | III-40 | 3.2 |

H-6

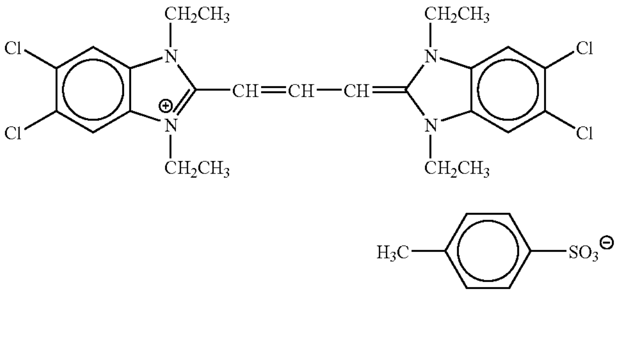

TABLE 9-continued

| | First Dye | | Second Dye | |
|---|---|---|---|---|
| Kind | Addition A ($10^{-3}$ mol/ mol-Ag) | Addition B ($10^{-3}$ mol/ mol-Ag) | Kind | Amount ($10^{-3}$ mol/ mol-Ag) |

H-7

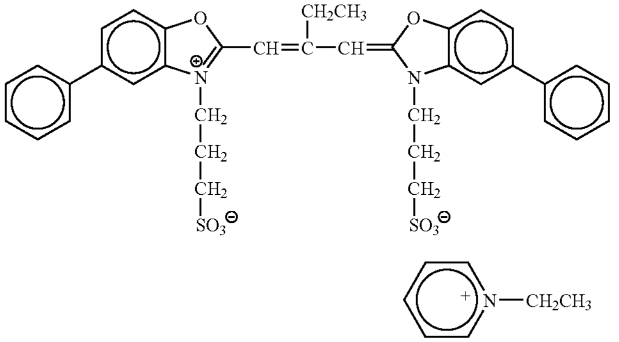

The dye adsorption amount and the light absorption strength per unit surface area are shown in Table 10 and sensitivity in Table 11 below. Thus, the adsorption amount of sensitizing dyes could be increased by using the two kinds of dyes according to the present invention, and the light absorption strength per unit surface area could also be improved. Further, as chemical sensitization was conducted when the optimal amount of dye was added, the site of the chemical sensitization speck was limited and intrinsic sensitivity could also be increased. The sensitivity due to the improvement of light absorption factor could be largely increased.

TABLE 10

| | Light | First Layer | | Second Layer | |
|---|---|---|---|---|---|
| | Absorption Strength per Unit Surface Area | Adsorption Amount ($10^{-3}$ mol/ mol-Ag) | Covering Rate (%) | Adsorption Amount ($10^{-3}$ mol/ mol-Ag) | Covering Rate (%) |
| Comparison 1 | 89 | 1.41 | 94 | 0.03 | 2 |
| Comparison 2 | 92 | 1.47 | 98 | — | — |
| Invention 1 | 173 | 2.52 | 165 | 1.00 | 66 |
| Invention 2 | 429 | 5.01 | 351 | 3.00 | 200 |
| Invention 3 | 483 | 4.98 | 345 | 3.00 | 200 |

TABLE 11

| | Blue Sensitivity | Minus Blue Sensitivity | Color Sensitization Sensitivity (minus blue sensitivity/ blue sensitivity) |
|---|---|---|---|
| Comparison 1 | 100 | 100 | 100 |
| Comparison 2 | 101 | 100 | 99 |
| Invention 1 | 97 | 181 | 170 |
| Invention 2 | 91 | 306 | 320 |
| Invention 3 | 97 | 342 | 340 |

Example 16

In Emulsion 1 in Example 1 of JP-A-7-92601, H-9 was added in an amount of $3.25\times10^{-3}$ mol/mol-Ag, then H-10 was added in an amount of $3.0\times10^{-3}$ mol/mol-Ag, in place of Spectral Sensitizing Dyes S-4 and S-5, the thus-obtained emulsion was designated Emulsion 5A, or III-68 was added in an amount of $3.25\times10^{-3}$ mol/mol-Ag, then III-40 was added in an amount of $3.0\times10^{-3}$ mol/mol-Ag, this emulsion was designated Emulsion 5B Further, in Emulsion 1 in Example 1 of JP-A-7-92601, the silver potential during the second double jet was changed from +65 mV to +115 mV, further, H-9 was added in an amount of $3.25\times10^{-3}$ mol/mol-Ag, then H-10 was added in an amount of $3.0\times10^{-3}$ mol/mol-Ag, in place of Spectral Sensitizing Dyes S-4 and S-5, the thus-obtained emulsion was designated Emulsion 5C, or III-68 was added in an amount of $3.25\times10^{-3}$ mol/mol-Ag, then III-40 was added in an amount of $3.0\times10^{-3}$ mol/mol-Ag, this emulsion was designated Emulsion 5D.

Multilayer color photographic materials were prepared in the same manner as the preparation of Sample No. 401 in Example 4 of JP-A-7-92601. Emulsion 1 in the ninth layer of Sample No. 401 in Example 4 of JP-A-7-92601 was replaced with Emulsion 5A or 5B, the thus-obtained samples were designated Sample No. 501 and Sample No. 502. Similarly, Emulsion 1 in the ninth layer of Sample No. 401 in Example 4-of JP-A-7-92601 was replaced with Emulsion 5C or 5D, and these samples were designated Sample No. 503 and Sample No. 504.

The sensitivity of the thus-obtained samples was evaluated. In the same manner as in Example 4 of JP-A-7-92601, samples were subjected to exposure for 1/50 seconds and color reversal development processing and magenta density was measured. The results obtained are shown in Table 12 below. Sensitivity was a reciprocal of exposure amount required to, give a density of a minimum density +0.2, which was obtained with sufficient exposure, and was expressed as a relative value taking the sensitivity of Sample No. 501 as 100.

TABLE 12

| Sample No. | Sensitivity (fog + 0.2) |
|---|---|
| Sample No. 501 | 100 (control) |
| Sample No. 502 | 201 |
| Sample No. 503 | 101 |
| Sample No. 504 | 242 |

H-9

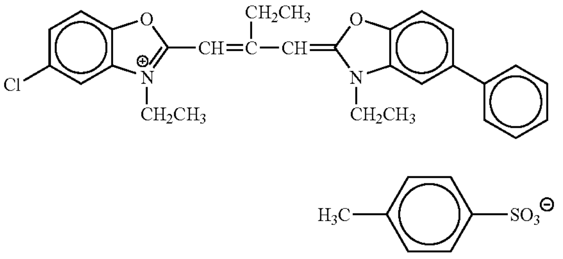

H-10

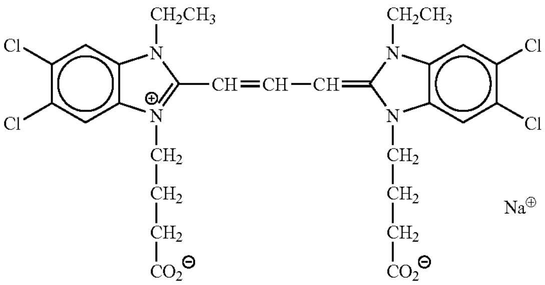

It was found that the sensitivity of a reversal multilayer color photographic material was also improved by the increase of the dye adsorption amount using the two kinds of dyes according to the present invention.

Example 17

An octahedral silver bromide internal latent image type direct positive emulsion and a hexagonal tabular silver bromide internal latent image type direct positive emulsion were prepared in the same manner as the preparation of Emulsions 1 and 5 in Example 1 of JP-A-5-313297 and these emulsions were named Emulsion 6A and Emulsion 6B Color diffusion transfer photographic films were prepared in the same manner as the preparation of Sample No. 101 in Example 1 of JP-A-0.5-313297. Emulsion-2 in the sixteenth layer of Sample No. 101 in Example 1 of JP-A-5-313297 was replaced with Emulsion 6A, H-11 was added in an amount of $4.5\times10^{-3}$ mol/mol-Ag, then III-1 was added in an amount of $4.0\times10^{-3}$ mol/mol-Ag, in place of Sensitizing Dye (3), the thus-obtained sample was designated Sample No. 601, or III-1 was added in an amount of $4.5\times10^{-3}$ mol/mol-Ag, then III-25 was added in an amount of $4.0\times10^{-3}$ mol/mol-Ag, this sample was designated Sample No. 602. Similarly, Emulsion-2 in the sixteenth layer of Sample No. 101 in the same example was replaced with Emulsion 6B, H-11 was added in an amount of $4.5\times10^{-3}$ mol/mol-Ag, then H-12 was added in an amount of $4.0\times10^{-3}$ mol/mol-Ag, in place of Sensitizing Dye (3), the thus-obtained sample was designated Sample No. 603, or III-1 was added in an amount of $4.5\times10^{-3}$ mol/mol-Ag, then III-25 was added in an amount of $4.0\times10^{-3}$ mol/mol-Ag, this sample was designated Sample No. 604.

For examining the sensitivity of the thus-obtained samples, processing was carried out using the same exposure, processing step and processing solutions as in Example 1 of JP-A-5-313297 and transfer density was measured using a color densitometer.

The results obtained are shown in Table 13 below. Sensitivity was a reciprocal of exposure amount required to give density of 1.0 and expressed as a relative value taking Sample No. 601 as a control.

TABLE 13

| Sample No. | Sensitivity (density 1.0) |
|---|---|
| Sample No. 601 | 100 (control) |
| Sample No. 602 | 215 |
| Sample No. 603 | 199 |
| Sample No. 604 | 254 |

H-11

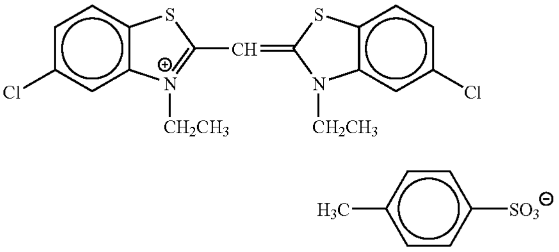

H-12

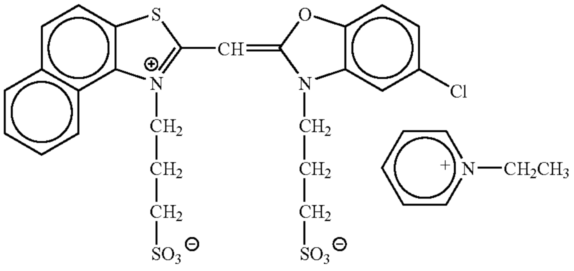

It was found that the sensitivity of a color diffusion transfer photographic film was also improved due to the increase of the dye adsorption amount by the addition of two kinds of dyes according to the present invention.

Example 18

In the preparation of Emulsion F in Example 2 of JP-A-4-142536, a red-sensitive sensitizing dye (S-1) was not added before sulfur sensitization, in addition to sulfur sensitization using triethylthiourea, chloroauric acid was used in combination and optimally gold-sulfur sensitized, and after gold-sulfur sensitization, H-14 was added in an amount of $3.5\times10^{-4}$ mol/mol-Ag, then H-13 was added in an amount of $3.5\times10^{-4}$ Mol/mol-Ag, the thus-obtained emulsion was designated Emulsion 7A, or III-1 was added in an amount of $3.5\times10^{-4}$ mol/mol-Ag, then III-2 was added in an amount of $3.5\times10^{-4}$ mol/mol-Ag, this emulsion was designated Emulsion 7B.

Multilayer color photographic papers were prepared in the same manner as the preparation of Sample No. 20 in Example 1 of JP-A-6-347944. The emulsion in the first layer of Sample No. 20 in Example 1 of JP-A-6-347944 was replaced with Emulsion 7A or 7B, these samples were designated Sample No. 701 and Sample No. 702.

For examining the sensitivity of the thus-obtained samples, samples were exposed for 1/10 second through an optical wedge and a blue filter using Fuji FW type sensitometer (a product of Fuji Photo Film Co., Ltd.), color development processing was carried out using the same processing step and processing solutions in Example 1 of JP-A-6-347944 and yellow density was measured. The results obtained are shown in Table 14 below. Sensitivity was a reciprocal of exposure amount required to give a density of fog +0.1 and expressed as a relative value taking Sample No. 701 as a control.

TABLE 14

| Sample No. | Sensitivity (fog + 0.2) |
|---|---|
| Sample No. 701 | 100 (control) |
| Sample No. 702 | 268 |

H-13

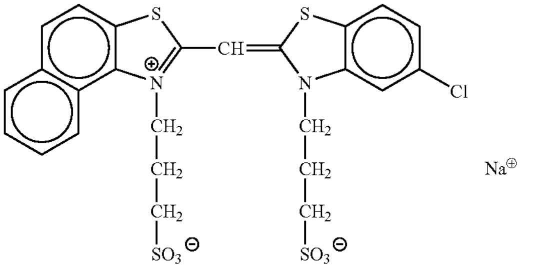

H-14

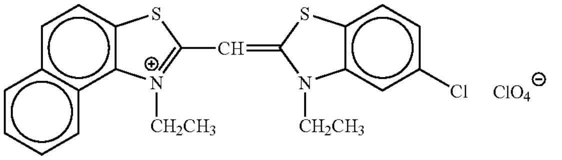

It was found that the sensitivity of a multilayer color photographic paper was also improved due to the increase of the dye adsorption amount by the addition of two kinds of dyes according to the present invention.

Example 19

Tabular silver chloride emulsions were prepared in the same manner as the preparation of Emulsion A in Example 1 of JP-A-8-122954. In chemical sensitization (B) in Example 1 of the same patent, in place of Sensitizing Dye-1 and Dye-2, H-1 was added in an amount of $1.0\times10^{-3}$ mol/mol-Ag, then gold-sulfur-selenium sensitization was conducted, further, H-1 was added in an amount of $1.5\times10^{-3}$ mol/mol-Ag, subsequently, H-2 was added in an amount of $2.2\times10^{-3}$ mol/mol-Ag and H-15 was added in an amount of $3.8\times10^{-5}$ mol/mol-Ag, the thus-obtained emulsion was designated Emulsion 8A, or III-41 was added in an amount of $1.0\times10^{-3}$ mol/mol-Ag, then gold-sulfur-selenium sensitization was conducted, further, III-41 was added in an amount of $1.5\times10^{-3}$ mol/mol-Ag, and III-40 was added in an amount of $2.3\times10^{-3}$ mol/mol-Ag, the thus-obtained emulsion was designated Emulsion 8B.

Coated samples were prepared by replacing the emulsion in Example 1 of JP-A-8-122954 with Emulsion 8A or Emulsion 8B and an emulsion layer and a surface protective layer were coated on both sides of a support by a simultaneous coating method in the same manner as in Example 1 of JP-A-8-122954, these samples were designated Sample Nos. 801 and 802. The coated silver amount per one side was 1.75 g/m$^2$.

For examining the sensitivity of the thus-obtained samples, samples were exposed for 0.05 second from both sides through an X-ray ortho-screen HGM produced by Fuji Photo Film Co., Ltd. and processed with the same automatic processor and processing solutions as used in Example 1 of JP-8-122954. The results obtained are shown in Table 15 below. Sensitivity was the reciprocal of the exposure amount required to give a density of fog +0.1 and expressed as a relative value taking the sensitivity of Sample No. 801 as a control.

TABLE 15

| Sample No. | Sensitivity (fog + 0.2) |
|---|---|
| Sample No. 801 | 100 (control) |
| Sample No. 802 | 301 |

H-15

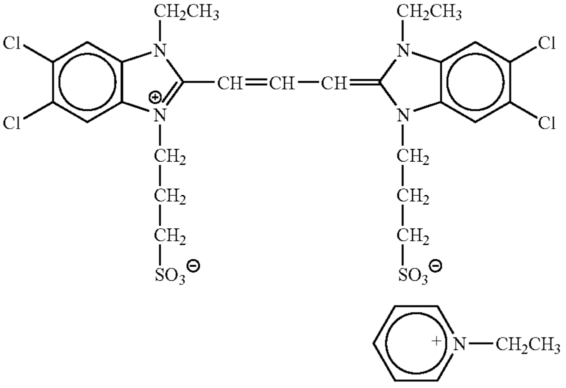

Reference Example 1

The excitation wavelength and fluorescent intensity of the dyes of the present invention were compared with those of conventionally used dye. The following dye was used as conventionally used dye. The results obtained are shown in Table 16 below.

TABLE 16

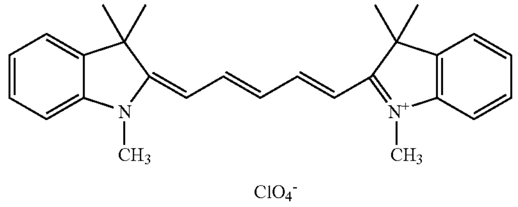

| Dye No. | Excitation Maximum Wavelength (nm) | Fluorescence Maximum Wavelength (nm) | Fluorescent Intensity |
|---|---|---|---|
| III-71 | 622 | 641 | 531 |
| III-72 | 626 | 645 | 551 |
| III-73 | 628 | 648 | 554 |
| Comparative Dye | 643 | 661 | 137 |

As is apparent from the results in Table 16, the dyes according to the present invention are suitable for excitation using inexpensive helium-neon laser light sources (633 nm), and fluorescent intensity of the dyes according to the present invention is stronger than conventional dyes.

Reference Example 2

The excitation wavelength and fluorescent intensity of the dyes of the present invention were compared with those of conventionally used dye. The following dye was used as conventionally used dye. The results obtained are shown in Table 17 below.

TABLE 17

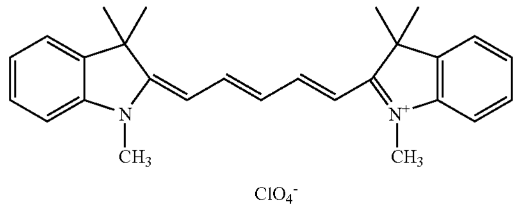

| Dye No. | Absorption Maximum Wavelength (nm) | Molecular Extinction Coefficient | Excitation Maximum Wavelength (nm) | Fluorescence Maximum Wavelength (nm) | Fluorescent Intensity |
|---|---|---|---|---|---|
| III-76 | 629 | 238,000 | 631 | 657 | 460 |
| III-77 | 631 | 238,000 | 633 | 658 | 459 |
| III-78 | 632 | 240,000 | 633 | 657 | 460 |
| III-79 | 630 | 240,000 | 632 | 657 | 460 |
| III-80 | 631 | 216,000 | 633 | 658 | 460 |
| Comparative Dye | 642 | 240,000 | 643 | 661 | 137 |

Solvent: methanol, dye density: $1.0 \times 10^{-6}$ M

As is apparent from the results in Table 17, the dyes according to the present invention are suitable for excitation using inexpensive helium-neon laser light sources (633 nm), and fluorescent intensity of the dyes according to the present invention is stronger than conventional dyes.

While the invention has been described in detail and with reference to specific examples thereof, it will be apparent to one skilled in the art that various changes and modifications can be made therein without departing from the spirit and scope thereof.

What is claimed is:

1. A compound represented by formula (III):

(III)

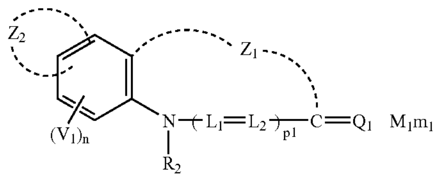

wherein $Z_1$ represents an atomic group necessary to form thiazole; $Z_2$ represents an atomic group selected from the group consisting of a furan ring and a thiophene ring which are condensed to a benzo ring to form a tetracyclic ring; $R_2$ represents a substituted or unsubstituted alkyl group or a substituted or unsubstituted aryl group; $L_1$ and $L_2$ each represents a methine group; $p_1$ represents 0; $V_1$ represents a substituent selected from a halogen atom, a mercapto group, a cyano group, a carboxyl group, a phosphoric acid group, a sulfo group, a hydroxyl group, a carbamoyl group having from 1 to 10 carbon atoms, a sulfamoyl group having from 0 to 10 carbon atoms, a nitro group, an alkoxyl group having from 1 to 20 carbon atoms, an aryloxy group having from 6 to 20 carbon atoms, an acyl group having from 1 to 20 carbon atoms, an acyloxy group having from 1 to 20 carbon atoms, an acylamino group having from 1 to 20 carbon atoms, a sulfonyl group having from 1 to 20 carbon atoms, a sulfinyl group having from 1 to 20 carbon atoms, a sulfonylamino group having from 1 to 20 carbon atoms, an amino group, a substituted amino group selected from methylamino, dimethylamino, benzylamino, anilino, and diphenylamino, an ammonium group having from 0 to 15 carbon atoms, a hydrazino group having from 0 to 15 carbon atoms, a ureido group having from 1 to 15 carbon atoms, an imido group having from 1 to 15 carbon atoms, an alkylthio group having from 1 to 20 carbon atoms, an arylthio group having from 6 to 20 carbon atoms, an alkoxycarbonyl group having from 2 to 20 carbon atoms, an aryloxycarbonyl group having from 6 to 20 carbon atoms, an unsubstituted alkyl group having from 1 to 18 carbon atoms, a substituted-alkyl group selected from hydroxymethyl, trifluoromethyl, benzyl, carboxyethyl, ethoxycarbonylmethyl, and acetylaminomethyl, an unsaturated hydrocarbon group having from 2 to 18 carbon atoms, an unsubstituted aryl group having from 6 to 20 carbon atoms, a substituted aryl group selected from p-carboxyphenyl, p-nitrophenyl, 3,5-dichlorophenyl, p-cyanophenyl, m-fluorophenyl and p-tolyl, an unsubstituted heterocyclic group having from 1 to 20 carbon atoms, and a methylpyridyl group; $Q_1$ represents a methine group or a polymethine group necessary to form a methine dye; $M_1$ represents an electric charge balancing counter ion; and $m_1$ represents a number of from 0 to 10 necessary to neutralize the electric charge of the molecule; and n represents 0, 1 or 2, and when n represents 2, a plurality of $V_1$ may be the same or different.

2. The compound as claimed in claim 1, wherein the selected atomic group for $Z_2$ is a furan ring.

3. The compound as claimed in claim 1, wherein the compound represented by formula (III) is represented by formula (VIII):

(VIII)

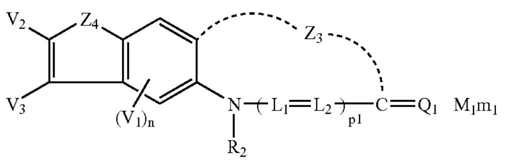

wherein $Z_4$ represents an oxygen atom or a sulfur atom; $Z_3$ represents an atomic group necessary to form thiazole, $L_1$, $L_2$, $p_1$, $V_1$, n, $R_2$, $Q_1$, $M_1$, and $m_1$ each has the same meaning as described in formula (III); and $V_2$ and $V_3$ each represents a substituent selected from a halogen atom, a mercapto group, a cyano group, a carboxyl group, a phosphoric acid group, a sulfo group, a hydroxyl group, a carbamoyl group having from 1 to 10 carbon atoms, a sulfamoyl group having from 0 to 10 carbon atoms, a nitro group, an alkoxyl group having from 1 to 20 carbon atoms, an aryloxy group having from 6 to 20 carbon atoms, an acyl group having from 1 to 20 carbon atoms, an acyloxy group having from 1 to 20 carbon atoms, an acylamino group having from 1 to 20 carbon atoms, a sulfonyl group having from 1 to 20 carbon atoms, a sulfinyl group having from 1 to 20 carbon atoms, a sulfonylamino group having from 1 to 20 carbon atoms, an amino group, a substituted amino group selected from methylamino, dimethylamino, benzylamino, anilino, and diphenylamino, an ammonium group having from 0 to 15 carbon atoms, a hydrazino group having from 0 to 15 carbon atoms, a ureido group having from 1 to 15 carbon atoms, an imido group having from 1 to 15 carbon atoms, an alkylthio group having from 1 to 20 carbon atoms, an arylthio group having from 6 to 20, carbon atoms, an alkoxycarbonyl group having from 2 to 20 carbon atoms, an aryloxycarbonyl group having from 6 to 20 carbon atoms, an unsubstituted alkyl group having from 1 to 18 carbon atoms, a substituted-alkyl group selected from hydroxymethyl, trifluoromethyl, benzyl, carboxyethyl, ethoxycarbonylmethyl, and acetylaminomethyl, an unsaturated hydrocarbon group having from 2 to 18 carbon atoms, an unsubstituted aryl group having from 6 to 20 carbon atoms, a substituted aryl group selected from p-carboxyphenyl, p-nitrophenyl, 3,5-dichlorophenyl, p-cyanophenyl, m-fluorophenyl and p-tolyl, an unsubstituted heterocyclic group having from 1 to 20 carbon atoms, and a methylpyridyl group, and $V_2$ and $V_3$ form a condensed ring containing $V_2$ and $V_3$ 4. The compound as claimed in claim 3, wherein $R_2$ represents an alkyl group having an aryl group as a substituent or an aryl group.

5. The compound as claimed in claim 3, wherein at least one substituent represented by $V_1$ is a group having at least one sulfo group, carboxyl group, phosphonic acid group or hydroxyl group.

6. The compound as claimed in claim 3, wherein at least one substituent represented by $V_2$ or $V_3$ in formula (VIII) is a group having at least one sulfo group, carboxyl group, phosphonic acid group or hydroxyl group.

7. The compound as claimed in claim 1, wherein $R_2$ represents an alkyl group having an aryl group as a substituent or an aryl group.

8. The compound as claimed in claim 1, wherein at least one substituent represented by $V_1$ is a group having at least one sulfo group, carboxyl group, phosphonic acid group or hydroxyl group.

* * * * *